(12) United States Patent
Schirmer et al.

(10) Patent No.: US 10,676,763 B2
(45) Date of Patent: Jun. 9, 2020

(54) MICROBIAL PRODUCTION OF FATTY DIOLS

(71) Applicant: REG Life Sciences, LLC, Ames, IA (US)

(72) Inventors: Andreas W. Schirmer, South San Francisco, CA (US); Noah Helman, South San Francisco, CA (US); Haibo Wang, South San Francisco, CA (US); Zhihao Hu, South San Francisco, CA (US); Vikranth Arlagadda, South San Francisco, CA (US); Alma Itzel Ramos-Solis, South San Francisco, CA (US); Elizabeth Clarke, South San Francisco, CA (US)

(73) Assignee: GENOMATICA, INC., San Diego, CA (US)

( * ) Notice: Subject to any disclaimer, the term of this patent is extended or adjusted under 35 U.S.C. 154(b) by 0 days.

(21) Appl. No.: 15/326,844

(22) PCT Filed: Jul. 17, 2015

(86) PCT No.: PCT/US2015/041031
§ 371 (c)(1),
(2) Date: Jan. 17, 2017

(87) PCT Pub. No.: WO2016/011430
PCT Pub. Date: Jan. 21, 2016

(65) Prior Publication Data
US 2017/0204436 A1    Jul. 20, 2017

Related U.S. Application Data

(60) Provisional application No. 62/026,573, filed on Jul. 18, 2014.

(51) Int. Cl.
| | | |
|---|---|---|
| *C12P 7/18* | (2006.01) | |
| *C12N 9/16* | (2006.01) | |
| *C12N 9/00* | (2006.01) | |
| *C12N 15/52* | (2006.01) | |
| *C12N 9/18* | (2006.01) | |
| *C12N 9/02* | (2006.01) | |
| *C12N 9/04* | (2006.01) | |
| *C12N 15/63* | (2006.01) | |

(52) U.S. Cl.
CPC ............. *C12P 7/18* (2013.01); *C12N 9/16* (2013.01); *C12N 9/93* (2013.01); *C12N 15/52* (2013.01); *C12Y 101/01* (2013.01); *C12Y 102/01* (2013.01); *C12Y 102/01042* (2013.01); *C12Y 301/01005* (2013.01); *C12Y 301/02* (2013.01); *C12Y 301/02014* (2013.01); *C12Y 602/01003* (2013.01)

(58) Field of Classification Search
CPC .... C12Y 602/01003; C12Y 102/01042; C12Y 301/01005; C12Y 301/02014; C12Y 101/01; C12Y 102/01; C12Y 301/02; C12N 9/16; C12N 9/93; C12N 15/52; C12P 7/18

See application file for complete search history.

(56) References Cited

U.S. PATENT DOCUMENTS

| | | |
|---|---|---|
| 3,806,615 A | 4/1974 | Frankenfeld et al. |
| 5,000,000 A | 3/1991 | Ingram et al. |
| 5,028,539 A | 7/1991 | Ingram et al. |
| 5,424,202 A | 6/1995 | Ingram et al. |
| 5,482,846 A | 1/1996 | Ingram et al. |
| 5,602,030 A | 2/1997 | Ingrahm et al. |
| 7,470,526 B2 | 12/2008 | Cotticelli et al. |
| 8,097,439 B2 | 1/2012 | Alibhai et al. |
| 8,110,093 B2 | 2/2012 | Friedman et al. |
| 8,110,670 B2 | 2/2012 | Hu et al. |
| 8,183,028 B2 | 5/2012 | Alibhai et al. |
| 8,232,924 B2 | 7/2012 | Bucca et al. |
| 8,268,599 B2 | 9/2012 | Schirmer et al. |
| 8,283,143 B2 | 10/2012 | Hu et al. |
| 8,372,610 B2 | 2/2013 | Lee et al. |
| 8,530,221 B2 | 9/2013 | Hu et al. |
| 2008/0248539 A1 | 10/2008 | Giver et al. |
| 2012/0172281 A1* | 7/2012 | Scheibel .......... C11D 1/14 510/493 |
| 2013/0052699 A1 | 2/2013 | Crowe et al. |
| 2013/0177951 A1 | 7/2013 | Burk et al. |
| 2014/0051136 A1 | 2/2014 | Liao et al. |

(Continued)

FOREIGN PATENT DOCUMENTS

| | | |
|---|---|---|
| CN | 1295130 A | 5/2001 |
| EP | 2 024 491 | 11/2014 |
| JP | 2011-103863 A | 6/2011 |

(Continued)

OTHER PUBLICATIONS

Steen et al., Microbial production of fatty-acid derived fuels and chemicals from plant biomass. Nature, 2010, vol. 46: 559-563 (Year: 2010).*

Broun et al., Catalytic plasticity of fatty acid modification enzymes underlying chemical diversity of plant lipids. Science, 1998, vol. 282: 1315-1317. (Year: 1998).*

Devos et al., Practical limits of function prediction. Proteins: Structure, Function, and Genetics. 2000, vol. 41: 98-107. (Year: 2000).*

Kisselev L., Polypeptide release factors in prokaryotes and eukaryotes: same function, different structure. Structure, 2002, vol. 10: 8-9. (Year: 2002).*

Seffernick et al., Melamine deaminase and Atrazine chlorohydrolase: 98 percent identical but functionally different. J. Bacteriol., 2001, vol. 183 (8): 2405-2410. (Year: 2001).*

(Continued)

*Primary Examiner* — Ganapathirama Raghu
(74) *Attorney, Agent, or Firm* — Foley & Lardner LLP

(57) ABSTRACT

The disclosure relates to fatty diols and recombinant microorganisms for producing them. More particularly, the disclosure relates to recombinant microorganisms engineered to produce fatty diols via fermentation. Further encompassed is a process that uses the microorganisms to produce fatty diols from a simple carbon source.

13 Claims, 11 Drawing Sheets

Specification includes a Sequence Listing.

(56) References Cited

U.S. PATENT DOCUMENTS

| | | |
|---|---|---|
| 2014/0273114 A1 | 9/2014 | San et al. |
| 2017/0029854 A1 | 2/2017 | Del Cardayre et al. |

FOREIGN PATENT DOCUMENTS

| | | |
|---|---|---|
| WO | WO-2004/074476 | 9/2004 |
| WO | WO-2006/008508 | 1/2006 |
| WO | WO-2010/127318 | 11/2010 |
| WO | WO-2011/150410 | 12/2011 |
| WO | WO-2012/096686 A1 | 7/2012 |
| WO | WO-2013/023519 | 2/2013 |
| WO | WO-2013/036812 A1 | 3/2013 |
| WO | WO-2013/152051 | 10/2013 |
| WO | WO-2013/152052 | 10/2013 |
| WO | WO-2014/201474 A1 | 12/2014 |

OTHER PUBLICATIONS

Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Altschul et al. "Basic Local Alignment Search Tool," (1990) J. Mol. Biol. 215(3):403-410.
Altschul et al., "Protein database searches using compositionally adjusted substitution matrices," FEBS J. 272(20): 5101-5109 (2005).
Amann et al., "Tightly regulated tac promoter vectors useful for the expression of unfused and fused proteins in *Escherichia coli*," Gene, 69: 301-315 (1988).
Baldari et al. "A novel leader peptide which allows efficient secretion of a fragment of human interluken 1beta in *Saccharomyces serevisiae*," (1987) EMBO J. 6:229-234.
Braun, "Minireviews—FhuA (TonA), the Career of a Protein," J. Bacteriol. 191(11): 3431-3436 (2009).
Clark, "Regulation of Fatty Acid Degration in *Escherichia coli*: Analysis by Operon Fusion," J Bacteriol. 148(2): 521-526 (1981).
Grosjean et al., "Preferential codon usage in prokaryotic genes: the optimal codon-anticodon interaction energy and the selective codon usage in efficiently expressed genes," Gene 18:199-209 (1982).
He et al. "Clutamate-119 of the Large-alpha-Subunit is the Catalytic Base in the Hydration of 2-trans-Enoyl-Coenzyme A Catalyzed by the Multienzyme Complex of Fatty Acid Oxidation from *Escherichia coli*," (1997) Biochemistry 36(36): 11044-11049.
He et al. "Histidine-450 Is the Catalytic Residue of L-3-Hydroxyacyl Coenzyme A Dehydrogenase Associated with the Large alpha-Subunit of the Multienzyme Complex of Fatty Acid Oxidation from *Escherichia coli*,"(1996) Biochemistry 35(29): 9625-9630.
Julsing et al. "Outer Membrane Protein AlkL Boosts Biocatalytic Oxyfunctionalization of Hydriophobic Substrates in *Escherichia coli*," (2012) Appl. Environ Microbiol. 78:5724-5733.
Kurjan et al., Structure of a Yeast Pheromone Gene (MFx): A Putative x-Factor precursor Contains Four Tandem Copies of Mature x-Factor, Cell, vol. 30, pp. 933-943 (1982).
Lucklow et al. "High Level Expression of Nonfused Foreign Genes with Autographa californica Nuclear Polyhedrosis Virus Expression Vectors," (1989) Virology 170, pp. 31-39.
Maniatis et al. Regulation of Inducible and Tissue-Specific Gene Expression, Science 236, pp. 1237-1245, Jun. 5, 1987.
Needleman and Wunsch, J. Mol. Biol., 48: 444-453 (1970).
Rosenberg, "Multiple Sequence Alignment Accuracy and Evolutionary Distance Estimation," BMC Bioinformatics 6: 278 (2005).
Sambrook et al., "Molecular Cloning: A Laboratory Manual," second edition, Cold Spring Harbor Laboratory (1989), 31 pages.
Schultz et al., "Expression and secretion in yeast of a 400-kDa envelope glycoprotein derived from Epstein-Barr virus," Gene 54: 113-123 (1987).
Smith et al. "Production of Human Beta Interferon in Insect Cells Infected with a Vaculovirus Expression Vector," (1983) Mol. Cell. Biol. 3:2156-2165.
Smith et al., Single-step purification of polypeptides expressed in *Escherichia coli* as fusions with glutathione S-transferase, Gene, 67, pp. 31-40 (1988).
Studier et al., Gene Expression Technology: Methods in Enzymology 185, Academic Press, San Diego, CA, pp. 60-89 (1990).
Wang et al, "Development of a New Strategy for Production of Medium-Chain-Length Polyhydroxyalkanoates by Recombinant *Escherichia coli* via Inexpensive Non-Fatty Acid Feedstocks," Appl Env Microbiol; 2012, pp. 519-527.
Yang et al. (1995) Biochemistry 34(19): 6441-6447.
Akhtar et al., "Carboxylic acid reductase is a versatile enzyme for the conversion of fatty acids into fuels and chemical commodities," Proceedings of the National Academy of Sciences, vol. 110, No. 1, Jan. 2, 2013, pp. 87-92, Supplemental Information 1-36.
Australian Examination Report issued in Australian Patent Application No. 2015289430 dated Feb. 15, 2019, 5 pages.
Broun et al., "A bifunctional oleate 12-hydroxylase: Desaturase from Lesquerella fend/err", Plant Journal, Nov. 13, 1998, vol. 13, Issue 2, pp. 201-210.
Chen Peng, "Synthesis of very-long-chain bifunctional and isotope-labeled compounds for biochemical investigations into novel compounds in plant cuticular waxes / Chapter 5. Beta-keto acid derivatives: pathway intermediates and end products," The University of British Columbia (Vancouver) Thesis, Dec. 21, 2012, pp. 57-60.
Communication issued on EP Appl. 15718726.1, dated Jan. 30, 2018, 9 pages.
Communication issued on EP Appl. 15745054.5 dated Aug. 17, 2017, 6 pages.
Communication issued on EP Appl. 12719914.9, dated May 28, 2018, 3 pages.
Coursolle et al., "Production of Long Chain Alcohols and Alkanes upon coexpression of a acyl-ACP reductase and aldehyde-deformylating oxygenase with a bacterial type-I fatty acid synthase in *E. coli*," Molecular Biosystems, vol. 11, Jun. 23, 2015. pp. 2464-2472.
Examination Report issued on Australian Appl. 2014225436, dated Oct. 4, 2017, 3 pages.
Examination Report issued on Australian Appl. 2009329970, dated Mar. 17, 2016, 3 pages.
Extended European Search Report issued on EP Appl. 18189374.4 dated Feb. 20, 2019, 9 pages.
Extended European Search Report issued on EP Appl. 18160746.6, dated Jun. 18, 2018, 12 pages.
Flores et al., "Expression of PEP carboxylase from *Escherichia coli* complements the phenotypic effects of pyruvate carboxylase mutations in *Saccharomyces cerevisiae*," FEBS Letters, Aug. 4, 1997, vol. 412, pp. 531-534.
Foreign Action other than Search Report on EP 18189374.4 dated Oct. 23, 2019, 6 pages.
Foreign Action other than Search Report on ID P00201701025 dated Jul. 16, 2019, 4 pages. (with English translation).
Foreign Action other than Search Report on JP 2017-502836 dated Jun. 26, 2019, 4 pages. (with English translation).
Fouts, D. et al., "Acyl-CoA thioesterase I", UniProtKB Accession No. B5Y0L7_KLEP3, Nov. 25, 2008, 4 pages.
GenBank, accession No. ABM17701, Aug. 25, 2017, www.ncbi.nlm.nih.gov, 1 page.
Holtzapple and Schmidt-Dannert, "Marinobacter hydrocarbonoclasticus strain DSM8798 wax ester synthase (ws2)gene, complete cds" Genbank, Accession No. EF219377.(§§) Https://www.ncbi.nlm.nih.gov/nuccore/EF219377.
Hu et al., "Metabolic phenotyping of the cyanobacterium Synechocystis 6803 engineered for production of alkanes and free fatty acids," Applied Energy, Feb. 2013, vol. 102, pp. 850-859.
International Preliminary Report on Patentability issued on PCT/US2009/069356, dated Jun. 29, 2011, 9 pages.
International Preliminary Report on Patentability issued on PCT/US2015/041031, dated Jan. 24, 2017, 15 pages.
International Search Report and Written Opinion for PCT/US2015/041031, dated Oct. 21, 2015, 12 pages.

(56) References Cited

OTHER PUBLICATIONS

Kaiser et al., "Fatty Aldehydes in Cyanobacteria Are a Metabolically Flexible Precursor for a Diversity of Biofuel Products," PLOS ONE, vol. 8, Issue 3, Mar. 11, 2013, pp. 1-11.
Ku et al., "High-level expression of maize phosphoenolpyruvate carboxylase in transgenic rice plants," Nature Biotechnology, vol. 17, Jan. 1999, pp. 76-80.
Labrou, "Random Mutagenesis Methods for In Vitro Directed Enzyme evolution," Current Protein and Peptide Science, Feb. 2010, pp. 91-100.
Liu et al., "Metabolic engineering of fatty acyl-ACP reductase-dependent pathway to improve fatty alcohol production in *Esherichia coli*," Metabolic Engineering, Dec. 12, 2013, vol. 22, pp. 10-21.
Office Action issued on CN Application 201510993452.9, dated Sep. 13, 2018, 22 pages with translation.
Office Action Issued on EP Application 09803969.6, dated Dec. 8, 2017, 4 pages.
Office Action issued on ID Application W00201102255, dated Jan. 17, 2019, 3 pages with translation.
Office Action on AU Application No. 2013243601, dated Oct. 5, 2017, 5 pages.
Office Action on CA Application 2747516, dated Mar. 27, 2017, 4 pages.
Office Action on CN 201380058918.5, dated Mar. 13, 2018, 9 pages with translation.
Office Action on CN Application No. 201380026304.9, dated Jan. 5, 2018, 18 pages with translation.
Office Action on CN Application No. 201380026304.9, dated Sep. 9, 2016, 9 pages with translation.
Office Action on CN Application No. 201380026304.9, dated Oct. 26, 2018, 12 pages with translation.
Office Action on CO Application NC2017/0000367, dated Apr. 27, 2018, 18 pages (with English translation).
Office Action on EP 17168184.4, dated Nov. 16, 2018, 6 pages.
Office Action on EP Application 19161705.9, dated Apr. 4, 2019, 1 page.
Office Action on ID Application No. P00201406815, dated Apr. 12, 2018, 3 pages with translation.
Office Action on JP 2015-531914, dated Oct. 26, 2017, 11 pages with translation.
Office Action on JP Application 2015-504687, dated Nov. 9, 2017, 9 pages with translation.
Office Action on KR 10-2017-7026945, dated Apr. 24, 2018, 10 pages with translation.
Office Action on MY PI2014002838, dated Mar. 30, 2018, 3 pages.
Phung et al., "unknown [Synechococcus elongates PCC 7942]" GenBank amino acid sequence database entry, accession No. AAB82038, Oct. 28, 1997, 1 page.
Reetz et al., "Iterative Saturation Mutagenesis Accelerates Laboratory Evolution of Enzyme Stereoselectivity: Rigorous Comparison with Traditional Methods," J. Am. Chem. Soc., Jul. 7, 2010, vol. 132, pp. 9144-9152.
Rudd, K.E.,"Multifunctional acyl-CoA thioesterase I an protease I and lysophospholipase L1 [*Escherichia coli* str. K-12 substr. MG1655]", GenBank Database, May 17, 2008, Accession No. NP_415027, 1-14.
Schirmer et al., "Microbial Biosynthesis of Alkanes", Science, vol. 329, Jul. 30, 2010, pp. 559-562.
Tracewell et al., "Directed enzyme evolution: climbing fitness peaks one amino acid at a time," Curr. Opinion in Chemical Biol., vol. 13, No. 1, Feb. 2009, pp. 3-9.
Xu et al., "Cloning and characterization of an acyl-CoA-dependent diacyglycerol acyltransferase 1 (DGAT1) gene from Tropaeolum majus, and a study of the functional motifs of the DGAT protein using site-directed mutagenesis to modify enzyme activity and oil content" Plant Biotechnol. J., Sep. 1, 2008, vol. 6, pp. 799-818.
Yang et al., "Biosynthesis of Polylactic Acid and Its Copolymers Using Evolved Propionate CoA Transferase and PHA Synthase," Biotech. and Bioengineering, vol. 105, No. 1, Jan. 1, 2010, pp. 150-160.
Yao et al., "Improved production of fatty alcohols in cyanobacteria by metabolic engineering," Biotechnology for Biofuels, vol. 7, Jun. 18, 2014, pp. 1-9.
Examination Report No. 2 in AU Patent Application No. 2015289430 dated Feb. 10, 2020, 3 pages.
Office Action in MX Patent Application No. MX/a/2017/000669 dated Jan. 28, 2020 (with English translation) (8 pages).
Office Action in MX Patent Application No. MX/a/2017/000669 dated Jan. 30, 2020 (with English translation) (3 pages).
Substantive Examination Adverse Report on MY PI2017000065 dated Feb. 24, 2020, 2 pages.

\* cited by examiner

SEQUENCE LISTING

```
<160> NUMBER OF SEQ ID NOS: 8

<210> SEQ ID NO 1
<211> LENGTH: 342
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic AAR Variant polypeptide"

<400> SEQUENCE: 1

Met Ala Phe Gly Leu Ile Gly His Ala Thr Ser Leu Glu Gln Ala Arg
1               5                   10                  15

Asp Val Trp Arg Arg Leu Gly Tyr Asp Glu Tyr Ala Asp Gln Gly Leu
                20                  25                  30

Glu Phe Trp Ser Ser Ala Pro Pro Gln Ile Val Asp Glu Ile Thr Val
            35                  40                  45

Thr Ser Ala Thr Gly Lys Val Ile His Gly Arg Tyr Ile Glu Ser Gly
        50                  55                  60

Phe Leu Pro Glu Met Leu Ala Ala Arg Arg Phe Lys Thr Ala Thr Arg
65                  70                  75                  80

Lys Val Leu Asn Ala Met Ser His Ala Gln Lys His Gly Ile Asp Ile
                85                  90                  95

Ser Ala Leu Gly Gly Phe Thr Ser Ile Ile Phe Glu Asn Phe Asp Leu
                100                 105                 110

Ala Lys Leu Arg Gln Val Arg Asp Thr Thr Leu Glu Phe Glu Arg Phe
            115                 120                 125

Thr Thr Gly Asn Thr His Thr Ala Tyr Val Ile Cys Arg Gln Val Glu
```

```
            130               135               140
Ala Ala Ala Lys Thr Leu Gly Ile Asp Ile Ala Gln Ala Thr Val Ala
145                 150                 155                 160

Val Val Gly Ala Thr Gly Asp Ile Gly Ser Ala Val Cys Arg Trp Leu
                165                 170                 175

Asp Leu Lys Leu Gly Val Gly Asp Leu Ile Leu Thr Ala Arg Asn Gln
            180                 185                 190

Glu Arg Leu Asp Asn Leu Gln Ala Glu Leu Gly Arg Gly Lys Ile Leu
        195                 200                 205

Pro Leu Glu Ala Ala Leu Pro Glu Ala Asp Phe Ile Val Trp Val Ala
    210                 215                 220

Ser Met Pro Gln Gly Val Val Ile Asp Pro Ala Thr Leu Lys Gln Pro
225                 230                 235                 240

Cys Val Leu Ile Asp Gly Gly Tyr Pro Lys Asn Leu Gly Ser Lys Val
                245                 250                 255

Gln Gly Glu Gly Ile Tyr Val Leu Asn Gly Gly Val Val Glu His Cys
            260                 265                 270

Phe Asp Ile Asp Trp Gln Ile Met Ser Leu Ala Glu Met Ala Arg Pro
        275                 280                 285

Glu Arg Gln Met Phe Ala Cys Phe Ala Glu Ala Met Leu Leu Glu Phe
    290                 295                 300

Glu Gly Trp His Thr Asn Phe Ser Trp Gly Arg Asn Gln Ile Thr Ile
305                 310                 315                 320

Glu Lys Met Glu Ala Ile Gly Glu Ala Ser Val Arg His Gly Phe Gln
                325                 330                 335

Pro Leu Ala Leu Ala Ile
            340

<210> SEQ ID NO 2
<211> LENGTH: 1029
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic AAR Variant polynucleotide"

<400> SEQUENCE: 2
atggcattcg gtcttatcgg tcatgcaacc agtttggagc aggcccgcga cgtttggcgc      60
aggctgggct acgacgaata cgccgatcaa ggattggagt tttggagtag cgctcctcct     120
caaatcgttg atgaaatcac agtcaccagt gccacaggca aggtgattca cggtcgctac     180
atcgaatcgg ggttcttgcc ggaaatgctg gcggcgcgcc gcttcaaaac agcaacgcgc     240
aaagttctca atgccatgtc ccatgcccaa aaacacggca tcgacatctc ggccttgggg     300
ggctttacct cgattatttt cgagaatttc gatttggcca agttgcggca agtgcgcgac     360
actaccttgg agtttgaacg gttcaccacc ggcaatactc acacggccta cgtaatctgt     420
agacaggtgg aagccgctgc taaaacgctg gcatcgaca ttgcgcaagc gacagtagcg     480
gttgtcggcg cgactggcga tatcggtagc gctgtctgcc gctggctcga cctcaaactg     540
ggtgtcggtg atttgatcct gacggcgcgc aatcaggagc gtttggataa cctgcaggct     600
gaactcggcc ggggcaagat tctgcccttg aagccgctct gccggaagc tgactttatc     660 gtgtgggtcg ccagtatgcc tcagggcgta gtgatcgacc cagcaaccct gaagcaaccc     720
tgcgtcctaa tcgacggggg ctaccccaaa aacttgggca gcaaagtcca aggtgagggc     780
```

```
atctatgtcc tcaatggcgg ggtagttgaa cattgcttcg acatcgactg gcagatcatg    840
tccttggcag agatggcgcg gcccgagcgc cagatgtttg cctgctttgc cgaggcgatg    900
ctcttggaat tgaaggctg gcatactaac ttctcctggg gccgcaacca aatcacgatc    960
gagaagatgg aagcgatcgg tgaggcatcg gtgcgccacg gcttccaacc cttggcattg   1020
gcaatttga                                                           1029
```

<210> SEQ ID NO 3
<211> LENGTH: 1174
<212> TYPE: PRT
<213> ORGANISM: Artificial Sequence
<220> FEATURE:
<221> NAME/KEY: source
<223> OTHER INFORMATION: /note="Description of Artificial Sequence: Synthetic CAR Variant polypeptide"

<400> SEQUENCE: 3

```
Met Gly Thr Ser Asp Val His Asp Ala Thr Asp Gly Val Thr Glu Thr
1               5                   10                  15

Ala Leu Arg Asp Arg Gln Arg Thr Arg Arg Ile Ala Glu Leu Tyr Ala
                20                  25                  30

Thr Asp Pro Glu Phe Ala Ala Ala Ala Pro Leu Pro Ala Val Val Asp
            35                  40                  45

Ala Ala His Lys Pro Gly Leu Arg Leu Ala Glu Ile Leu Gln Thr Leu
        50                  55                  60

Phe Thr Gly Tyr Gly Asp Arg Pro Ala Leu Gly Tyr Arg Ala Arg Glu
65                  70                  75                  80

Leu Ala Thr Asp Glu Gly Gly Arg Thr Val Thr Arg Leu Leu Pro Arg
                85                  90                  95

Phe Asp Thr Leu Thr Tyr Ala Gln Val Trp Ser Arg Val Gln Ala Val
            100                 105                 110

Ala Ala Ala Leu Arg His Asn Phe Ala Gln Pro Ile Tyr Pro Gly Asp
        115                 120                 125

Ala Val Ala Thr Ile Gly Phe Ala Ser Pro Asp Tyr Leu Thr Leu Asp
    130                 135                 140

Leu Val Cys Ala Tyr Leu Gly Leu Val Ser Val Pro Leu Gln His Asn
145                 150                 155                 160

Ala Pro Val Ser Arg Leu Ala Pro Ile Leu Ala Glu Val Glu Pro Arg
                165                 170                 175

Ile Leu Thr Val Ser Ala Glu Tyr Leu Asp Leu Ala Val Glu Ser Val
            180                 185                 190

Arg Asp Val Asn Ser Val Ser Gln Leu Val Val Phe Asp His His Pro
        195                 200                 205

Glu Val Asp Asp His Arg Asp Ala Leu Ala Arg Ala Arg Glu Gln Leu
    210                 215                 220

Ala Gly Lys Gly Ile Ala Val Thr Thr Leu Asp Ala Ile Ala Asp Glu
225                 230                 235                 240

Gly Ala Gly Leu Pro Ala Glu Pro Ile Tyr Thr Ala Asp His Asp Gln
                245                 250                 255

Arg Leu Ala Met Ile Leu Tyr Thr Ser Gly Ser Thr Gly Ala Pro Lys
            260                 265                 270

Gly Ala Met Tyr Thr Glu Ala Met Val Ala Arg Leu Trp Thr Met Ser
        275                 280                 285

Gly Ile Thr Gly Asp Pro Thr Pro Val Ile Asn Val Asn Phe Met Pro
    290                 295                 300
```

```
Leu Asn His Leu Gly Gly Arg Ile Pro Ile Ser Thr Ala Val Gln Asn
305                 310                 315                 320

Gly Gly Thr Ser Tyr Phe Val Pro Glu Ser Asp Met Ser Thr Leu Phe
            325                 330                 335

Glu Asp Leu Ala Leu Val Arg Pro Thr Glu Leu Gly Leu Val Pro Arg
            340                 345                 350

Val Ala Asp Met Leu Tyr Gln His His Leu Ala Thr Val Asp Arg Leu
            355                 360                 365

Val Thr Gln Gly Ala Asp Glu Leu Thr Ala Glu Lys Gln Ala Gly Ala
370                 375                 380

Glu Leu Arg Glu Gln Val Leu Gly Gly Arg Val Ile Thr Gly Phe Val
385                 390                 395                 400

Ser Thr Ala Pro Leu Ala Ala Glu Met Arg Ala Phe Leu Asp Ile Thr
            405                 410                 415

Leu Gly Ala His Ile Val Asp Gly Tyr Gly Leu Thr Glu Thr Gly Ala
            420                 425                 430

Val Thr Arg Asp Gly Val Ile Val Arg Pro Val Ile Asp Tyr Lys
            435                 440                 445

Leu Ile Asp Val Pro Glu Leu Gly Tyr Phe Ser Thr Asp Lys Pro Tyr
450                 455                 460

Pro Arg Gly Glu Leu Leu Val Arg Ser Ile Thr Leu Thr Pro Gly Tyr
465                 470                 475                 480

Tyr Lys Arg Pro Glu Val Thr Ala Ser Val Phe Asp Arg Asp Gly Tyr
            485                 490                 495

Tyr His Thr Gly Asp Val Met Ala Glu Thr Ala Pro Asp His Leu Val
            500                 505                 510

Tyr Val Asp Arg Arg Asn Asn Val Leu Lys Leu Ala Gln Gly Glu Phe
            515                 520                 525

Val Ala Val Ala Asn Leu Glu Ser Val Phe Ser Gly Ala Ala Leu Val
            530                 535                 540

Arg Gln Ile Phe Val Tyr Gly Asn Ser Glu Arg Ser Phe Leu Leu Ala
545                 550                 555                 560

Val Val Val Pro Thr Pro Glu Ala Leu Glu Gln Tyr Asp Pro Ala Ala
            565                 570                 575

Leu Lys Ala Ala Leu Ala Asp Ser Leu Gln Arg Thr Ala Arg Asp Ala
            580                 585                 590

Glu Leu Gln Ser Tyr Glu Val Pro Ala Asp Phe Ile Val Glu Thr Glu
            595                 600                 605

Pro Phe Ser Ala Ala Asn Gly Leu Leu Ser Gly Val Gly Lys Leu Leu
            610                 615                 620

Arg Pro Asn Leu Lys Asp Arg Tyr Gly Gln Arg Leu Glu Gln Met Tyr
625                 630                 635                 640

Ala Asp Ile Ala Ala Thr Gln Ala Asn Gln Leu Arg Glu Leu Arg Arg
            645                 650                 655

Ala Ala Ala Thr Gln Pro Val Ile Asp Thr Leu Thr Gln Ala Ala Ala
            660                 665                 670

Thr Ile Leu Gly Thr Gly Ser Glu Val Ala Ser Asp Ala His Phe Thr
            675                 680                 685

Asp Leu Gly Gly Asp Ser Leu Ser Ala Leu Thr Leu Ser Asn Leu Leu
            690                 695                 700

Ser Asp Phe Phe Gly Phe Glu Val Pro Val Gly Thr Ile Val Asn Pro
705                 710                 715                 720

Ala Thr Asn Leu Ala Gln Leu Ala Gln His Ile Glu Ala Gln Arg Thr
```

```
                        725                 730                 735
Ala Gly Asp Arg Arg Pro Ser Phe Thr Thr Val His Gly Ala Asp Ala
                    740                 745                 750

Thr Glu Ile Arg Ala Ser Glu Leu Thr Leu Asp Lys Phe Ile Asp Ala
                755                 760                 765

Glu Thr Leu Arg Ala Ala Pro Gly Leu Pro Lys Val Thr Thr Glu Pro
            770                 775                 780

Arg Thr Val Leu Leu Ser Gly Ala Asn Gly Trp Leu Gly Arg Phe Leu
785                 790                 795                 800

Thr Leu Gln Trp Leu Glu Arg Leu Ala Pro Val Gly Gly Thr Leu Ile
                805                 810                 815

Thr Ile Val Arg Gly Arg Asp Asp Ala Ala Ala Cys Ala Arg Leu Thr
                820                 825                 830

Gln Ala Tyr Asp Thr Asp Pro Glu Leu Ser Arg Arg Phe Ala Glu Leu
                835                 840                 845

Ala Asp Arg His Leu Arg Val Val Ala Gly Asp Ile Gly Asp Gln Asn
850                 855                 860

Leu Gly Leu Thr Pro Glu Leu Trp His Arg Leu Ala Ala Glu Val Asp
865                 870                 875                 880

Leu Val Val His Pro Ala Ala Leu Val Asn His Val Leu Pro Tyr Arg
                885                 890                 895

Gln Leu Phe Gly Pro Asn Val Val Gly Thr Ala Glu Val Ile Lys Leu
                900                 905                 910

Ala Leu Thr Glu Arg Ile Lys Pro Val Thr Tyr Leu Ser Thr Ala Lys
                915                 920                 925

Val Ala Met Gly Ile Pro Asp Phe Glu Glu Asp Gly Asp Ile Arg Thr
            930                 935                 940

Val Ser Pro Val Arg Pro Leu Asp Gly Gly Tyr Ala Asn Gly Tyr Gly
945                 950                 955                 960

Asn Ser Lys Trp Ala Gly Glu Val Leu Leu Arg Glu Ala His Asp Leu
                965                 970                 975

Cys Gly Leu Pro Val Ala Thr Phe Arg Ser Asp Met Ile Leu Ala His
                980                 985                 990

Pro Arg Tyr Arg Gly Gln Val Asn Val Pro Asp Met Phe Thr Arg Leu
            995                1000                1005

Leu Leu Ser Leu Leu Ile Thr Gly Val Ala Pro Arg Ser Phe Tyr
        1010                1015                1020

Ile Gly Asp Gly Glu Arg Pro Arg Ala His Tyr Pro Gly Leu Thr
        1025                1030                1035

Val Asp Phe Val Ala Glu Ala Val Thr Thr Leu Gly Ala Gln Gln
        1040                1045                1050

Arg Glu Gly Tyr Val Ser Tyr Asp Val Met Asn Pro His Asp Asp
        1055                1060                1065

Gly Ile Ser Leu Asp Val Phe Val Asp Trp Leu Ile Arg Ala Gly
        1070                1075                1080

His Pro Ile Asp Arg Val Asp Asp Tyr Asp Asp Trp Val Arg Arg
        1085                1090                1095

Phe Glu Thr Ala Leu Thr Ala Leu Pro Glu Lys Arg Arg Ala Gln
        1100                1105                1110

Thr Val Leu Pro Leu Leu His Ala Phe Arg Ala Pro Gln Ala Pro
        1115                1120                1125

Leu Arg Gly Ala Pro Glu Pro Thr Glu Val Phe His Ala Ala Val
        1130                1135                1140
```

```
Arg Thr Ala Lys Val Gly Pro Gly Asp Ile Pro His Leu Asp Glu
        1145                1150                1155

Ala Leu Ile Asp Lys Tyr Ile Arg Asp Leu Arg Glu Phe Gly Leu
    1160                1165                1170

Ile
```

<210> SEQ ID NO 4
<211> LENGTH: 3525
<212> TYPE: DNA
<213> ORGANISM: Artificial Sequence
<220> FEATURE:
<221> NAME/KEY: source
<223> OTHER INFORMATION: /note="Description of Artificial Sequence: Synthetic CAR Variant (carB12) polynucleotide"

<400> SEQUENCE: 4

```
atgggcacga gcgatgttca cgacgcgacc gacggcgtta ccgagactgc actgcgtgat      60
cgccagcgca ctcgtcgtat tgcagaactg tacgcaacgg acccagagtt cgcagcagca     120
gctcctctgc cggccgttgt cgatgcggcg cacaaaccgg gcctgcgtct ggcggaaatc     180
ctgcagaccc tgttcaccgg ctacggcgat cgtccggcgc tgggctatcg tgcacgtgag     240
ctggcgacgg acgaaggcgg tcgtacggtc acgcgtctgc tgccgcgctt cgataccctg     300
acctatgcac aggtgtggag ccgtgttcaa gcagtggctg cagcgttgcg tcacaatttc     360
gcacaaccga tttacccggg cgacgcggtc gcgactatcg gctttgcgag cccggactat     420
ttgacgctgg atctggtgtg cgcgtatctg ggcctggtca gcgttccttt gcagcataac     480
gctccggtgt ctcgcctggc cccgattctg gccgaggtgg aaccgcgtat tctgacggtg     540
agcgcagaat acctggacct ggcggttgaa tccgtccgtg atgtgaactc cgtcagccag     600
ctggttgttt tcgaccatca tccggaagtg gacgatcacc gtgacgcact ggctcgcgca     660
cgcgagcagc tggccggcaa aggtatcgca gttacgaccc tggatgcgat cgcagacgaa     720
ggcgcaggtt tgccggctga gccgatttac acggcggatc acgatcagcg tctggccatg     780
attctgtata ccagcggctc tacgggtgct ccgaaaggcg cgatgtacac cgaagcgatg     840
gtggctcgcc tgtggactat gagcgggatc acgggcgacc cgaccccggt tatcaacgtg     900
aacttcatgc cgctgaacca tctgggcggt cgtatcccga ttagcaccgc cgtgcagaat     960
ggcggtacca gctacttcgt tccggaaagc gacatgagca cgctgtttga ggatctggcc    1020
ctggtccgcc ctaccgaact gggtctggtg ccgcgtgttg cggacatgct gtaccagcat    1080
catctggcga ccgtggatcg cctggtgacc cagggcgcgg acgaactgac tgcggaaaag    1140
caggccggtg cggaactgcg tgaacaggtc ttgggcggtc gtgttatcac cggttttgtt    1200
tccaccgcgc cgttggcggc agagatgcgt gcttttctgg atatcacctt gggtgcacac    1260
atcgttgacg gttacggtct gaccgaaacc ggtgcggtca cccgtgatgg tgtgattgtt    1320
cgtcctccgg tcattgatta caagctgatc gatgtgccgg agctgggtta cttctccacc    1380
gacaaaccgt acccgcgtgg cgagctgctg gttcgtagca tcacgttgac tccgggttac    1440
tacaagcgcc agaagtcac cgcgtccgtt ttcgatcgcg acggctatta ccacaccggc    1500
gacgtgatgc agaaaccgc gccagaccac ctggtgtatg tggaccgccg caacaatgtt    1560
ctgaagctgg cgcaaggtga atttgtcgcc gtggctaacc tggagtccgt tttcagcggc    1620
gctgctctgg tccgccagat tttcgtgtat ggtaacagcg agcgcagctt ctgttggct    1680
gttgttgtcc ctacccgga ggcgctggag caatacgacc ctgccgcatt gaaagcagcc    1740
```

```
ctggcggatt cgctgcagcg tacggcgcgt gatgccgagc tgcagagcta tgaagtgccg    1800
gcggacttca ttgttgagac tgagcctttt agcgctgcga acggtctgct gagcggtgtt    1860
ggcaagttgc tgcgtccgaa tttgaaggat cgctacggtc agcgtttgga gcagatgtac    1920
gcggacatcg cggctacgca ggcgaaccaa ttgcgtgagc tgcgtcgcgc tgcggctact    1980
caaccggtga tcgacacgct gacgcaagct gcggcgacca tcctgggtac cggcagcgag    2040
gttgcaagcg acgcacactt tactgatttg ggcggtgatt ctctgagcgc gctgacgttg    2100
agcaacttgc tgtctgactt cttttggcttt gaagtcccgg ttggcacgat tgttaaccca    2160
gcgactaatc tggcacagct ggcgcaacat atcgaggcgc agcgcacggc gggtgaccgc    2220
cgtccatcct ttacgacggt ccacggtgcg gatgctacgg aaatccgtgc aagcgaactg    2280
actctggaca aattcatcga cgctgagact ctgcgcgcag cacctggttt gccgaaggtt    2340
acgactgagc cgcgtacggt cctgttgagc ggtgccaatg ttggttggg ccgcttcctg    2400
accctgcagt ggctgaaacg tttggcaccg gttggcggta ccctgatcac cattgtgcgc    2460
ggtcgtgacg atgcagcggc ctgtgcacgc ttgactcagg cttacgatac ggacccagag    2520
ctgtcccgcc gcttcgctga gttggcggat cgccacttgc gtgtggtggc aggtgatatc    2580
ggcgatcaga atctgggcct gaccccggaga ctgtggcacc gtctggcagc agaggtcgat    2640
ctggtcgttc atccagcggc cctggtcaac cacgtcctgc cgtaccgcca gctgtttggt    2700
ccgaatgttg ttggcaccgc cgaagttatc aagttggctc tgaccgagcg catcaagcct    2760
gttacctacc tgtccacggc gaaggtcgcg atgggtattc ctgattttga ggaggacggt    2820
gacattcgta ccgtcagccc ggttcgtccg ctggatggtg ctatgcaaa tggctatggc    2880
aacagcaagt gggctggcga ggtgctgctg cgcgaggcac atgacctgtg tggcctgccg    2940
gttgcgacgt tcgtagcga catgattctg gcccacccgc gctaccgtgg ccaagtgaat    3000
gtgccggaca tgttcacccg tctgctgctg tccctgctga tcacgggtgt ggcaccgcgt    3060
tccttctaca ttggtgatgg cgagcgtccg cgtgcacact accgggcct gaccgtcgat    3120
tttgttgcgg aagcggttac taccctgggt gctcagcaac gtgagggtta tgtctcgtat    3180
gacgttatga atccgcacga tgacggtatt agcttggatg tctttgtgga ctggctgatt    3240
cgtgcgggcc acccaattga ccgtgttgac gactatgatg actgggtgcg tcgttttgaa    3300
accgcgttga ccgccttgcc ggagaaacgt cgtgcgcaga ccgttctgcc gctgctgcat    3360
gcctttcgcg cgccacaggc gccgttgcgt ggcgcccctg aaccgaccga agtgtttcat    3420
gcagcggtgc gtaccgctaa agtcggtccg ggtgatattc gcacctgga tgaagccctg    3480
atcgacaagt acatccgtga cctgcgcgag ttcggtctga tttag               3525
```

<210> SEQ ID NO 5
<211> LENGTH: 1173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic CAR Variant (carB2) polypeptide"

<400> SEQUENCE: 5

```
Met Thr Ser Asp Val His Asp Ala Thr Asp Gly Val Thr Glu Thr Ala
1               5                   10                  15

Leu Asp Asp Arg Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
```

```
                35                  40                  45
Ala His Lys Pro Gly Leu Arg Leu Ala Glu Ile Leu Gln Thr Leu Phe
 50                  55                  60

Thr Gly Tyr Gly Asp Arg Pro Ala Leu Gly Tyr Arg Ala Arg Glu Leu
65                  70                  75                  80

Ala Thr Asp Glu Gly Arg Thr Val Thr Arg Leu Leu Pro Arg Phe
                85                  90                  95

Asp Thr Leu Thr Tyr Ala Gln Val Trp Ser Arg Val Gln Ala Val Ala
                100                 105                 110

Ala Ala Leu Arg His Asn Phe Ala Gln Pro Ile Tyr Pro Gly Asp Ala
            115                 120                 125

Val Ala Thr Ile Gly Phe Ala Ser Pro Asp Tyr Leu Thr Leu Asp Leu
            130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
                180                 185                 190

Asp Val Asn Ser Val Ser Gln Leu Val Val Phe Asp His His Pro Glu
            195                 200                 205

Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
                260                 265                 270

Ala Met Tyr Thr Glu Ala Met Val Ala Arg Leu Trp Thr Met Ser Gly
            275                 280                 285

Ile Thr Gly Asp Pro Thr Pro Val Ile Asn Val Asn Phe Met Pro Leu
            290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
            355                 360                 365

Thr Gln Gly Ala Asp Glu Leu Thr Ala Glu Lys Gln Ala Gly Ala Glu
            370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
                420                 425                 430

Thr Arg Asp Gly Val Ile Val Arg Pro Pro Val Ile Asp Tyr Lys Leu
            435                 440                 445

Ile Asp Val Pro Glu Leu Gly Tyr Phe Ser Thr Asp Lys Pro Tyr Pro
450                 455                 460
```

```
Arg Gly Glu Leu Leu Val Arg Ser Ile Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ser Val Phe Ser Gly Ala Ala Leu Val Arg
    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
        595                 600                 605

Phe Ser Ala Ala Asn Gly Leu Leu Ser Gly Val Gly Lys Leu Leu Arg
610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
        675                 680                 685

Leu Gly Gly Asp Ser Leu Ser Ala Leu Thr Leu Ser Asn Leu Leu Ser
690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
        835                 840                 845

Asp Arg His Leu Arg Val Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880
```

| | | | | | | | | | | | |
|---|---|---|---|---|---|---|---|---|---|---|---|
|Val|Val|His|Pro|Ala|Ala|Leu|Val|Asn|His|Val|Leu|Pro|Tyr|Arg|Gln|
| | | | |885| | | | |890| | | | |895| |

Leu Phe Gly Pro Asn Val Val Gly Thr Ala Glu Val Ile Lys Leu Ala
        900                 905                 910

Leu Thr Glu Arg Ile Lys Pro Val Thr Tyr Leu Ser Thr Val Ser Val
        915                 920                 925

Ala Met Gly Ile Pro Asp Phe Glu Glu Asp Gly Asp Ile Arg Thr Val
        930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
        965                 970                 975

Gly Leu Pro Val Ala Thr Phe Arg Ser Asp Met Ile Leu Ala His Pro
        980                 985                 990

Arg Tyr Arg Gly Gln Val Asn Val Pro Asp Met Phe Thr Arg Leu Leu
        995                 1000                1005

Leu Ser Leu Leu Ile Thr Gly Val Ala Pro Arg Ser Phe Tyr Ile
        1010                1015                1020

Gly Asp Gly Glu Arg Pro Arg Ala His Tyr Pro Gly Leu Thr Val
        1025                1030                1035

Asp Phe Val Ala Glu Ala Val Thr Thr Leu Gly Ala Gln Gln Arg
        1040                1045                1050

Glu Gly Tyr Val Ser Tyr Asp Val Met Asn Pro His Asp Asp Gly
        1055                1060                1065

Ile Ser Leu Asp Val Phe Val Asp Trp Leu Ile Arg Ala Gly His
        1070                1075                1080

Pro Ile Asp Arg Val Asp Tyr Asp Asp Trp Val Arg Arg Phe
        1085                1090                1095

Glu Thr Ala Leu Thr Ala Leu Pro Glu Lys Arg Arg Ala Gln Thr
        1100                1105                1110

Val Leu Pro Leu Leu His Ala Phe Arg Ala Pro Gln Ala Pro Leu
        1115                1120                1125

Arg Gly Ala Pro Glu Pro Thr Glu Val Phe His Ala Ala Val Arg
        1130                1135                1140

Thr Ala Lys Val Gly Pro Gly Asp Ile Pro His Leu Asp Glu Ala
        1145                1150                1155

Leu Ile Asp Lys Tyr Ile Arg Asp Leu Arg Glu Phe Gly Leu Ile
        1160                1165                1170

<210> SEQ ID NO 6
<211> LENGTH: 3525
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic CAR Variant (carB2) polynucleotide"

<400> SEQUENCE: 6
atgggcacga gcgatgttca cgacgcgacc gacggcgtta ccgagactgc actggatgat    60
cgccagagca ctcgtcgtat tgcagaactg tacgcaacgg acccagagtt cgcagcagca   120
gctcctctgc cggccgttgt cgatgcggcg cacaaaccgg gcctgcgtct ggcggaaatc   180
ctgcagaccc tgttcaccgg ctacggcgat cgtccggcgc tgggctatcg tgcacgtgag   240
ctggcgacgg acgaaggcgg tcgtacggtc acgcgtctgc tgccgcgctt cgataccctg   300

-continued

```
acctatgcac aggtgtggag ccgtgttcaa gcagtggctg cagcgttgcg tcacaatttc      360
gcacaaccga tttacccggg cgacgcggtc gcgactatcg gctttgcgag cccggactat      420
ttgacgctgg atctggtgtg cgcgtatctg ggcctggtca gcgttccttt gcagcataac      480
gctccggtgt ctcgcctggc cccgattctg gccgaggtgg aaccgcgtat tctgacggtg      540
agcgcagaat acctggacct ggcggttgaa tccgtccgtg atgtgaactc cgtcagccag      600
ctggttgttt tcgaccatca tccggaagtg gacgatcacc gtgacgcact ggctcgcgca      660
cgcgagcagc tggccggcaa aggtatcgca gttacgaccc tggatgcgat cgcagacgaa      720
ggcgcaggtt tgccggctga gccgatttac acggcggatc acgatcagcg tctggccatg      780
attctgtata ccagcggctc tacgggtgct ccgaaaggcg cgatgtacac cgaagcgatg      840
gtggctcgcc tgtggactat gagcgggatc acgggcgacc cgaccccggt tatcaacgtg      900
aacttcatgc cgctgaacca tctgggcggt cgtatcccga ttagcaccgc cgtgcagaat      960
ggcggtacca gctacttcgt tccggaaagc gacatgagca cgctgtttga ggatctggcc     1020
ctggtccgcc ctaccgaact gggtctggtg ccgcgtgttg cggacatgct gtaccagcat     1080
catctggcga ccgtggatcg cctggtgacc cagggcgcgg acgaactgac tgcggaaaag     1140
caggccggtg cggaactgcg tgaacaggtc ttgggcggtc gtgttatcac cggttttgtt     1200
tccaccgcgc cgttggcggc agagatgcgt gctttctgg atatcacctt gggtgcacac     1260
atcgttgacg gttacggtct gaccgaaacc ggtgcggtca cccgtgatgg tgtgattgtt     1320
cgtcctccgg tcattgatta caagctgatc gatgtgccgg agctgggtta cttctccacc     1380
gacaaaccgt acccgcgtgg cgagctgctg gttcgtagca tcacgttgac tccgggttac     1440
tacaagcgcc cagaagtcac cgcgtccgtt ttcgatcgcg acggctatta ccacaccggc     1500
gacgtgatgg cagaaaccgc gccagaccac ctggtgtatg tggaccgccg caacaatgtt     1560
ctgaagctgg cgcaaggtga atttgtcgcc gtggctaacc tggagtccgt tttcagcggc     1620
gctgctctgg tccgccagat tttcgtgtat ggtaacagcg agcgcagctt tctgttggct     1680
gttgttgtcc ctaccccgga ggcgctggag caatacgacc ctgccgcatt gaaagcagcc     1740
ctggcggatt cgctgcagcg tacggcgcgt gatgccgagc tgcagagcta tgaagtgccg     1800
gcggacttca ttgttgagac tgagccttt agcgctgcga acggtctgct gagcggtgtt     1860
ggcaagttgc tgcgtccgaa tttgaaggat cgctacggtc agcgtttgga gcagatgtac     1920
gcggacatcg cggctacgca ggcgaaccaa ttgcgtgagc tgcgtcgcgc tgcggctact     1980
caaccggtga tcgacacgct gacgcaagct cgggcgacca tcctgggtac cggcagcgag     2040
gttgcaagcg acgcacactt tactgatttg ggcggtgatt ctctgagcgc gctgacgttg     2100
agcaacttgc tgtctgactt cttggctttt gaagtcccgg ttggcacgat tgttaaccca     2160
gcgactaatc tggcacagct ggcgcaacat atcgaggcgc agcgcacggc gggtgaccgc     2220
cgtccatcct ttacgacggt ccacggtgcg gatgctacgg aaatccgtgc aagcgaactg     2280
actctggaca aattcatcga cgctgagact ctgcgcgcag cacctggttt gccgaaggtt     2340
acgactgagc cgcgtacggt cctgttgagc ggtgccaatg ttggttggg ccgcttcctg     2400 accctgcagt ggctggaacg tttgcaccg gttggcggta ccctgatcac cattgtgcgc     2460
ggtcgtgacg atgcagcggc ccgcgcacgc ttgactcagg cttacgatac ggacccagag     2520
ctgtcccgcc gcttcgctga gttggcggat cgccacttgc gtgtggtggc aggtgatatc     2580
ggcgatccga atctgggcct gaccccggag atttggcacc gtctggcagc agaggtcgat     2640
ctggtcgttc atccagcggc cctggtcaac cacgtcctgc cgtaccgcca gctgtttggt     2700
```

```
ccgaatgttg ttggcaccgc cgaagttatc aagttggctc tgaccgagcg catcaagcct   2760
gttacctacc tgtccacggt tagcgtcgcg atgggtattc ctgattttga ggaggacggt   2820
gacattcgta ccgtcagccc ggttcgtccg ctggatggtg gctatgcaaa tggctatggc   2880
aacagcaagt gggctggcga ggtgctgctg cgcgaggcac atgacctgtg tggcctgccg   2940
gttgcgacgt ttcgtagcga catgattctg gcccacccgc gctaccgtgg ccaagtgaat   3000
gtgccggaca tgttcacccg tctgctgctg tccctgctga tcacgggtgt ggcaccgcgt   3060
tccttctaca ttggtgatgg cgagcgtccg cgtgcacact acccgggcct gaccgtcgat   3120
tttgttgcgg aagcggttac taccctgggt gctcagcaac gtgagggtta tgtctcgtat   3180
gacgttatga atccgcacga tgacggtatt agcttggatg tctttgtgga ctggctgatt   3240
cgtgcgggcc acccaattga ccgtgttgac gactatgatg actgggtgcg tcgttttgaa   3300
accgcgttga ccgccttgcc ggagaaacgt cgtgcgcaga ccgttctgcc gctgctgcat   3360
gcctttcgcg cgccacaggc gccgttcgct ggcgcccctg aaccgaccga agtgtttcat   3420
gcagcggtgc gtaccgctaa agtcggtccg ggtgatattc cgcacctgga tgaagccctg   3480
atcgacaagt acatccgtga cctgcgcgag ttcggtctga tttag   3525
```

<210> SEQ ID NO 7
<211> LENGTH: 1174
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic CAR Variant (carB8) polypeptide"

<400> SEQUENCE: 7

```
Met Gly Thr Ser Asp Val His Asp Ala Thr Asp Gly Val Thr Glu Thr
1               5                   10                  15

Ala Leu Asp Asp Arg Gln Arg Thr Arg Arg Ile Ala Glu Leu Tyr Ala
            20                  25                  30

Thr Asp Pro Glu Phe Ala Ala Ala Pro Leu Pro Ala Val Val Asp
        35                  40                  45

Ala Ala His Lys Pro Gly Leu Arg Leu Ala Glu Ile Leu Gln Thr Leu
    50                  55                  60

Phe Thr Gly Tyr Gly Asp Arg Pro Ala Leu Gly Tyr Arg Ala Arg Glu
65                  70                  75                  80

Leu Ala Thr Asp Glu Gly Gly Arg Thr Val Thr Arg Leu Leu Pro Arg
                85                  90                  95

Phe Asp Thr Leu Thr Tyr Ala Gln Val Trp Ser Arg Val Gln Ala Val
            100                 105                 110

Ala Ala Ala Leu Arg His Asn Phe Ala Gln Pro Ile Tyr Pro Gly Asp
        115                 120                 125

Ala Val Ala Thr Ile Gly Phe Ala Ser Pro Asp Tyr Leu Thr Leu Asp
    130                 135                 140

Leu Val Cys Ala Tyr Leu Gly Leu Val Ser Val Pro Leu Gln His Asn
145                 150                 155                 160

Ala Pro Val Ser Arg Leu Ala Pro Ile Leu Ala Glu Val Glu Pro Arg
                165                 170                 175

Ile Leu Thr Val Ser Ala Glu Tyr Leu Asp Leu Ala Val Glu Ser Val
            180                 185                 190

Arg Asp Val Asn Ser Val Ser Gln Leu Val Val Phe Asp His His Pro
        195                 200                 205
```

```
Glu Val Asp Asp His Arg Asp Ala Leu Ala Arg Ala Arg Glu Gln Leu
    210                 215                 220

Ala Gly Lys Gly Ile Ala Val Thr Thr Leu Asp Ala Ile Ala Asp Glu
225                 230                 235                 240

Gly Ala Gly Leu Pro Ala Glu Pro Ile Tyr Thr Ala Asp His Asp Gln
                245                 250                 255

Arg Leu Ala Met Ile Leu Tyr Thr Ser Gly Ser Thr Gly Ala Pro Lys
            260                 265                 270

Gly Ala Met Tyr Thr Glu Ala Met Val Ala Arg Leu Trp Thr Met Ser
        275                 280                 285

Gly Ile Thr Gly Asp Pro Thr Pro Val Ile Asn Val Asn Phe Met Pro
    290                 295                 300

Leu Asn His Leu Gly Gly Arg Ile Pro Ile Ser Thr Ala Val Gln Asn
305                 310                 315                 320

Gly Gly Thr Ser Tyr Phe Val Pro Glu Ser Asp Met Ser Thr Leu Phe
                325                 330                 335

Glu Asp Leu Ala Leu Val Arg Pro Thr Glu Leu Gly Leu Val Pro Arg
            340                 345                 350

Val Ala Asp Met Leu Tyr Gln His His Leu Ala Thr Val Asp Arg Leu
        355                 360                 365

Val Thr Gln Gly Ala Asp Glu Leu Thr Ala Glu Lys Gln Ala Gly Ala
    370                 375                 380

Glu Leu Arg Glu Gln Val Leu Gly Gly Arg Val Ile Thr Gly Phe Val
385                 390                 395                 400

Ser Thr Ala Pro Leu Ala Ala Glu Met Arg Ala Phe Leu Asp Ile Thr
                405                 410                 415

Leu Gly Ala His Ile Val Asp Gly Tyr Gly Leu Thr Glu Thr Gly Ala
            420                 425                 430

Val Thr Arg Asp Gly Val Ile Val Arg Pro Pro Val Ile Asp Tyr Lys
        435                 440                 445

Leu Ile Asp Val Pro Glu Leu Gly Tyr Phe Ser Thr Asp Lys Pro Tyr
    450                 455                 460

Pro Arg Gly Glu Leu Leu Val Arg Ser His Thr Leu Thr Pro Gly Tyr
465                 470                 475                 480

Tyr Lys Arg Pro Glu Val Thr Ala Ser Val Phe Asp Arg Asp Gly Tyr
                485                 490                 495

Tyr His Thr Gly Asp Val Met Ala Glu Thr Ala Pro Asp His Leu Val
            500                 505                 510

Tyr Val Asp Arg Arg Asn Asn Val Leu Lys Leu Ala Gln Gly Glu Phe
        515                 520                 525

Val Ala Val Ala Asn Leu Glu Ser Val Phe Ser Gly Ala Ala Leu Val
    530                 535                 540

Arg Gln Ile Phe Val Tyr Gly Asn Ser Glu Arg Ser Phe Leu Leu Ala
545                 550                 555                 560

Val Val Val Pro Thr Pro Glu Ala Leu Glu Gln Tyr Asp Pro Ala Ala
                565                 570                 575

Leu Lys Ala Ala Leu Ala Asp Ser Leu Gln Arg Thr Ala Arg Asp Ala
            580                 585                 590

Glu Leu Gln Ser Tyr Glu Val Pro Ala Asp Phe Ile Val Glu Thr Glu
        595                 600                 605

Pro Phe Ser Ala Ala Asn Gly Leu Leu Ser Gly Val Gly Lys Leu Leu
    610                 615                 620
```

```
Arg Pro Asn Leu Lys Asp Arg Tyr Gly Gln Arg Leu Glu Gln Met Tyr
625                 630                 635                 640

Ala Asp Ile Ala Ala Thr Gln Ala Asn Gln Leu Arg Glu Leu Arg Arg
            645                 650                 655

Ala Ala Ala Thr Gln Pro Val Ile Asp Thr Leu Thr Gln Ala Ala Ala
            660                 665                 670

Thr Ile Leu Gly Thr Gly Ser Glu Val Ala Ser Asp Ala His Phe Thr
        675                 680                 685

Asp Leu Gly Gly Asp Ser Leu Ser Ala Leu Thr Leu Ser Asn Leu Leu
    690                 695                 700

Ser Asp Phe Phe Gly Phe Glu Val Pro Val Gly Thr Ile Val Asn Pro
705                 710                 715                 720

Ala Thr Asn Leu Ala Gln Leu Ala Gln His Ile Glu Ala Gln Arg Thr
                725                 730                 735

Ala Gly Asp Arg Arg Pro Ser Phe Thr Thr Val His Gly Ala Asp Ala
            740                 745                 750

Thr Glu Ile Arg Ala Ser Glu Leu Thr Leu Asp Lys Phe Ile Asp Ala
        755                 760                 765

Glu Thr Leu Arg Ala Ala Pro Gly Leu Pro Lys Val Thr Thr Glu Pro
770                 775                 780

Arg Thr Val Leu Leu Ser Gly Ala Asn Gly Trp Leu Gly Arg Phe Leu
785                 790                 795                 800

Thr Leu Gln Trp Leu Glu Arg Leu Ala Pro Val Gly Gly Thr Leu Ile
                805                 810                 815

Thr Ile Val Arg Gly Arg Asp Asp Ala Ala Arg Ala Arg Leu Thr
            820                 825                 830

Gln Ala Tyr Asp Thr Asp Pro Glu Leu Ser Arg Arg Phe Ala Glu Leu
        835                 840                 845

Ala Asp Arg His Leu Arg Val Val Ala Gly Asp Ile Gly Asp Pro Asn
850                 855                 860

Leu Gly Leu Thr Pro Glu Ile Trp His Ser Leu Ala Ala Glu Val Asp
865                 870                 875                 880

Leu Val Val His Pro Ala Ala Leu Val Asn His Val Leu Pro Tyr Arg
                885                 890                 895

Gln Leu Phe Gly Pro Asn Val Val Gly Thr Ala Glu Val Ile Lys Leu
            900                 905                 910

Ala Leu Thr Glu Arg Ile Lys Pro Val Thr Tyr Leu Ser Thr Val Gly
        915                 920                 925

Val Ala Arg Gly Ile Pro Asp Phe Glu Glu Asp Gly Asp Ile Arg Thr
930                 935                 940

Val Ser Pro Val Arg Pro Leu Asp Gly Gly Tyr Ala Asn Gly Tyr Gly
945                 950                 955                 960

Asn Ser Lys Trp Ala Gly Glu Val Leu Leu Arg Glu Ala His Asp Leu
                965                 970                 975

Cys Gly Leu Pro Val Ala Thr Phe Arg Ser Asp Met Ile Leu Ala His
            980                 985                 990

Pro Arg Tyr Arg Gly Gln Val Asn Val Pro Asp Met Phe Thr Arg Leu
        995                 1000                1005

Leu Leu Ser Leu Leu Ile Thr Gly Val Ala Pro Arg Ser Phe Tyr
        1010                1015                1020

Ile Gly Asp Gly Glu Arg Pro Arg Ala His Tyr Pro Gly Leu Thr
        1025                1030                1035

Val Asp Phe Val Ala Glu Ala Val Thr Thr Leu Gly Ala Gln Gln
```

```
                         1040                1045                1050
Arg Glu Gly Tyr Val Ser Tyr Asp Val Met Asn Pro His Asp Asp
        1055                1060                1065

Gly Ile Ser Leu Asp Val Phe Val Asp Trp Leu Ile Arg Ala Gly
        1070                1075                1080

His Pro Ile Asp Arg Val Asp Asp Tyr Asp Trp Val Arg Arg
        1085                1090                1095

Phe Glu Thr Ala Leu Thr Ala Leu Pro Glu Lys Arg Arg Ala Gln
        1100                1105                1110

Thr Val Leu Pro Leu Leu His Ala Phe Arg Ala Pro Gln Ala Pro
        1115                1120                1125

Trp Arg Gly Ala Pro Glu Pro Thr Glu Val Phe His Ala Ala Val
        1130                1135                1140

Arg Thr Ala Lys Val Gly Pro Gly Asp Ile Pro His Leu Asp Glu
        1145                1150                1155

Ala Leu Ile Asp Lys Tyr Ile Arg Asp Leu Arg Glu Phe Gly Leu
        1160                1165                1170

Ile

<210> SEQ ID NO 8
<211> LENGTH: 3525
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic CAR Variant (carB8) polynucleotide"

<400> SEQUENCE: 8
atgggcacga gcgatgttca cgacgcgacc gacggcgtta ccgagactgc actggatgat     60
cgccagagga ctcgtcgtat tgcagaactg tacgcaacgg acccagagtt cgcagcagca    120
gctcctctgc cggccgttgt cgatgcgcg cacaaaccgg gcctgcgtct ggcggaaatc    180
ctgcagaccc tgttcaccgg ctacggcgat cgtccggcgc tgggctatcg tgcacgtgag    240
ctggcgacga cgaaggcgg tcgtacggtc acgcgtctgc tgccgcgctt cgatacctg    300 acctatgcac aggtgtggag ccgtgttcaa gcagtggctg cagcgttgcg tcacaattc    360 gcacaaccga tttaccggg cgacgcgtc gcgactatcg gctttgcgag cccggactat    420
ttgacgctgg atctggtgtg cgcgtatctg ggcctggtca gcgttccttt gcagcataac    480
gctccggtgt ctcgcctggc cccgattctg gccgaggtgg aaccgcgtat tctgacggtg    540
agcgcagaat acctggacct ggcggttgaa tccgtccgtg atgtgaactc cgtcagccag    600
ctggttgttt tcgaccatca tccggaagtg gacgatcacc gtgacgcact ggctcgcgca    660
cgcgagcagc tggccggcaa aggtatcgca gttacgaccc tggatgcgat cgcagacgaa    720
ggcgcaggtt tgccggctga gccgatttac acggcggatc acgatcagcg tctggccatg    780
attctgtata ccagcggctc tacgggtgct ccgaaaggcg cgatgtacac cgaagcgatg    840
gtggctcgcc tgtggactat gagcgggatc acgggcgacc cgaccccggt tatcaacgtg    900
aacttcatgc cgctgaacca tctgggcggt cgtatcccga ttagcaccgc cgtgcagaat    960
ggcggtacca gctacttcgt tccggaaagc gacatgagca cgctgtttga ggatctggcc   1020
ctggtccgcc ctaccgaact gggtctggtg ccgcgtgttg cggacatgct gtaccagcat   1080
catctggcga ccgtggatcg cctggtgacc cagggcgcgg acgaactgac tgcggaaaag   1140
caggccggtg cggaactgcg tgaacaggtc ttgggcggtc gtgttatcac cggttttgtt   1200
```

```
tccaccgcgc cgttggcggc agagatgcgt gcttttctgg atatcacctt gggtgcacac   1260
atcgttgacg gttacggtct gaccgaaacc ggtgcggtca cccgtgatgg tgtgattgtt   1320
cgtcctccgg tcattgatta caagctgatc gatgtgccgg agctgggtta cttctccacc   1380
gacaaaccgt acccgcgtgg cgagctgctg gttcgtagcc acacgttgac tccgggttac   1440
tacaagcgcc agaagtcac cgcgtccgtt ttcgatcgcg acggctatta ccacaccggc    1500
gacgtgatgg cagaaaccgc gccagaccac ctggtgtatg tggaccgccg caacaatgtt   1560
ctgaagctgg cgcaaggtga atttgtcgcc gtggctaacc tggagtccgt tttcagcggc   1620
gctgctctgt ccgccagat tttcgtgtat ggtaacagcg agcgcagctt tctgttggct    1680
gttgttgtcc ctaccccgga ggcgctggag caatacgacc ctgccgcatt gaaagcagcc   1740
ctggcggatt cgctgcagcg tacgcgcgt gatgccgagc tgcagagcta tgaagtgccg     1800
gcggacttca ttgttgagac tgagcctttt agcgctgcga acggtctgct gagcggtgtt   1860
ggcaagttgc tgcgtccgaa tttgaaggat cgctacggtc agcgtttgga gcagatgtac   1920
gcggacatcg cggctacgca ggcgaaccaa ttgcgtgagc tgcgtcgcgc tgcggctact   1980
caaccggtga tcgacacgct gacgcaagct gcggcgacca tcctgggtac cggcagcgag   2040
gttgcaagcg acgcacactt tactgatttg ggcggtgatt ctctgagcgc gctgacgttg   2100
agcaacttgc tgtctgactt cttttggcttt gaagtcccgg ttggcacgat tgttaaccca   2160
gcgactaatc tggcacagct ggcgcaacat atcgaggcgc agcgcacggc gggtgaccgc   2220
cgtccatcct ttacgacggt ccacggtgcg gatgctacgg aaatccgtgc aagcgaactg   2280
actctggaca aattcatcga cgctgagact ctgcgcgcag cacctggttt gccgaaggtt   2340
acgactgagc cgcgtacggt cctgttgagc ggtgccaatg gttggttggg ccgcttcctg   2400
accctgcagt ggctggaacg tttggcaccg gttggcggta ccctgatcac cattgtgcgc   2460
ggtcgtgacg atgcagcggc ccgcgcacgc ttgactcagg cttacgatac ggacccagag   2520
ctgtcccgcc gcttcgctga gttggcggat cgccacttgc gtgtggtggc aggtgatatc   2580
ggcgatccga atctgggcct gaccccggag atttggcaca gtctggcagc agaggtcgat   2640
ctggtcgttc atccagcggc cctggtcaac cacgtcctgc cgtaccgcca gctgtttggt   2700
ccgaatgttg ttggcaccgc cgaagttatc aagttggctc tgaccgagcg catcaagcct   2760
gttacctacc tgtccacggt tggggtcgcg aggggtattc ctgattttga ggaggacggt   2820
gacattcgta ccgtcagccc ggttcgtccg ctggatggtg gctatgcaaa tggctatggc   2880
aacagcaagt gggctggcga ggtgctgctg cgcgaggcac atgacctgtg tggcctgccg   2940
gttgcgacgt tcgtagcga catgattctg gcccacccgc gctaccgtgg ccaagtgaat    3000
gtgccggaca tgttcacccg tctgctgctg tccctgctga tcacgggtgt ggcaccgcgt   3060
tccttctaca ttggtgatgg cgagcgtccg cgtgcacact acccgggcct gaccgtcgat   3120
tttgttgcgg aagcggttac taccctgggt gctcagcaac gtgagggtta tgtctcgtat   3180
gacgttatga atccgcacga tgacggtatt agcttggatg tctttgtgga ctggctgatt   3240
cgtgcgggcc acccaattga ccgtgttgac gactatgatg actgggtgcg tcgttttgaa   3300
accgcgttga ccgccttgcc ggagaaacgt cgtgcgcaga ccgttctgcc gctgctgcat   3360
gcctttcgcg cgccacaggc gccgtggcgt ggcgccctg aaccgaccga agtgtttcat     3420
gcagcggtgc gtaccgctaa agtcggtccg ggtgatattc cgcacctgga tgaagccctg   3480
atcgacaagt acatccgtga cctgcgcgag ttcggtctga tttag                   3525
```

US 10,676,763 B2

MICROBIAL PRODUCTION OF FATTY DIOLS

CROSS-REFERENCE TO RELATED APPLICATIONS

This application is a U.S. 371 National Stage Application of PCT/US2015/041031, filed Jul. 17, 2015, which claims the benefit of U.S. Provisional Application No. 62/026,573 filed Jul. 18, 2014, the entire disclosures of which are hereby incorporated by reference.

SEQUENCE LISTING

The instant application contains a Sequence Listing which has been submitted electronically in ASCII format and is hereby incorporated by reference in its entirety. Said ASCII copy, created on Jul. 17, 2015, is named LS00052PCT_SL.txt and is 50,064 bytes in size.

FIELD

The disclosure relates to fatty diols and methods of producing them. Herein, the disclosure pertains to recombinant microorganisms engineered to produce fatty diols via fermentation. Further encompassed is a process that uses the microorganisms to produce fatty diols from a simple carbon source.

BACKGROUND

Fatty alcohols have many commercial uses as components of industrial agents and processes, particularly in the production of detergents and surfactants. They are used as emulsifiers, emollients and thickeners in cosmetics and foods and as industrial solvents and plasticizers. Fatty alcohols can be produced from petrochemical- or oleochemical derived feedstocks. Petrochemicals are chemical products derived from petroleum. Oleochemicals are refined oils derived from natural sources such as plant and animal fats.

The chemical route for making fatty alcohols is energy intensive and environmentally costly and requires the use of hazardous reagents. For example, ethylene can be oligomerized using triethylaluminium followed by air oxidation. This process creates even-numbered fatty alcohols and is known as the Ziegler process. Alternatively, ethylene can be oligomerized to give mixtures of alkenes, which are then subjected to hydroformylation, resulting in odd-numbered aldehydes that are subsequently hydrogenated to give fatty alcohols. In another chemical process, olefin products are converted to fatty aldehydes and then to fatty alcohols. The olefin products are made by the Shell higher olefin process that was commercialized in 1977 by Royal Dutch Shell (e.g., producing approximately over one million tons of olefins annually).

The natural route for making fatty alcohols, while considered a green process, is still costly in comparison to the chemical route. Traditionally, fatty alcohols were derived from fatty esters or wax esters, which were originally extracted from the sperm oil of whales and later from tallow (e.g., animal fat from beef or lamb). An alternative plant source for wax esters is the jojoba plant. Today, fatty alcohols can also be produced from oleochemical derived feedstocks (e.g., refined plant oils) such as rapeseed oil, mustard seed oil, coconut oil, or palm kernel oil. Such vegetable oils are predominantly composed of triacylglycerols (TAGs), which contain glycerol esterified with three fatty acids (FAs). The diverse uses of vegetable oils depend on the FA composition of TAG. For example, a high proportion of lauric acid (12:0) is needed for soap production, whereas oils rich in oleic acid (18:1) are recommended for cooking. TAGs can be subjected to transesterification to give esters, which in turn are hydrogenated to fatty alcohols. Although tallow is mostly $C_{16}$-$C_{18}$, the chain length from plant sources are more variable (e.g., $C_6$-$C_{24}$). Long-chain alcohols (e.g., $C_{20}$-$C_{22}$) can be obtained from rapeseed or mustard seed while mid-cut fatty alcohols (e.g., $C_{12}$-$C_{14}$) can be obtained from coconut or palm kernel oil. Coconut and palm kernal oil are rich in lauric acid ($C_{12}$) and myristic acid ($C_{14}$). Since the European outbreak of bovine spongiform encephalopathy (i.e., mad cow disease) in 2000, tallow is commonly replaced by vegetable oleic fatty acids, derived from palm oil and soybean oil.

Fatty diols or aliphatic diols are examples of fatty alcohols and can be produced via chemical methods. For example, 1,3-diols can be synthesized from ethylene and carboxylic acid chlorides (see, e.g., Kirchanov et al. (1981) Translation from *Izvestiya Akademii Nauk SSSR, Seriya Khimicheskaya* 4:909-911). 1,3-diols can also be made by hydration of α,β-unsaturated ketones and aldehydes, wherein the resulting keto-alcohol is hydrogenated. Another chemical synthesis of 1,3-diols involves the hydroformylation of epoxides followed by hydrogenation of the aldehyde (e.g., making 1,3-propanediol from ethylene oxide). More specialized routes to 1,3-diols include the reaction between an alkene and a formaldehyde and the use of β-hydroxy ketones. 1,3-diols have been associated with being useful as food additives (see, e.g., U.S. Pat. No. 3,806,615). The 1,3-dihydroxy configuration is responsible for the non-toxic nature of these chemical entities.

1,3 diols are bifunctional, and can be used as linking molecules between other molecules, for example in the production of polymers. For example, a 1,3 propane diol is used as a monomer in the production of polymers. A 1,3 fatty diol can also be used as precursor to surfactants, for example, a "Gemini" surfactant in which both alcohol moieties are chemically modified (e.g., ethoxylated, glycosylated, sulfated, etc.). The 3-hydroxy moieties of 1,3-fatty diols are also chiral, which makes them useful as synthons for the production of chirally important compounds such as monomers, pharmaceuticals, nutraceuticals, pesticides, herbicides, flavors, fragrances, solvents, and the like.

Since fatty diols are important components of industrial agents and processes it would be desirable to produce them in high enough quantities to meet industry needs while maintaining a lower impact on the environment. The present disclosure addresses this need.

SUMMARY

One aspect of the disclosure provides a recombinant microorganism for producing a 1,3 fatty diol when grown in a fermentation broth with a simple carbon source, the microorganism includes a nucleic acid sequence encoding a polypeptide having a thioesterase (EC 3.1.2.-, EC 3.1.1.5, or EC 3.1.2.14) activity, and a carboxylic acid reductase (EC 6.2.1.3 or EC 1.2.1.42) activity. In one aspect, the 1,3 fatty diol is produced in vivo. In another aspect, the 1,3 fatty diol includes, but is not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol. In still another aspect, the simple carbon source is derived from a renewable feedstock. In one embodiment, the disclosure provides a recombinant microorganism, wherein the microorganism includes a nucleic acid sequence encoding a polypeptide having a thioesterase (EC 3.1.2.-, EC 3.1.1.5, or EC 3.1.2.14) activity, and a carboxylic acid reductase (EC 6.2.1.3 or EC 1.2.1.42) activity, and wherein the microorganism produces a 1,3 fatty diol when grown in a fermentation broth with a simple carbon source. In another embodiment, the nucleic acid sequence is exogenous. In another embodiment, the nucleic acid sequence includes one or more nucleic acid sequence(s).

Another aspect of the disclosure provides a recombinant microorganism for producing a 1,3 fatty diol when grown in a fermentation broth with a simple carbon source, the microorganism includes a pathway engineered to express a nucleic acid sequence encoding a polypeptide having a thioesterase (EC 3.1.2.-, EC 3.1.1.5, or EC 3.1.2.14) activity, and a carboxylic acid reductase (EC 6.2.1.3 or EC 1.2.1.42) activity. In one aspect, the 1,3 fatty diol is produced in vivo. In another aspect, the 1,3 fatty diol includes, but is not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{ii}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol. In still another aspect, the simple carbon source is derived from a renewable feedstock. In one embodiment, the disclosure provides a recombinant microorganism that has a pathway engineered to express a nucleic acid sequence encoding a polypeptide having a thioesterase (EC 3.1.2.-, EC 3.1.1.5, or EC 3.1.2.14) activity, and a carboxylic acid reductase (EC 6.2.1.3 or EC 1.2.1.42) activity, wherein said microorganism produces a 1,3 fatty diol when grown in a fermentation broth with a simple carbon source. In another embodiment, the nucleic acid sequence is exogenous. In another embodiment, the nucleic acid sequence includes one or more nucleic acid sequence(s).

Another aspect of the disclosure provides a recombinant microorganism for producing a 1,3 fatty diol when grown in a fermentation broth with a simple carbon source, the microorganism engineered to express one or more nucleic acid sequence(s) encoding a polypeptide having a thioesterase (EC 3.1.2.-, EC 3.1.1.5, or EC 3.1.2.14) activity, a carboxylic acid reductase (EC 6.2.1.3 or EC 1.2.1.42) activity, and optionally an alcohol dehydrogenase (EC 1.1.1.) activity. In one aspect, the 1,3 fatty diol is produced in vivo. In another aspect, the 1,3 fatty diol includes, but is not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol. In still another aspect, the simple carbon source is derived from a renewable feedstock. In one embodiment, the disclosure provides a recombinant microorganism engineered to express one or more nucleic acid sequence(s) encoding a polypeptide having a thioesterase (EC 3.1.2.-, EC 3.1.1.5, or EC 3.1.2.14) activity, a carboxylic acid reductase (EC 6.2.1.3 or EC 1.2.1.42) activity, and an alcohol dehydrogenase (EC 1.1.1.) activity, wherein said microorganism for produces a 1,3 fatty diol when grown in a fermentation broth with a simple carbon source. In another embodiment, the one or more nucleic acid sequence(s) are exogenous.

Another aspect of the disclosure provides a recombinant microorganism for producing a 1,3 fatty diol when grown in a fermentation broth with a simple carbon source, the microorganism includes a pathway engineered to express one or more nucleic acid sequence(s) encoding a polypeptide having a thioesterase (EC 3.1.2.-, EC 3.1.1.5, or EC 3.1.2.14) activity, a carboxylic acid reductase (EC 6.2.1.3 or EC 1.2.1.42) activity, and optionally an alcohol dehydrogenase (EC 1.1.1.) activity. In one aspect, the 1,3 fatty diol is produced in vivo. In another aspect, the 1,3 fatty diol includes, but is not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol. In still another aspect, the simple carbon source is derived from a renewable feedstock. In one embodiment, the disclosure provides a recombinant microorganism that has a pathway engineered to express one or more nucleic acid sequence(s) encoding a polypeptide having a thioesterase (EC 3.1.2.-, EC 3.1.1.5, or EC 3.1.2.14) activity, a carboxylic acid reductase (EC 6.2.1.3 or EC 1.2.1.42) activity, and an alcohol dehydrogenase (EC 1.1.1.) activity, wherein said microorganism produces a 1,3 fatty diol when grown in a fermentation broth with a simple carbon source. In another embodiment, the one or more nucleic acid sequences are exogenous.

Another aspect of the disclosure provides a recombinant microorganism for producing a 1,3 fatty diol when grown in a fermentation broth with a simple carbon source, wherein the simple carbon source is derived from a renewable feedstock.

Another aspect of the disclosure provides a recombinant microorganism for producing a 1,3 fatty diol when grown in a fermentation broth with a simple carbon source, wherein the microorganism expresses one or more nucleic acid sequence(s) encoding a polypeptide having a thioesterase (EC 3.1.2.-, EC 3.1.1.5, or EC 3.1.2.14) activity, and a carboxylic acid reductase (EC 6.2.1.3 or EC 1.2.1.42) activity. In one embodiment, the thioesterase includes, but is not limited to, fatB1, TE_EEI82564, TE_CAD63310, phaG, and tesA. In another embodiment, the carboxylic acid reductase is carB. In still another embodiment, the one or more nucleic acid sequence(s) are exogenous.

Another aspect of the disclosure provides a recombinant microorganism for producing a 1,3 fatty diol when grown in a fermentation broth with a simple carbon source, the microorganism includes a pathway engineered to express one or more nucleic acid sequence(s) encoding a polypeptide having a thioesterase (EC 3.1.2.-, EC 3.1.1.5, or EC 3.1.2.14) activity, and a carboxylic acid reductase (EC 6.2.1.3 or EC 1.2.1.42) activity. In one embodiment, the thioesterase includes, but is not limited to, fatB1, TE_EEI82564, TE_CAD63310, phaG, and tesA. In another embodiment, the carboxylic acid reductase is carB. In still another embodiment, the one or more nucleic acid sequence(s) are exogenous.

Another aspect of the disclosure provides a recombinant microorganism for producing a 1,3 fatty diol when grown in a fermentation broth with a simple carbon source, wherein the microorganism expresses one or more nucleic acid sequence(s) encoding a polypeptide having a thioesterase (EC 3.1.2.-, EC 3.1.1.5, or EC 3.1.2.14) activity, a carboxylic acid reductase (EC 6.2.1.3 or EC 1.2.1.42) activity, and an alcohol dehydrogenase (EC 1.1.1.) activity. In one embodiment, the thioesterase includes, but is not limited to, fatB1, TE_EEI82564, TE_CAD63310, phaG, and tesA. In another embodiment, the carboxylic acid reductase is carB. In still another embodiment, the alcohol dehydrogenase is alrA. In yet another embodiment, the one or more nucleic acid sequence(s) are exogenous.

Another aspect of the disclosure provides a recombinant microorganism for producing a 1,3 fatty diol when grown in a fermentation broth with a simple carbon source, the microorganism includes a pathway engineered to express one or more nucleic acid sequence(s) encoding a polypeptide having a thioesterase (EC 3.1.2.-, EC 3.1.1.5, or EC 3.1.2.14) activity, a carboxylic acid reductase (EC 6.2.1.3 or EC 1.2.1.42) activity, and an alcohol dehydrogenase (EC 1.1.1.) activity. In one embodiment, the thioesterase is includes, but is not limited to, fatB1, TE_EEI82564, TE_CAD63310, phaG, and tesA. In another embodiment, the carboxylic acid reductase is carB. In still another embodiment, the alcohol dehydrogenase is alrA. In yet another embodiment, the one or more nucleic acid sequence (s) are exogenous.

The disclosure further encompasses a cell culture including a recombinant microorganism for producing a 1,3 fatty diol when grown in a fermentation broth with a simple carbon source. In one aspect, the microorganism is engineered to express a nucleic acid sequence encoding a polypeptide having a thioesterase (EC 3.1.2.-, EC 3.1.1.5, or EC 3.1.2.14) activity, and a carboxylic acid reductase (EC 6.2.1.3 or EC 1.2.1.42) activity. In another aspect, the microorganism is engineered to express a nucleic acid sequence encoding a polypeptide having a thioesterase (EC 3.1.2.-, EC 3.1.1.5, or EC 3.1.2.14) activity, a carboxylic acid reductase (EC 6.2.1.3 or EC 1.2.1.42) activity, and an alcohol dehydrogenase (EC 1.1.1.-) activity. In another aspect, the cell culture produces 1,3 fatty diols. In another aspect, the cell culture produces a 1,3 fatty diol including a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, a $C_{19}$ 1,3 fatty diol and the like. In one embodiment, the nucleic acid sequence is exogenous. In another embodiment, the nucleic acid sequence includes one or more nucleic acid sequences.

The disclosure further contemplates a method of producing a 1,3 fatty diol including the microorganism as described above (supra).

Another aspect of the disclosure provides a method of producing a 1,3 fatty diol including providing a recombinant microorganism in a fermentation broth, the microorganism expressing one or more nucleic acid sequence(s) encoding a polypeptide having a thioesterase (EC 3.1.2.-, EC 3.1.1.5, or EC 3.1.2.14) activity, a carboxylic acid reductase (EC 6.2.1.3 or EC 1.2.1.42) activity, and optionally an alcohol dehydrogenase (EC 1.1.1.-) activity; and isolating a 1,3 fatty diol from said fermentation broth. In one embodiment, the method further includes adding a simple carbon source to the fermentation broth. In yet another embodiment, the simple carbon source is derived from a renewable feedstock. In another aspect, the disclosure provides a method of producing a 1,3 fatty diol including providing a recombinant microorganism in a fermentation broth, the microorganism engineered to express one or more nucleic acid sequence(s) encoding a polypeptide having a thioesterase (EC 3.1.2.-, EC 3.1.1.5, or EC 3.1.2.14) activity; and a carboxylic acid reductase (EC 6.2.1.3 or EC 1.2.1.42) activity; and isolating a 1,3 fatty diol from the fermentation broth. In one aspect, the 1,3 fatty diol includes, but is not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol. In one embodiment, the method further includes adding a simple carbon source to the fermentation broth. In yet another embodiment, the simple carbon source is derived from a renewable feedstock.

Another aspect of the disclosure provides a recombinant microorganism for producing a 1,3 fatty diol when grown in a fermentation broth with a simple carbon source, the microorganism expressing a nucleic acid sequence encoding a polypeptide having an acyl-ACP reductase (EC 1.2.1.80 or EC 1.2.1.42) activity. In one aspect, the 1,3 fatty diol is produced in vivo. In another aspect, the fatty diol includes, but is not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol. In one embodiment, the nucleic acid sequence is exogenous.

Still another aspect of the disclosure provides a recombinant microorganism for producing a 1,3 fatty diol when grown in a fermentation broth with a simple carbon source, the microorganism expressing one or more nucleic acid sequence(s) encoding a polypeptide having an acyl-ACP reductase (EC 1.2.1.80 or EC 1.2.1.42) activity, and an alcohol dehydrogenase (EC 1.1.1.-) activity. In one aspect, the 1,3 fatty diol is produced in vivo. In another aspect, the fatty diol includes, but is not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol. In one embodiment, the one or more nucleic acid sequence(s) are exogenous.

The disclosure further contemplates a cell culture including a recombinant microorganism for producing a 1,3 fatty diol when grown in a fermentation broth with a simple carbon source, the microorganism engineered to express one or more nucleic acid sequence(s) encoding a polypeptide having an acyl-ACP reductase (EC 1.2.1.80 or EC 1.2.1.42) activity, and optionally an alcohol dehydrogenase (EC 1.1.1.-) activity. In one aspect, the cell culture produces 1,3 fatty diols. In another aspect, the fatty diol includes, but is not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol. In one embodiment, the one or more nucleic acid sequence(s) are exogenous.

In yet another aspect, the disclosure encompasses at method of producing a 1,3 fatty diol including providing a recombinant microorganism in a fermentation broth, the microorganism engineered to express a nucleic acid sequence encoding a polypeptide having an acyl-ACP reductase (EC 1.2.1.80 or EC 1.2.1.42) activity; and isolating a 1,3 fatty diol from the fermentation broth. In one embodiment, the microorganism further expresses a nucleic acid sequence encoding a polypeptide having an alcohol dehydrogenase (EC 1.1.1.-) activity. In another embodiment, the method further includes adding a simple carbon source to the fermentation broth. In yet another embodiment, the simple carbon source is derived from a renewable feedstock. The method produces a fatty diol including, but not limited to, a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol.

In yet another aspect, the disclosure further encompasses the secretion and recovery of 1,3 fatty diols from any of the recombinant microorganisms discussed above (supra). In one embodiment, 1,3 fatty diols are secreted into the fermentation broth. In another embodiment, 1,3 fatty diols are recovered via oil water separation such as via gravity settling, centrifugation, decantation, or the like.

The disclosure further contemplates a fatty diol composition. In one aspect, the composition includes one or more fatty diols, including 1,3-diols.

Still, another aspect of the disclosure provides for the use of fatty diols in the production of surfactants, including ethoxylates and the like.

The disclosure further encompasses chiral 1,3 fatty diols, their enantiomers and chiral mixtures. Further contemplated are compositions of 1,3 fatty diols, their enantiomers and chiral mixtures.

BRIEF DESCRIPTION OF THE DRAWINGS

The present disclosure is best understood when read in conjunction with the accompanying figures, which serve to illustrate some of the preferred embodiments. It is understood, however, that the disclosure is not limited to the specific embodiments disclosed in the figures.

The following abbreviations are used in FIGS. 8-11:
FAS—fatty acid biosynthesis/fatty acid synthase
TE—thioesterase
ACS—acyl CoA synthase
TL—3-ketoacyl CoA thiolase (reversible)
(S)3HACS—(S)-3-hydroxy-acyl CoA dehydrogenase (reversible)
(S)2ECOH—(S)-2-enoyl CoA hydratase/(S)-3-hydroxylacyl CoA dehydratase
CAR—carboxylic acid reductase
FAR—fatty acyl CoA/ACP reductase and fatty alcohol forming fatty acyl CoA/ACP reductase
ACR—acyl CoA reductase
AAR—acyl ACP/CoA reductase

DETAILED DESCRIPTION

General Overview

Figure 1:
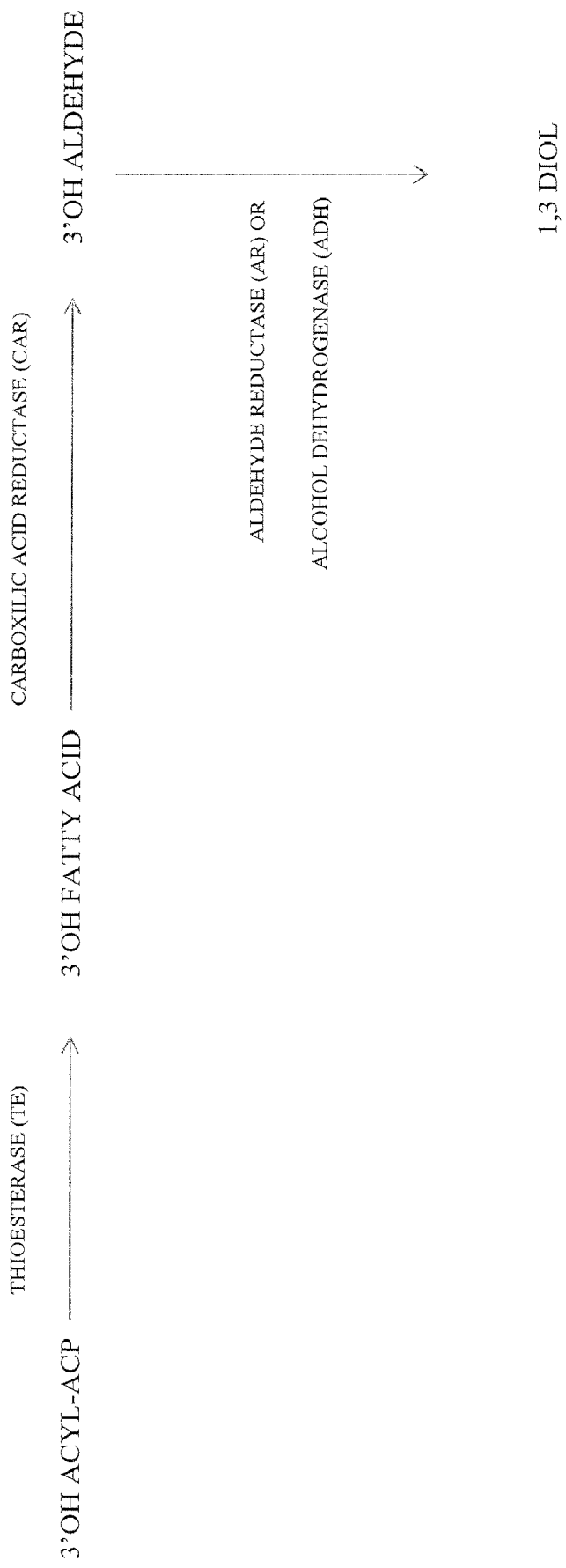
FIG. 1 depicts an exemplary pathway for making 1,3-diols, including enzymatic functionalities.

The development of a new and environmentally friendly method for the production of fatty diols provides an improvement to the industry. The method allows for the production of fatty diols from a simple carbon source that is derived from a renewable feedstock, including but not limited to, carbohydrates from corn, cane, natural gas, or lignocellulosic biomass; waste products such as municipal solid waste, glycerol, flu-gas, syn-gas, carbon dioxide; or the carbon streams resulting from the reformation of organic materials such as biomass, natural gas, or other carbonaceous materials. The method further allows for the production fatty diols from $CO_2$ and light by photosynthetic organisms, such as cyanobacteria and algae. This method is better for the environment because it does not produce the toxic byproducts that petrochemical derived processes generate.

More specifically, the present disclosure provides recombinant microorganisms that are engineered to convert a simple carbon source derived from a renewable feedstock to fatty diols. 1,3-diols are examples of fatty diols which are stable chemical entities that are colorless and odorless. Microbially produced 1,3-diols are expected to have many industrial applications, including as components of detergents, surfactants, emulsifiers, emollients, solvents, plastics, flavors, fragrances, and bioactive compounds. Microbially produced 1,3-diols will also find use in the food industry as replacements of (or additives to) natural foods because they are easily metabolized, non-toxic, non-volatile, and energy dense with a long shelf-life.

The recombinant microorganisms of the present disclosure are used in fermentation processes for the production of fatty diols. Herein, the disclosure encompasses microbial fatty acid metabolisms and the conversion of its intermediates to 1,3-diols. One advantage of the present disclosure is a cleaner production method, i.e., employing a simple fermentation process. The use of renewable feedstocks protects the environment because it relies on renewable and sustainable raw materials that do not deplete natural resources. The use of industrial waste products (e.g., glycerol) as feedstocks supports better waste management and recycling. Another advantage is the option to manufacture novel industrial target products, i.e., fatty diol compositions with selective chain lengths, chiralities, and in specific mixtures or in combination with derivatives.

DEFINITIONS

As used herein, the terms "1,3 fatty diol" or "1,3-diol" or "1,3-dialcohol" or "3-OH fatty alcohol" or "3-hydroxy fatty alcohol" or "1,3-dihydroxy alcohol" or "1,3-aliphatic diol" are used interchangeably herein and refer to a chemical entity that has a chain length of at least 5 carbons and originates from microbial fatty acid metabolisms via fatty-acyl thioester intermediates and has at least two OH groups, i.e., an OH group at position 1 and an OH group at position 3 of its carbon chain.

A "1,3-diol" as referred to herein is produced by a recombinant microorganism or a recombinant microbial host cell.

A "1,3-diol composition" typically includes at least a 1,3-diol in combination with another ingredient.

The term "enzyme classification (EC) number" refers to a number that denotes a specific polypeptide sequence or enzyme. EC numbers classify enzymes according to the reaction they catalyze. EC numbers are established by the nomenclature committee of the international union of biochemistry and molecular biology (IUBMB), a description of which is available on the IUBMB enzyme nomenclature website on the world wide web.

The term "thioesterase" refers to an enzymatic activity that is characterized by EC Number 3.1.2.14. or EC Number 3.1.1.5 or EC Number 3.1.2.-.

The term "carboxylic acid reductase (CAR)" refers to an enzymatic activity that is characterized by EC Number 6.2.1.3 or EC Number 1.2.1.42 or EC Number 1.2.99.6.

The terms "aldehyde reductase" and "alcohol dehydrogenase" are used interchangeably herein and refer to an enzymatic activity that is characterized by EC Number 1.1.-.-.

The term "acyl-ACP reductase (AAR)" refers to an enzymatic activity that is characterized by EC Number 1.2.1.80 or EC Number 1.2.1.42.

The term "acetyl-CoA carboxylase" refers to an enzymatic activity that is characterized by EC Number 6.4.1.2.

The terms "accession number" and "NCBI accession number" and "GenBank accession number" are used interchangeably herein and refer to a number that denotes a specific nucleic acid sequence. Sequence accession numbers that are discussed in this description were obtained from databases provided by the NCBI (National Center for Biotechnology Information) maintained by the National Institutes of Health, U.S.A., and from the UniProt Knowledgebase (UniProtKB) and Swiss-Prot databases provided by the Swiss Institute of Bioinformatics (also referred to as UniProtKB accession number).

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

As used herein, the term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

The terms "endogenous polynucleotide" and "endogenous DNA" and "endogenous nucleic acid sequence" are used interchangeably herein and refer to DNA that originates inside of the host cell.

The terms "exogenous polynucleotide" and "exogenous DNA" and "exogenous nucleic acid sequence" are used interchangeably herein and refer to DNA that originates outside of the host cell. For example, a gene from host cell A can be inserted into host cell B. However, a gene originating from host cell A can be manipulated or modified (inside or outside the host cell A) and re-inserted into the same host cell A.

The terms "modified polynucleotide" and "modified DNA" and "modified nucleic acid sequence" are used interchangeably herein and refer to DNA that has in some form been altered relative to its original or natural state. This alternation may affect the stability, expression, activity or function of the DNA or its encoded gene product (e.g., polypeptide or protein). In one embodiment, the expression of the encoded polypeptide is increased. In another embodiment, the expression of the encoded polypeptide is decreased. In another embodiment, the expression of the encoded polypeptide is absent.

As used herein, the terms "polypeptide" and "protein" and "polypeptide sequence" and "protein sequence" are used interchangeably herein and refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide.

As used herein, the terms "homolog," and "homologous" refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and sequence "identity" are used interchangeably. One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a first sequence that is aligned for comparison purposes is at least about 30%, preferably at least about 40%, more preferably at least about 50%, even more preferably at least about 60%, and even more preferably at least about 70%, at least about 75%, at least about 80%, at least about 85%, at least about 90%, at least about 95%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences. The comparison of sequences and determination of percent homology between two sequences can be accomplished using a mathematical algorithm, such as BLAST (Altschul et al. (1990) *J. Mol. Biol.* 215(3): 403-410). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, (1970) J. Mol. Biol. 48:444-453). The percent homology between two nucleotide sequences also can be determined using the GAP program in the GCG software package, using a NWSgapdna. CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) *BMC Bioinformatics* 6:278); Altschul et al. (2005) *FEBS J.* 272(20): 5101-5109).

An "endogenous" polypeptide refers to a polypeptide encoded by the genome of the host cell (e.g., parental microbial cell) from which the recombinant cell is engineered or derived.

An "exogenous" polypeptide refers to a polypeptide which is not originally encoded by the genome of the parental or host microbial cell (e.g., host cell). A variant (i.e., mutant) polypeptide is an example of an exogenous polypeptide. Another example of an exogenous polypeptide is a protein that occurs in the native cell but is the result of altered expression, for example, expression of an exogenous polynucleotide (e.g., a vector or plasmid containing a gene identical to a native gene but engineered to be overexpressed in the host cell; such a gene may be optionally inserted into the host DNA).

The term "heterologous" generally means derived from a different species or derived from a different organism or derived from a different source. As used herein it refers to a nucleotide sequence or a polypeptide sequence that is not naturally present in a particular organism. Heterologous expression means that a protein or polypeptide is expressed in a cell that does not normally express that protein. As such, heterologous means that a transferred protein was initially derived from a different cell type or a different species or a different source then the recipient. For example, a polynucleotide sequence endogenous to a plant cell can be introduced into a bacterial host cell by recombinant methods, and the plant polynucleotide is then a heterologous polynucleotide in a recombinant bacterial host cell. Another example of a heterologous polypeptide is a protein that occurs in the native cell but is the result of altered expression, for example, expression of a heterologous polynucleotide (e.g., a vector or plasmid containing a gene identical to a native gene but engineered to be overexpressed in the host cell; such a gene may be optionally inserted into the host DNA).

As used herein, the term "fragment" of a polypeptide refers to a shorter portion of a full-length polypeptide or protein ranging in size from four amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

As used herein, the term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al. (1987) *Science* 236:1237-1245). Exemplary expression control sequences are described in, for example, Goeddel, Gene Expression Technology: Methods in Enzymology, Vol. 185, Academic Press, San Diego, Calif. (1990).

The term "plurality" refers to at least 2 in number (e.g., a plurality of polynucleotide sequences means at least two polynucleotide sequences).

In the methods of the disclosure, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, in as much as a plasmid is the most commonly used form of vector. However, also included are such other forms of expression vectors that serve equivalent functions and that become known in the art subsequently hereto. In some embodiments, a recombinant vector further comprises a promoter operably linked to the polynucleotide sequence. In some embodiments, the promoter is a developmentally-regulated, an organelle-specific, a tissue-specific, an inducible, a constitutive, or a cell-specific promoter. The recombinant vector typically comprises at least one sequence including (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, E. coli, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. In certain embodiments, a polynucleotide sequence of the disclosure is operably linked to a promoter derived from bacteriophage T5. In certain embodiments, the host cell is a yeast cell, and the expression vector is a yeast expression vector. Examples of vectors for expression in yeast *S. cerevisiae* include pYepSec1 (Baldari et al. (1987) *EMBO J.* 6:229-234), pMFa (Kurjan et al. (1982) *Cell* 30: 933-943), pJRY88 (Schultz et al. (1987) *Gene* 54: 113-123), pYES2 (Invitrogen Corp., San Diego, Calif.), and picZ (Invitrogen Corp., San Diego, Calif.). In other embodiments, the host cell is an insect cell, and the expression vector is a baculovirus expression vector. Baculovirus vectors available for expression of proteins in cultured insect cells (e.g., Sf9 cells) include, for example, the pAc series (Smith et al. (1983) *Mol. Cell Biol.* 3:2156-2165) and the pVL series (Lucklow et al. (1989) *Virology* 170:31-39). In yet another embodiment, the polynucleotide sequences described herein can be expressed in mammalian cells using a mammalian expression vector. Other suitable expression systems for both prokaryotic and eukaryotic cells are well known in the art; see, e.g., Sambrook et al., "Molecular Cloning: A Laboratory Manual," second edition, Cold Spring Harbor Laboratory, (1989).

As used herein "acyl-CoA" refers to an acyl thioester formed between the carbonyl carbon of alkyl chain and the sulfhydryl group of the 4'-phosphopantethionyl moiety of coenzyme A (CoA), which has the formula R—C(O)S-CoA, where R is any alkyl group having at least 4 carbon atoms.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase that uses Coenzyme A as substrate and the phosphopantetheinyl donor. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives. As evident to one of skill, the 4'-phosphopantethionyl moiety of holo ACP is derived from Coenzyme A. Thus, enzymes that utilize acyl ACP as substrate often have some activity for acyl CoA and enzymes that utilize acyl CoA as substrate have some activity for acyl ACP.

As used herein, the term "fatty acid biosynthetic pathway" means a biosynthetic pathway that produces fatty acids, fatty acid thioesters and/or derivatives thereof. The fatty acid biosynthetic pathway may include additional enzymes or polypeptides with enzymatic activities besides the ones discussed herein to produce fatty acid derivatives having desired characteristics.

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen. "Culturing" or "cultivation" refers to growing a population of recombinant host cells under suitable conditions in a liquid or solid medium. In particular embodiments, culturing refers to the fermentative bioconversion of a substrate to an end-product. Culturing media are well known and individual components of such culture media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium. The host cell of a culture can be additionally engineered to assimilate carbon efficiently and use cellulosic materials as carbon sources according to methods described in U.S. Pat. Nos. 5,000,000; 5,028,539; 5,424,202; 5,482,846; 5,602,030; WO 2010127318. In addition, in some embodiments the host cell is engineered to express an invertase so that sucrose can be used as a carbon source.

As used herein, the term "under conditions effective to express a genetically engineered polynucleotide sequence" means any condition that allows a host cell to express the corresponding enzymatic functionality in order to produce a desired fatty acid derivative such as a fatty diol. Suitable conditions include, for example, fermentation conditions.

The term "recombinant microorganism" refers to a host cell that has been genetically modified or engineered such that certain enzymatic activities within the host cell have been altered, added and/or deleted relative to the parent cell or native host cell. A genetically modified or genetically engineered host cell is an example of a recombinant microorganism. As such, a "modified or altered level of activity of a protein", for example an enzyme, in a recombinant host cell refers to a difference in one or more characteristics in the activity determined relative to the parent or native host cell in which that same modification is absent. Typically differences in activity are determined between a recombinant host cell, having modified activity, and the corresponding wild-type host cell (e.g., comparison of a culture of a recombinant host cell relative to the corresponding wild-type host cell), not having that modified activity. Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein. In certain instances, the coding sequences for the polypeptides described herein are codon optimized for expression in a particular host cell. For example, for expression in *E. coli*, one or more codons can be optimized (as described in, e.g., Grosjean et al. (1982) *Gene* 18:199-209). In one embodiment, the recombinant microorganism produces a desirable product such as a fatty acid derivative (e.g., fatty acid, fatty aldehyde, fatty alcohol, fatty diol). In one particular embodiment, the recombinant microorganism produces a 1,3-diol.

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons).

The terms "altered level of expression" and "modified level of expression" are used interchangeably and mean that a polynucleotide, polypeptide, metabolite, or product (e.g., a fatty acid derivative) is present in a different concentration in an engineered host cell as compared to its concentration in a corresponding wild-type cell under the same conditions. Examples of fatty acid derivatives are fatty acids, 3-hydroxy fatty acids, fatty aldehydes, 3-hydroxy fatty aldehydes, fatty alcohols, 1,3 fatty diols and the like.

As used herein, the term "titer" refers to the quantity of a fatty acid derivative such as, for example, a fatty diol (e.g., 1,3-diol) produced per unit volume of host cell culture, and is generally reported in mass/volume units, e.g., 10 g/L. In one embodiment, the titer may refer to a particular 1,3-diol or a combination of 1,3-diols produced by a given recombinant host cell culture. In another embodiment, the titer may also refer to a fatty diol composition (e.g., 1,3-diol composition) produced by a given recombinant host cell culture.

As used herein, the "yield of fatty diols (e.g., 1,3-diols) produced by a host cell" refers to the efficiency by which an input carbon source is converted to a product (e.g., to a fatty diol) in a host cell, and in the case of a "mass yield" is reported in percent of mass (product)/mass (carbon source) units, e.g., a 30% mass yield would refer to 30 g product being produced from 100 g of carbon source; a 20% mass yield would refer to 20 g product being produced from 100 g of carbon source; a 10% mass yield would refer to 10 g product being produced from 100 g of carbon source, and so forth. The yield may refer to a particular 1,3-diol or a combination of 1,3-diols produced by a given recombinant host cell culture.

As used herein, the term "productivity" refers to the quantity of a fatty diol (e.g., 1,3-diol) or derivatives produced per unit volume of host cell culture per unit time (e.g., reported as g/L/hr). The productivity may refer to a particular 1,3-diol or a combination of 1,3-diols produced by a given recombinant host cell culture.

As used herein, the term "glucose utilization rate" means the amount of glucose used by the culture per unit time, reported as grams/liter/hour (g/L/hr).

A "feedstock" is the raw material that is used in the manufacture of a product or for an industrial process. A "renewable feedstock" is a raw material that is derived from renewable materials such as a biological material, e.g., plant matter and that can be replaced through natural means (e.g., corn, cane, lignocellulosic biomass) or waste products such as municipal solid waste, glycerol, free fatty acids, flu-gas, or syn-gas; carbon dioxide, or the like. In comparison, a "nonrenewable feedstock" is a raw material that is depleted by use (e.g., crude oil, coal, nuclear fuel, etc.) and cannot be regenerated.

As used herein, the term "simple carbon source" refers to a substrate or compound suitable to be used as a source of fuel for prokaryotic or simple eukaryotic cell growth. Sources that qualify as a simple carbon source can be in various forms, including, but not limited to polymers, carbohydrates, acids, alcohols, aldehydes, ketones, amino acids, peptides, and gases (e.g., CO and $CO_2$). Exemplary simple carbon sources include, but are not limited to monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and propanol; glycerol, or mixtures thereof. In one embodiment, the simple carbon source is derived from corn, sugar cane, sorghum, beet, switch grass, ensilage, straw, lumber, pulp, sewage, garbage, cellulosic urban waste, flu-gas, syn-gas, or carbon dioxide. The simple carbon source can also be a product of photosynthesis, such as glucose. In one embodiment, the simple carbon source is derived from a renewable feedstock. In one particular embodiment, the simple carbon source is derived from a renewable feedstock such as a carbohydrate from corn, cane, or lignocellulosic biomass; or from a waste product such as glycerol, fatty acids, flu-gas, or syn-gas; or from the reformation of organic materials such as biomass; or from carbon dioxide that is fixed photosynthetically. In another embodiment, the simple carbon source is selected from glucose, fructose, mannose, galactose, xylose, arabinose, fructo-oligosaccharide, galacto-oligosaccharide, starch, cellulose, pectin, xylan, sucrose, maltose, cellobiose, turanose, hemicellulose, methyl cellulose, sodium carboxymethyl cellulose, succinate, lactate, acetate, ethanol, methanol, glycerol, and mixtures thereof. In certain embodiments, the simple carbon source is derived from biomass. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, and food leftovers. The term "biomass" also refers to sources of carbon, such as carbohydrates (e.g., monosaccharides, disaccharides, or polysaccharides).

As used herein, the term "isolated," with respect to products (such as 1,3-diols or derivatives) refers to products that are separated from cellular components, cell culture media, or chemical or synthetic precursors. The fatty diols (e.g., 1,3-diols) and related compositions produced by the methods described herein can be relatively immiscible in the fermentation broth, as well as in the cytoplasm. Therefore, the fatty diol compositions can collect in an organic phase either intracellularly or extracellularly. In one embodiment, the 1,3-diol compositions collect extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of fatty diols in a sample. For example, when a 1,3-diol is produced in a recombinant host cell, the 1,3-diol can be purified by the removal of host cell proteins. After purification, the percentage of 1,3-diols in the sample is increased. The terms "purify," "purified," and "purification" are relative terms which do not require absolute purity. Thus, for example, when a 1,3-diol is produced in recombinant host cells, a purified 1,3-diol is a 1,3-diol that is substantially separated from other cellular components (e.g., nucleic acids, polypeptides, lipids, carbohydrates, or other hydrocarbons).

The term "producing a fatty diol (e.g., 1,3-diol) in vivo", as used for the purpose of the specification and claims, means producing a fatty diol in viable and/or recombinant and/or genetically modified host cells from a simple carbon source, wherein the simple carbon source is added to a fermentation broth so that the host cells can take up and metabolize the simple carbon source during fermentation. In one embodiment a simple carbon source is derived from a renewable feedstock.

Engineering Host Cell Strains for Screening

Fatty acid biosynthesis is one of the most conserved systems of the bacterial biosynthetic machinery. The fatty acid synthase (FAS) multi-enzyme complex is present in all bacteria and eukaryotes. Most of the FAS related genes are required for cell growth and survival. Eukaryotic and bacterial FAS drive essentially the same type of biochemical transformation. In eukaryotes, FAS is referred to as FAS I and most of its catalytic domains are encoded by one polypeptide chain (non-dissociable). In prokaryotes such as bacteria, FAS is referred to as FASII and its individual enzymes and carrier proteins are encoded by separate genes coding for discrete (dissociable) proteins.

The acyl carrier protein (ACP) along with the enzymes in a FAS pathway control the length, degree of saturation and branching of the fatty acids produced in a native organism. The steps in this pathway are catalyzed by enzymes of the fatty acid biosynthesis (FAB) and acetyl-CoA carboxylase (ACC) gene families. For example, enzymes that can be included in an engineered FAS pathway include acetyl-CoA carboxylase (e.g., AccABCD, malonyl-CoA:ACP transacylase (e.g., FabD), 3-ketoacyl-ACP synthase III (e.g., FabH), 3-ketoacyl-ACP reductase (e.g., FabG), 3-hydroxyacyl-ACP dehydratase/isomerase (e.g., FabA), 3-hydroxyacyl-ACP dehydratase (e.g., FabZ), trans-2-enoyl-ACP reductase (e.g., FabI or FabL or FabK), trans-2-enoyl-ACP isomerase (e.g., FabM), 3-ketoacyl-ACP synthase I (e.g., FabB), and 3-ketoacyl-ACP synthase II (e.g., FabF). Depending upon the desired product one or more of these genes can be attenuated or over-expressed. As such, host cells have been engineered to increase production of fatty acid derivatives (e.g., fatty diols, fatty alcohols) as well as fatty acid derivative intermediates (e.g., fatty aldehydes) by feeding a simple carbon source that can be derived from renewable feedstock. Herein the major goal is to increase the activity of key control enzymes that regulate the production of fatty acid derivatives such as fatty diols in order to convert the bacterial strain into a microbial factory for fatty diol production. In one embodiment, the bacterial strains produce fatty diols such as 1,3-diols. In another embodiment, the bacterial strains produces fatty diols such as 1,3-diols in combination with fatty alcohols. In another embodiment, the bacterial strains are further modified such that in particular ketoacyl-ACP reductase activity is increased and/or 3-hydroxyacyl-ACP dehydratase activity is decreased which leads to increased 1,3 fatty diol production.

Host cells have previously been engineered to increase other fatty acid derivatives, including fatty acid methyl esters (FAMEs), fatty acid ethyl esters (FAEEs), and fatty alcohols (FALC) (see, e.g., U.S. Pat. No. 8,283,143, incorporated by reference herein). As will be appreciated by one skill in the art, fatty acid synthesis can also occur through the elongation of acyl CoAs using acyl ACP independent fatty acid biosynthesis. The FAS enzymes responsible for the corresponding fatty acid biosynthetic reactions, condensation, reduction, dehydration, reduction, and the like, can also be used for the synthesis of acyl thioesters that can be used as substrates for the production of fatty acid derivatives, including but not limited to fatty acids, fatty aldehydes, fatty alcohols, and 3-hydroxy derivatives thereof, including 1,3 fatty diols. As known to those of skill in the art, the biochemical reactions responsible for the oxidation of fatty acids (the β-oxidation cycle) can function in reverse to support the synthesis of fatty acid thioesters. These acyl thioesters can be used as substrates for the production of fatty acid derivatives, including but not limited to fatty acids, fatty aldehydes, fatty alcohols, and 3-hydroxy derivatives thereof, including 1,3 fatty diols. Further, in some organisms fatty acid biosynthesis can occur without ACP, for example through the synthesis of acyl CoAs (see, e.g., US Patent Application Publication No. US 2014/0051136A1; US Patent Application Publication No. US 2014/0273114A1; and Dellomonaco et al. (2011) *Nature* 476 (7360):355-9). In one aspect, components of these various and different FAS systems can be coexpressed in the same cell to work cooperatively to produce fatty acyl thioesters and derivatives, including but not limited to fatty acids, fatty aldehydes, fatty alcohols, and 3-hydroxy derivatives thereof, including 1,3 fatty diols.

Chiral Molecules

A molecule is said to be chiral if it can exist as stereoisomers (i.e., enantiomers) that are non-superimposable mirror images of each other. This is relevant because the response of an organism to a particular molecule often depends on how that molecule fits a particular site on a receptor molecule in the organism. Chiral molecules including chiral alcohols and diols are building blocks for the synthesis of certain compounds such as, for example, pharmaceuticals, nutraceuticals and other active compounds. In pharmaceutical and nutraceutical applications it is necessary to know which enantiomer is the active one and fits the intended receptor.

One way to obtain the compound as a pure active isomer is to produce the chemical by employing organisms such as microbes, because the production of biomolecules in organisms is stereospecific (i.e., it yields a specific stereoisomer). For example, amino acids, vitamins, and hormones are naturally produced by yeast during the fermentation of sugar and can be harvested therefrom. The properties of enzymes as chiral catalysts is appreciated by those of skill in the art and the increase in demand for enantiopure drugs has fueled the interest in enzymes for the purpose of fine chemical synthesis. In contrast to producing chiral molecules via organisms, when chiral molecules are made by chemical procedures, a mixture of the enantiomers (i.e., a racemic mixture) is obtained.

Current methods of enantiomeric analysis include such non-chromatographic techniques as polarimetry, nuclear magnetic resonance, isotopic dilution, calorimetry, and enzyme techniques. These techniques require pure samples, and no separation of enantiomers is involved. Quantitation (which does not require pure samples) and separation of enantiomers can be done simultaneously by chiral chromatography such as gas chromatography (GC) or high performance liquid chromatography (HPLC) using chiral columns (see *Stereochemistry of Organic Compounds*, Ernest L. Elil/Sanuel H. Wilen, 1994, John Wiley & Sons, Inc.). Biocatalysts can be used to make chiral compounds and the chiral purity of products can be identified using chiral chromatographic methods such as chiral HPLC or LC/MS (see US Patent Application Publication Nos. US2008/0248539A1 and US2013/0052699A1).

Chirality of 3-Hydroxy Fatty Acid Derivatives

Figure 10:
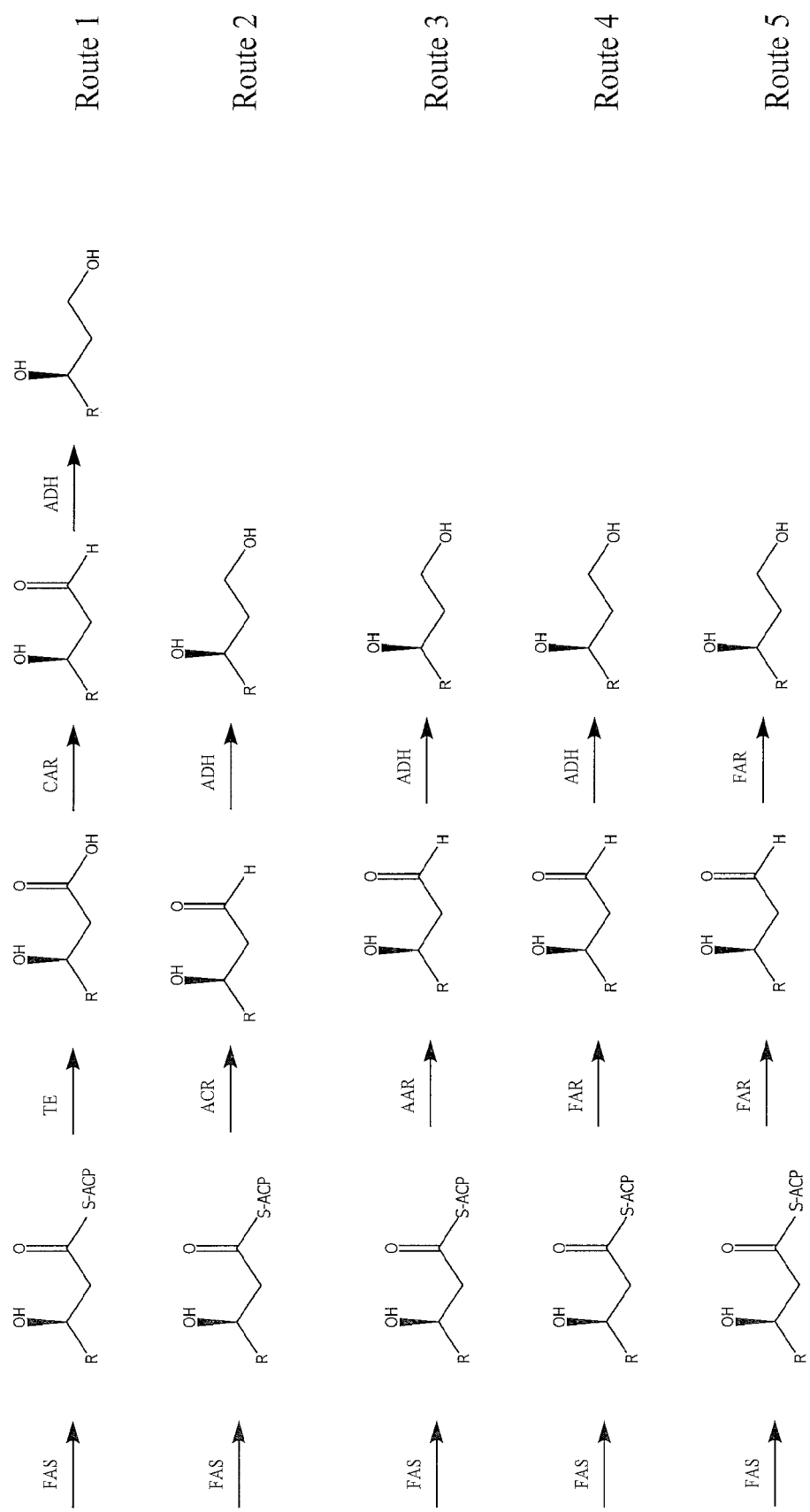
FIG. 10 shows (R)-1,3 fatty diol production. Route 1 uses enzymatic functionalities such as TE, CAR and ADH to produce right-handed chiral 1,3-diols. Route 2 uses TE, ACR and ADH to produce right-handed chiral 1,3-diols. Route 3 uses AAR and ADH to to produce right-handed chiral 1,3-diols. Route 4 uses FAR and ADH to produce right-handed chiral 1,3-diols. Route 5 uses FAR to produce right-handed chiral 1,3-diols.
Figure 11:
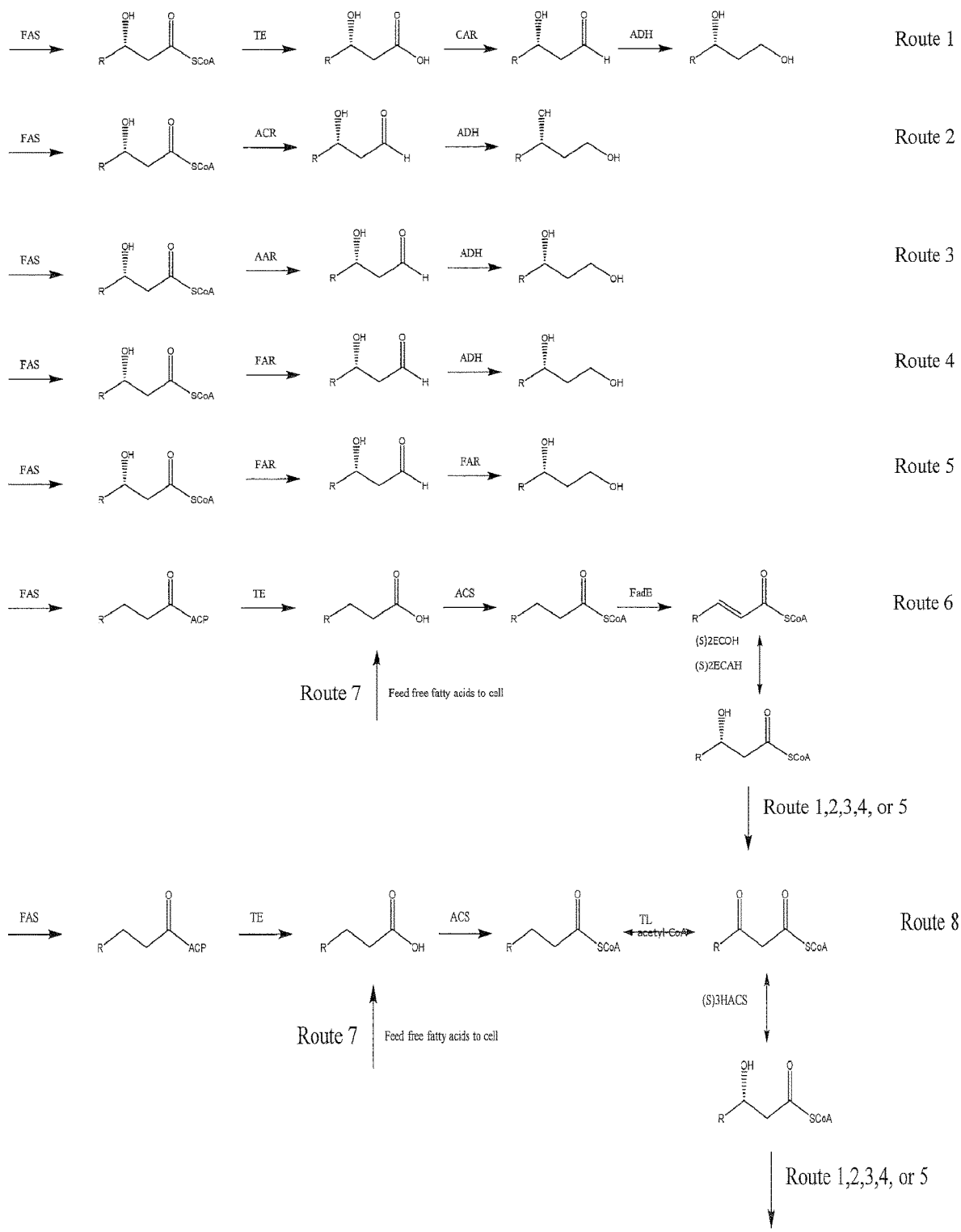
FIG. 11 shows (S)-1,3 fatty diol production. Route 1 uses enzymatic functionalities such as TE, CAR and ADH to produce left-handed chiral 1,3-diols. Route 2 uses ACR and ADH to produce left-handed chiral 1,3-diols. Route 3 uses AAR and ADH to produce left-handed chiral 1,3-diols. Route 4 uses FAR and ADH to produce left-handed 1,3-diols. Route 5 uses FAR to produce left-handed chiral 1,3-diols. Route 6 uses TE, ACS, FadE and (S)2ECOH to produce left-handed chiral 1,3-diols. Route 7 uses fatty acids and ACS to produce left-handed chiral 1,3-diols. Route 8 uses TE, ACS, TL and (S)3HACS to produce left-handed chiral 1,3-diols.

A unique aspect of 3-hydroxy fatty acid derivatives (e.g., 3-hydroxy fatty acids, 3-hydroxy fatty esters, 3-hydroxy fatty aldehydes, 3-hydroxy fatty alcohols, etc.), is that each molecule is chiral. The 3-hydroxy functionality is a stereo center, providing a point of chirality for each compound. Chirality can be a useful molecular attribute in defining molecular applications including, but not limited to, polymer performance, bioactivity, pharmaceutical potency, and the like. The stereo isomer of 3-hydroxy fatty acid derivatives depends on the selectivity of the fatty acid biosynthesis (FAS) from which it is produced. By manipulating which FAS enzymes are responsible for the 3-hydroxy fatty acid derivative synthesis, the chirality of the resulting 3-hydroxy fatty derivative can be controlled. For example, exploiting the native *E. coli* FAS for 1,3 fatty diol biosynthesis will produce the (R)-1,3 fatty diol, the chiral center of which is created by the activity of by (R)-3-hydroxyl acyl ACP-forming 3-ketoacyl-ACP reductase, catalyzed by FabG in *E. coli* (and homologues in other microorganisms). The (R)-3-hydroxylacyl ACP is a substrate for alcohol biosynthesis polypeptides including, but not limited to, those shown in routes 1-5 in FIG. 10, which convert it to (R)-1,3 fatty diol. Further, (S)-3-hydroxy acyl CoA is an intermediate in the degradation of fatty acids through the beta-oxidation pathway. Free fatty acids are converted to acyl-CoAs by acyl-CoA synthase, catalyzed by FadD in *E. coli* and homologues in other microorganisms; this is oxidized to trans-2-enoyl-CoA by fatty acyl-CoA dehydrogenase, catalyzed by FadE in *E. coli* and homologues in other microorganisms; this is then hydrated to (S)-3-hydroxy-acyl-CoA by 2-trans-enoyl-CoA hydratase/(S)-3-hydroxy-acyl-CoA dehydratase, catalyzed by FadB in *E. coli* and homologues in other microorganisms; this is then further oxidized to 3-keto-acyl-CoA by 3-keto-acyl-CoA dehydrogenase, also catalyzed by FadB in *E. coli* and homologues in other microorganisms; this is finally thiolyzed to acyl-CoA and Acetyl-CoA by 3-ketoacyl-CoA thiolase, catalyzed by FadA in *E. coli* and homologues in other microorganisms. A strain that is selectively disrupted in the (S)-3-hydroxy-acyl-CoA dehydrogenase activity of beta oxidation, for example, by a mutation of Histidine 450 in the *E. coli* FadB (or a functional homolog in or from a different microorganism), would accumulate (S)-3-hydroxy-acyl CoA when provided a free fatty acid (routes 6 and 7 in FIG. 11). Histidine 450 is the catalytic residue of L-3-hydroxyacyl Coenzyme A dehydrogenase associated with the large α-subunit of the multi-enzyme complex of fatty acid oxidation from *E. coli* (see He et al. (1996) *Biochemistry* 35(29):9625-9630). The (S)-3-hydroxy-acyl CoA could then be converted to (S)-1,3-fatty diol through the action of fatty alcohol forming polypeptides, such as those described in routes 1-5 in FIG. 11. The free fatty acid could be provided to the cell externally (route 7 in FIG. 11) or could be generated within the cell, for example by the hydrolysis of an acyl ACP by a thioesterase (route 6 in FIG. 11). In one embodiment, the acyl CoA intermediate in the above reactions is elongated to 3-ketoacyl-CoA by 3-ketoacyl-CoA thiolase (see route 8 in FIG. 11), catalyzed by FadA in *E. coli* and homologues in other microorganisms; this is then reduced by mutants of FadB which are selectively disrupted in their hydratase/dehydratase activity (for example, by a mutation of Glu 119 in *E. coli* FadB (or its homologue in related enzymes). This would result in the accumulation of (S)-3-hydroxylacyl-CoA, which could then be converted to (S)-1,3 fatty diols by fatty diol forming polypeptides such as those shown in routes 1-5 in FIG. 11. Glutamate-119 of the large alpha-subunit is the catalytic base in the hydration of 2-trans-enoyl-coenzyme A catalyzed by the multi-enzyme complex of fatty acid oxidation from *E. coli* (see He et al. (1997) *Biochemistry* 36(36):11044-11049). Glutamate 139 of the large alpha-subunit is the catalytic base in the dehydration of both D- and L-3-hydroxyacyl-coenzyme A but not in the isomerization of delta 3, delta 2-enoyl-coenzyme A catalyzed by the multi-enzyme complex of fatty acid oxidation from *E. coli* (see Yang et al. (1995) *Biochemistry* 34(19):6441-6447). In another embodiment, the acyl CoA intermediate in the above reactions is elongated to 3-ketoacyl CoA by 3-ketoacyl CoA thiolase, catalyzed by FadA in *E. coli* and homologues in other microorganisms, this is then reduced by (S)-3-hydroxyacyl-CoA dehydrogenases (e.g., from the EC 1.1.1.35) (Route 8 FIG. 11). This would result in the accumulation of (S)-3 hydroxylacyl CoA, which could then be converted to (S)-1,3 fatty diols by fatty diol forming polypeptides such as those shown in routes 1-5 in FIG. 11.

In order to engineer host cells to express certain enzymatic functionalities (see Table 1, infra) genetic modification can be made to the host cells. In some embodiments, a polynucleotide (or gene) sequence is provided to the host cell by way of a recombinant vector, which includes a promoter operably linked to the polynucleotide sequence. In certain embodiments, the promoter is a developmentally-regulated, an organelle-specific, a tissue-specific, an inducible, a constitutive, or a cell-specific promoter. In some embodiments, the recombinant vector includes at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. The expression vectors described herein include a polynucleotide sequence in a form suitable for expression of the polynucleotide sequence in a host cell. It will be appreciated by those skilled in the art that the design of the expression vector can depend on such factors as the choice of the host cell to be transformed, the level of expression of polypeptide desired, and the like. The expression vectors described herein can be introduced into host cells to produce polypeptides, including fusion polypeptides, encoded by the polynucleotide sequences as described above (supra). Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes including to increase expression of the recombinant polypeptide; to increase the solubility of the recombinant polypeptide; and to aid in the purification of the recombinant polypeptide by acting as a ligand in affinity purification. Often, in fusion expression vectors, a proteolytic cleavage site is introduced at the junction of the fusion moiety and the recombinant polypeptide. This allows separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX vector (Pharmacia Biotech, Inc., Piscataway, N.J.; Smith et al. (1988) *Gene* 67:31-40), pMAL vector (New England Biolabs, Beverly, Mass.), and pRITS vector (Pharmacia Biotech, Inc., Piscataway, N.J.), which fuse glutathione S-transferase (GST), maltose E binding protein, or protein A, respectively, to the target recombinant polypeptide.

Examples of inducible, non-fusion *E. coli* expression vectors include pTrc vector (Amann et al. (1988) *Gene* 69:301-315) and pET 11d vector (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains such as BL21(DE3) or HMS174(DE3) from a resident λ prophage harboring a T7 gn1 gene under the transcriptional control of the lacUV 5 promoter. Suitable expression systems for both prokaryotic and eukaryotic cells are well known in the art (see, e.g., Sambrook et al. (1989) Molecular Cloning: A Laboratory Manual, second edition, Cold Spring Harbor Laboratory). Examples of inducible, non-fusion *E. coli* expression vectors include pTrc vector (Amann et al. (1988) *Gene* 69:301-315) and PET 11d vector (Studier et al. (1990) Gene Expression Technology: Methods in Enzymology 185, Academic Press, San Diego, Calif., pp. 60-89). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra). For stable transformation of bacterial cells, it is known that (depending upon the expression vector and transformation technique used) a certain fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug. The engineered or recombinant host cell as described herein is a cell used to produce a fatty acid derivative composition such as a fatty diol composition. In any of the aspects of the disclosure described herein, the host cell can be selected from a eukaryotic plant, bacteria, algae, cyanobacterium, green-sulfur bacterium, green non-sulfur bacterium, purple sulfur bacterium, purple non-sulfur bacterium, extremophile, yeast, fungus, engineered organisms thereof, or a synthetic organism. In some embodiments, the host cell is light dependent or fixes carbon. In some embodiments, the host cell has autotrophic activity. Various host cells can be used to produce fatty diols, as described herein.

The host cells or microorganisms of the disclosure include host strains or host cells that can be genetically engineered or modified to contain alterations in order to test the efficiency of specific enzymatic activities. Various optional genetic manipulations and alterations can be used interchangeably from one host cell to another, depending on what native enzymatic pathways are present in the original host cell. A host strain may encompasses a number of genetic alterations in order to test specific variables, including but not limited to, culture conditions including fermentation components, carbon source (e.g., feedstock), temperature, pressure, reduced culture contamination conditions, and oxygen levels.

In one embodiment, a host strain encompasses an optional attenuation or deletion of one or more enzymes involved in fatty acid beta-oxidation and/or phage attachment sites. These genetic modifications are designed to decrease the intracellular degradation of fatty acids and to increase resistance to bacteriophage. In one embodiment, the host strain is *E. coli* and the genetic modification is an attenuation or deletion of fadE and/or fhuA. Acyl-CoA dehydrogenase (FadE in *E. coli*) is an enzyme that is important for metabolizing fatty acids. It catalyzes the second step in fatty acid degradation (beta-oxidation), which is the process of metabolizing fatty acid thioesters (acyl-CoAs) into acetyl-CoA molecules and NAD(P)H. More specifically, the second step of the β-oxidation cycle of fatty acid degradation in bacteria is the oxidation of acyl-CoA to 2-enoyl-CoA, which is catalyzed by FadE. When *E. coli* or other bacteria lack or are attenuated in FadE or fatty acyl CoA dehydrogenase, they grow poorly or not at all on fatty acids as a carbon source. The inability to utilize fatty acids of any chain length is consistent with the reported phenotype of fadE strains, i.e., fadE mutant strains where FadE function is disrupted. The fadE gene can be optionally knocked out or attenuated to assure that acyl-CoAs, which may be intermediates in a fatty acid derivative pathway, can accumulate in the cell such that all acyl-CoAs can be efficiently converted to fatty acid derivatives. However, fadE attenuation may be optional when sugar is used as a carbon source under non-limiting conditions since under such condition expression of FadE may be repressed and FadE therefore may only be present in small amounts and not able to efficiently compete with ester synthase or other enzymes for acyl-CoA substrates. Under these circumstances one would consider FadE as being repressed due to catabolite repression. *E. coli* and many other microbes prefer to consume sugar over fatty acids, so when both sources are available, sugar would be expected to be consumed first, as a result of the repression of the fad regulon (see D. Clark, *J Bacteriol.* (1981) 148(2):521-6). Moreover, the absence of sugars and the presence of fatty acids induce FadE expression. Acyl-CoA intermediates could be lost to the beta oxidation pathway since the proteins expressed by the fad regulon (including FadE) would be up-regulated and would efficiently compete for acyl-CoAs. Thus, it can be beneficial to have the fadE gene knocked out or attenuated. Since carbon sources may be sugar based, it is optional to attenuate FadE.

For example, in *E. coli*, either the fadE gene (encoding acyl-CoA dehydrogenase) or the fadD gene (encoding acyl-CoA synthetase) can be deleted. Such strains cannot degrade fatty acids or only very poorly, thus, increasing the availability of fatty acids within the cell. Such fatty acids then become available for an increased conversion to product such as fatty acid derivatives. Fatty acids can also be made available by deleting other fatty acid degradation enzymes such as fadA or fadB. The deletion of any of these genes is optional and can be implemented when free fatty acids are exogenously supplied or are intermediates of a product pathway. Table 1 (infra) provides a comprehensive list of enzymatic activity within the metabolic pathways, including various fatty acid degradation enzymes that can be attenuated to increase the availability of fatty acids in a host strain.

In *E. coli*, the gene fhuA codes for the TonA protein, which is an energy-coupled transporter and receptor in the outer membrane of *E. coli* (V. Braun (2009) *J Bacteriol.* 191(11):3431-3436). Its deletion is optional. The fhuA deletion allows the cell to become more resistant to phage attack, which can be deleterious in commercial fermentations. Thus, it may be desirable to delete fhuA in a host cell that is likely subject to potential contamination during fermentation runs. Similarly, homologous proteins in other organisms as well as other phage attachment sites are potential candidates for deletion to improve phage resistance.

In another embodiment, the host strain (supra) also encompasses optional overexpression of one or more of the following genes including fadR, fabA, fabD, fabG, fabH, fabV, and/or fabF. Examples of such genes are fadR from *Escherichia coli*, fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). The overexpression of one or more of these genes, which code for enzymes and regulators in fatty acid biosynthesis, can serve to increase the titer of fatty-acid derivative intermediates including fatty aldehydes as well as end products such as fatty diols under various culture conditions.

In one embodiment, *E. coli* strains are used as host cells for the production of fatty diols. These host cells can include optional overexpression of one or more biosynthesis genes (i.e., genes coding for enzymes and regulators of fatty acid biosynthesis) that can further increase or enhance the titer of fatty-acid derivative compounds such as fatty acid derivative intermediates (e.g., fatty aldehydes) and end products (e.g., fatty diols, fatty alcohols) under various culture conditions including, but not limited to, fadR, fabA, fabD, fabG, fabH, fabV and/or fabF. Examples of genetic alterations include fadR from *Escherichia coli*, fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). In some embodiments, synthetic operons that carry these biosynthetic genes can be engineered and expressed in cells in order to test fatty acid derivative intermediate overexpression under various culture conditions and/or to further enhance fatty diol production. Such synthetic operons contain one or more biosynthetic gene. The ifab138 operon, for example, is an engineered operon that contains optional fatty acid biosynthetic genes, including fabV from *Vibrio cholera*, fabH from *Salmonella typhimurium*, fabD from *S. typhimurium*, fabG from *S. typhimurium*, fabA from *S. typhimurium* and/or fabF from *Clostridium acetobutylicum* that can be used to facilitate overexpression of fatty acid derivative and intermediates in order to test specific culture conditions. One advantage of such synthetic operons is that the rate of fatty acid derivative production (e.g., fatty acid, fatty aldehyde, fatty alcohol, fatty diol, etc.) can be further increased or enhanced in cells containing them.

In some embodiments, the host cells or microorganisms that are used to produce acyl thioesters (such as acyl-CoA or acyl-ACP) and biosynthetic enzymes (e.g., TE, CAR, AR, ADH, ACC, AAR, FAR, ACR; see also FIGS. 1 and 3 as well as FIGS. 8-11) will further express genes that encompass certain enzymatic activities that can increase the production to one or more particular fatty acid derivatives such as fatty acids, 3-hydroxy fatty acids, fatty alcohols, 1,3 fatty diols, fatty aldehydes, 3-hydroxy fatty aldehydes, and the like. In one embodiment, the host cell has thioesterase (TE) activity (EC 3.1.2.- or EC 3.1.2.14 or EC 3.1.1.5) for the production of fatty acids and 3-hydroxy fatty acids which can be increased by overexpressing the gene. In another embodiment, the host cell has a thioesterase (TE) activity (EC 3.1.2.- or EC 3.1.2.14 or EC 3.1.1.5) and carboxylic acid reductase (CAR) (EC 6.2.1.3 or EC 1.2.1.42 or EC 1.2.99.6) activity for the production of fatty aldehydes and/or 3-hydroxy fatty aldehydes. In another embodiment, the host cell has a thioesterase (TE) activity (EC 3.1.2.- or EC 3.1.2.14 or EC 3.1.1.5) and carboxylic acid reductase (CAR) activity (EC 6.2.1.3 or EC 1.2.1.42 or EC 1.2.99.6) and alcohol dehydrogenase (ADH)/aldehyde reductase (AR) activity (EC 1.1.1.-) for the production of fatty alcohols and/or fatty diols. In another embodiment, the host cell has acyl-ACP reductase (AAR) activity (EC 1.2.1.80 or EC 1.2.1.42) for the production of fatty aldehydes and/or 3-hydroxy-fatty aldehydes. In another embodiment, the host cell has acyl-ACP reductase (AAR) activity (EC 1.2.1.80 or EC 1.2.1.42) and alcohol dehydrogenase (ADH)/aldehyde reductase (AR) activity (EC 1.1.1.-) for the production of fatty alcohols and/or fatty diols. Combination of genes can be overexpressed or underexpressed by engineering microbes accordingly. In one embodiment, one or more of the overexpressed genes are endogenous. In another embodiment, one or more of the overexpressed genes are exogenous.

In alternative embodiments, the host cell has acyl-ACP reductase (AAR) activity (EC 1.2.1.80 or EC 1.2.1.42) and/or acyl ACP/acyl CoA reductase (AAR/ACR) activity (EC 1.2.1.80 or EC 1.2.1.42 or EC 1.2.1.50) and/or alcohol dehydrogenase activity (E.C. 1.1.-.-.) and/or fatty alcohol forming acyl-CoA/Acyl ACP reductase (FAR) activity (EC 1.1.1.-) and/or carboxylic acid reductase (CAR) activity (EC 6.2.1.3 or EC 1.2.1.42 or EC 1.2.99.6) and/or thioesterase (TE) activity (EC 3.1.2.- or EC 3.1.2.14 or EC 3.1.1.5) for the production of fatty alcohols. In other alternative embodiments, the host cell has acyl-CoA reductase activity (EC 1.2.1.50) and acyl-CoA synthase (FadD) activity (EC 2.3.1.86) and thioesterase (TE) activity (EC 3.1.2.- or EC 3.1.2.14 or EC 3.1.1.5) for the production of fatty alcohols. The expression of these alternative enzymatic activities in microorganisms and microbial cells is taught by U.S. Pat. Nos. 8,097,439; 8,110,093; 8,110,670; 8,183,028; 8,268,599; 8,283,143; 8,232,924; 8,372,610; and 8,530,221, which are incorporated herein by reference. In other embodiments, the host cells or microorganisms that are used to produce acyl-ACP and/or acyl-CoA and other biosynthetic enzymes will include certain native enzyme activities that are upregulated or overexpressed in order to produce one or more particular fatty acid derivative such as a fatty aldehyde and/or fatty alcohol and/or fatty diol. In one embodiment, the host cell has a native thioesterase (TE) activity for the production of fatty acids which can be increased by overexpressing the thioesterase gene.

The present disclosure includes host strains or microorganisms that express genes that code for biosynthetic enzymes (supra). The recombinant host cells produce fatty acid derivative intermediates such as fatty aldehydes and fatty acid derivative end products such as fatty alcohols and/or fatty diols and compositions and blends thereof. The fatty acid derivative end products are typically recovered from the culture medium and/or are isolated from the host cells. In one embodiment, the fatty diols and/or fatty alcohols are recovered from the culture medium (extracellular). In another embodiment, the fatty diols and/or fatty alcohols are isolated from the host cells (intracellular). In another embodiment, the fatty diols and/or fatty alcohols are recovered from the culture medium and isolated from the host cells. In another embodiment, the fatty diols and/or fatty alcohols are extracellular and associated with the host cells and are isolated from the host cells. The fatty diol composition produced by a host cell can be analyzed using methods known in the art, for example, GC-FID, in order to determine the distribution of particular fatty diols as well as chain lengths and degree of saturation of the components of the fatty diol compositions.

Examples of host cells that function as microorganisms (e.g., microbial cells), include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Synechococcus, Synechocystis, Lactococcus, Chrysosporium, Saccharomyces, Stenotrophamonas, Schizosaccharomyces, Yarrowia,* or *Streptomyces.* In some embodiments, the host cell is a Gram-positive bacterial cell. In other embodiments, the host cell is a Gram-negative bacterial cell. In some embodiments, the host cell is an *E. coli* cell. In some embodiment, the host cell is an *E. coli* B cell, an *E. coli* C cell, an *E. coli* K cell, or an *E. coli* W cell. In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In still other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In yet other embodiments, the host cell is a *Streptomyces lividans* cell or a *Streptomyces murinus* cell. In yet other embodiments, the host cell is an *Actinomycetes* cell. In some embodiments, the host cell is a *Saccharomyces cerevisiae* cell. In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Arabidopsis*

*thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridium thermocellum, Penicillium chrysogenum, Pichia pastoris, Saccharomyces cerevisiae, Schizosaccharomyces pombe, Pseudomonas fluorescens, Pseudomonas putida* or *Zymomonas mobilis*. In one particular embodiment, the microbial cell is from a cyanobacteria including, but not limited to, *Prochlorococcus, Synechococcus, Synechocystis, Cyanothece*, and *Nostoc punctiforme*. In another embodiment, the microbial cell is from a specific cyanobacterial species including, but not limited to, *Synechococcus elongatus* PCC7942, *Synechocystis* sp. PCC6803, and *Synechococcus* sp. PCC7001.

Recombinant Host Cells Engineered to Produce 1,3-Diols

Figure 2:
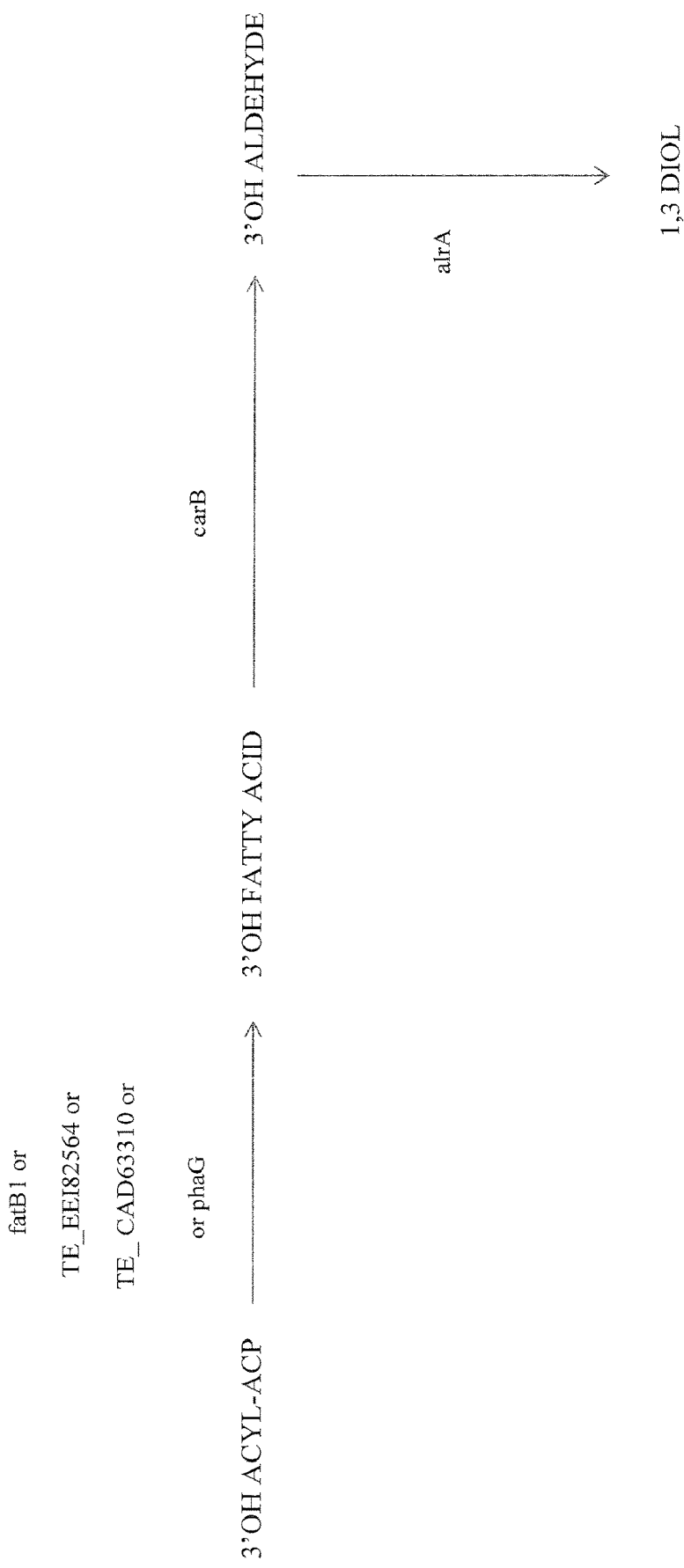
FIG. 2 depicts an exemplary pathway for making 1,3-diols, providing examples of enzymatic functionalities for illustrative purposes.

The present disclosure identifies polynucleotides that encode polypeptides of enzymatic function in order to modify enzymatic pathways for the production of desirable compounds such as fatty diols (e.g., 1,3-diols). These polypeptides, which are identified herein by Enzyme Accession Numbers (EC Numbers, see Table 1, infra), are useful for engineering fatty acid pathways that lead to production of fatty diols. More specifically, FIGS. 1-3, and 8-11 depict pathways that are engineered to produce 1,3-diols. As shown, a 3' hydroxy acyl carrier protein (ACP) carrying an acyl intermediate (acyl-ACP or a 3-hydroxy acyl-ACP) can be converted to a 1,3-diol, employing a 3' hydroxy fatty acid (3' OH FA) and a 3' hydroxy fatty aldehyde (3' OH fatty aldehyde) as intermediates. In one embodiment, engineered pathways are depicted in FIGS. 1-3 and 8-11 that produces 1,3-diols. Herein, a simple carbon source such as glucose is first converted to an 3' hydroxy acyl-ACP by the microbial organism (e.g., *Escherichia, Bacillus, Lactobacillus, Rhodococcus, Synechococcus, Synechoystis, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, or *Streptomyces*). In some embodiments, the universal and highly conserved acyl-ACP or 3' hydroxy acyl-ACP is produced by the native pathway of the microbial organism. In one embodiment, 3' hydroxy Acyl-ACP can be used to initiate the engineered pathway. For example, 3' hydroxy acyl-ACP can be converted to an intermediate such as 3' OH FA by an enzyme that has thioesterase (TE) activity (see Table 2, infra). The intermediate 3' OH FA can then be converted to another intermediate such as 3' OH aldehyde by an enzyme that has carboxylic acid reductase (CAR) activity (see Table 3, infra). An enzyme that has alcohol dehydrogenase (ADH) or aldehyde reductase (AR) activity (see Table 4, infra) can then convert the 3' OH aldehyde into a 1,3-diol. In order to further illustrate such a pathway, FIG. 2 provides examples of specific enzymes that have the thioesterase activity (e.g., fatB1, tesA, phaG); CAR activity (e.g., carB); and ADH/AR activity (e.g., alrA). Additional examples of thioesterase (TE) enzymes that can carry out the reaction of converting an 3'OH acyl-ACP to a 3' OH FA are shown in Table 2. In one embodiment, the genes encoding these thioesterases are tesA, tesB, fatB, fatB1, fatB2, fatB3, TE_EEI82564, TE_CAD63310, and phaG. In another embodiment, the genes encoding these thioesterases are TE_EEI82564 and/or TE_CAD63310, which have not previously been associated with the ability to convert 3'OH acyl-ACPs to 3' OH FAs (e.g., see Jing et al. (2011) *BMC Biochemistry* 12(44):1471-2091). Additional examples of CAR enzymes that can carry out the reaction of converting a 3' OH FA to a 3' OH aldehyde are shown in Table 3. In one embodiment, the gene encoding the CAR enzyme is carB. Additional examples of ADH/AR enzymes that can carry out the reaction of converting a 3' OH aldehyde to a 1,3-diol are shown in Table 4. In one embodiment, the genes encoding these ADH/AR enzymes are alrA and/or yqhD.

Figure 3:
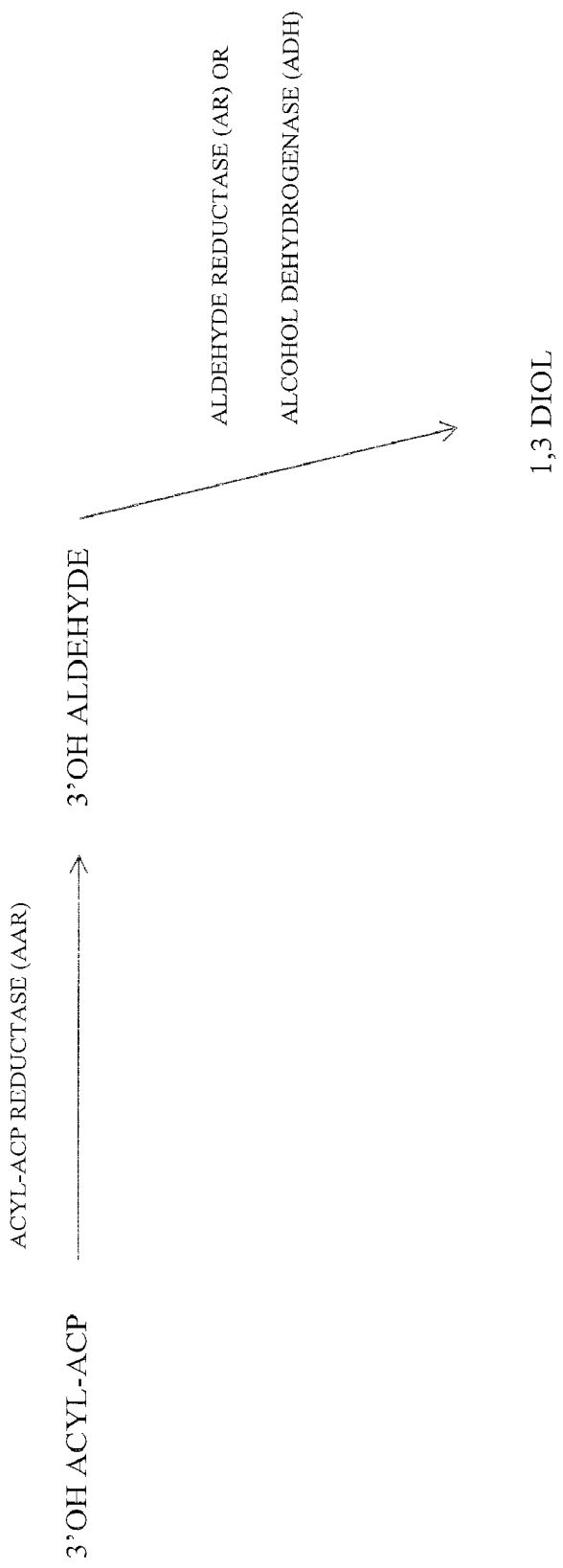
FIG. 3 shows an alternative pathway for making 1,3-diols, including enzymatic functionalities.

In another embodiment, an engineered pathway is depicted in FIG. 3 that also produces 1,3-diols. Similarly, a simple carbon source such as glucose is first converted to an 3' hydroxyl acyl-ACP by the microbial organism (e.g., *Escherichia, Bacillus, Lactobacillus, Rhodococcus, Synechococcus, Synechoystis, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, or *Streptomyces*). In some embodiments, the universal and highly conserved 3' hydroxyl acyl-ACP is produced by the native pathway of the microbial organism. As noted above, 3' hydroxyl acyl-ACP can be used to initiate the engineered pathway. For example, 3' hydroxyl acyl-ACP is converted to an intermediate such as 3' OH fatty aldehyde by an enzyme that has acyl-ACP reductase (AAR) activity (see Table 1). The production of fatty alcohols and/or fatty aldehydes by AAR may be enhanced through the heterologous expression of a gene called accABCD which codes for an acetyl-CoA carboxylase. Examples of AAR enzymes that can carry out the reaction of converting a 3'OH acyl-ACPs to a 3' OH aldehyde include, but are not limited to, an enzyme from *Synechococcus elongatus, Cyanothece* sp., *Synechosystis* sp., and *Prochlorococcus marinus*. An enzyme that has alcohol dehydrogenase (ADH) or aldehyde reductase (AR) activity (see Table 4) can then convert the 3' OH aldehyde into a fatty diol such as 1,3-diol. Thus, the present disclosure provides recombinant microorganisms that can efficiently and selectively produce fatty diols including 1,3-diols in vivo. It should be noted that most cells natively produce enzymes capable of reducing aldehydes, as they can be cytotoxic. Accordingly, the heterologous expression of AR and ADH may not be required for the production of fatty alcohols and diols, but they may improve the efficiency with which fatty alcohols and diols are produced.

In addition, polynucleotides that code for polypeptides with fatty acid degradation enzyme activity can be optionally attenuated in the host cells. Non-limiting examples of such polypeptides are acyl-CoA synthetase (such as *E. coli* FadD) and acyl-CoA dehydrogenase (such as *E. coli* FadE). Table 1 provides a comprehensive list of enzymatic activities in exemplary metabolic pathways, including various fatty acid degradation enzymes that can be optionally attenuated according to methods known in the art (see, e.g., U.S. Pat. No. 8,283,143, supra). For example, FadR (see Table 1) is a key regulatory factor involved in fatty acid degradation and fatty acid biosynthetic pathways in *E. coli* (Cronan et al., *Mol. Microbiol.*, 29(4): 937-943 (1998)). The *E. coli* enzyme FadD (see Table 1) and the fatty acid transport protein FadL are components of a fatty acid uptake system. FadL and its homologs mediate transport of fatty acids into the bacterial cell, and FadD and its homologs mediate formation of acyl-CoA esters. An alternative, heterologous uptake system for fatty acids and fatty acid derivatives is the outer membrane protein AlkL from *Pseudomonas* (Julsing et al. (2012)

Appl. Environ. Microbiol. 78:5724-5733). When no other carbon source is available, exogenous fatty acids are taken up by bacteria and converted to acyl-CoA esters, which can bind to the transcription factor FadR and depress the expression of the fad genes that encode proteins responsible for fatty acid transport (FadL), activation (FadD), and β-oxidation (FadA, FadB, and FadE). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that can result in different end-products (Caviglia et al., *J. Biol. Chem.*, 279(12): 1163-1169 (2004)). FadR and/or FabB and their functional homologs can enhance the production of fatty acid derivatives in host cells (e.g., *E. coli*) but their overexpression is optional. Herein, it is contemplated that FabB overexpression may increase the rate of elongation (fatty acid chain synthesis), and FadR overexpression may increase the expression of FabA and FabB. The latter is possible because FadR is contemplated to be a positive regulator of FabA and FabB.

TABLE 1

Enzymatic Activities

| Gene Designation | Source Organism | Enzyme Name | Accession # | EC Number | Exemplary Use |
|---|---|---|---|---|---|
| Fatty Acid Production Increase | | | | | |
| accA | *Escherichia coli* (*E. coli*), Lactococci | Acetyl-CoA carboxylase, subunit A (carboxyltransferase alpha) | AAC73296, NP_414727 | 6.4.1.2 | Increase Malonyl-CoA production |
| accB | *E. coli*, Lactococci | Acetyl-CoA carboxylase, subunit B (BCCP: biotin carboxyl carrier protein) | NP_417721 | 6.4.1.2 | increase Malonyl-CoA production |
| accC | *E. coli*, Lactococci | Acetyl-CoA carboxylase, subunit C (biotin carboxylase) | NP_417722 | 6.4.1.2, 6.3.4.14 | increase Malonyl-CoA production |
| accD | *E. coli*, Lactococci | Acetyl-CoA carboxylase, subunit D (carboxyltransferase beta) | NP_416819 | 6.4.1.2 | increase Malonyl-CoA production |
| fadD | *E. coli* W3110 | acyl-CoA synthase | AP_002424 | 2.3.1.86, 6.2.1.3 | increase Fatty acid production |
| fabA | *E. coli* K12 | β-hydroxydecanoyl thioester dehydratase/isomerase | NP_415474 | 4.2.1.60 | increase fatty acyl-ACP/CoA production |
| fabB | *E. coli* | 3-oxoacyl-[acyl-carrier-protein] synthase I | BAA16180 | 2.3.1.41 | increase fatty acyl-ACP/CoA production |
| fabD | *E. coli* K12 | [acyl-carrier-protein] S-malonyltransferase | AAC74176 | 2.3.1.39 | increase fatty acyl-ACP/CoA production |
| fabF | *E. coli* K12 | 3-oxoacyl-[acyl-carrier-protein] synthase II | AAC74179 | 2.3.1.179 | increase fatty acyl-ACP/CoA production |
| fabG | *E. coli* K12 | 3-oxoacyl-[acyl-carrier protein] reductase | AAC74177 | 1.1.1.100 | increase fatty acyl-ACP/CoA production |
| fabH | *E. coli* K12 | 3-oxoacyl-[acyl-carrier-protein] synthase III | AAC74175 | 2.3.1.180 | increase fatty acyl-ACP/CoA production |
| fabI | *E. coli* K12 | enoyl-[acyl-carrier-protein] reductase | NP_415804 | 1.3.1.9 | increase fatty acyl-ACP/CoA production |
| fabR | *E. coli* K12 | Transcriptional Repressor | NP_418398 | none | modulate unsaturated fatty acid production |
| fabV | *Vibrio cholerae* | enoyl-[acyl-carrier-protein] reductase | YP_001217283 | 1.3.1.9 | increase fatty acyl-ACP/CoA production |
| fabZ | *E. coli* K12 | (3R)-hydroxymyristol acyl carrier protein dehydratase | NP_414722 | 4.2.1.— | increase fatty acyl-ACP/CoA production |
| fadE | *E. coli* K13 | acyl-CoA dehydrogenase | AAC73325 | 1.3.99.3, 1.3.99.— | reduce fatty acid degradation |
| fadD | *E. coli* K12 | acyl-CoA synthetase | NP_416319 | 6.2.1.3 | reduce fatty acid degradation |
| fadA | *E. coli* K12 | 3-ketoacyl-CoA thiolase | YP_02627 | 2.3.1.16 | reduce fatty acid degradation |
| fadB | *E. coli* K12 | enoyl-CoA hydratase, 3-OH acyl-CoA epimerase/dehydrogenase | NP_418288 | 4.2.1.17, 5.1.2.3, 1.1.1.35 | reduce fatty acid degradation |
| fadR | *E. coli* | transcriptional regulatory protein | NP_415705 | none | Block or reverse fatty acid degradation |
| Chain Length Control | | | | | |
| tesA (with or without leader sequence) | *E. coli* | thioesterase - leader sequence includes amino acids 1-26 | P0ADA1 | 3.1.2.2.—, 3.1.1.5, 3.1.2.14 | C18 Chain Length |
| tesA (without leader sequence) | *E. coli* | thioesterase | AAC73596, NP_415027 | 3.1.2.2.—, 3.1.1.5, 3.1.2.14 | C18:1 Chain Length |
| tesA (mutant of *E. coli* thioesterase I complexed | *E. coli* | thioesterase | L109P | 3.1.2.2.—, 3.1.1.5, 3.1.2.14 | <C18 Chain Length |

TABLE 1-continued

Enzymatic Activities

| Gene Designation | Source Organism | Enzyme Name | Accession # | EC Number | Exemplary Use |
|---|---|---|---|---|---|
| with octanoic acid) | | | | | |
| fatB1 | Umbellularia californica | thioesterase | Q41635 | 3.1.2.14 | C12:0 Chain Length |
| fatB2 | Cuphea hookeriana | thioesterase | AAC49269 | 3.1.2.14 | C8:0-C10:0 Chain Length |
| fatB3 | Cuphea hookeriana | thioesterase | AAC72881 | 3.1.2.14 | C14:0-C16:0 Chain Length |
| fatB | Cinnamomum camphora | thioesterase | Q39473 | 3.1.2.14 | C14:0 Chain Length |
| fatB | Arabidopsis thaliana | thioesterase | CAA85388 | 3.1.2.14 | C16:1 Chain Length |
| fatA1 | Helianthus annuus | thioesterase | AAL79361 | 3.1.2.14 | C18:1 Chain Length |
| fatA | Arabidopsis thaliana | thioesterase | NP_189147, NP_193041 | 3.1.2.14 | C18:1 Chain Length |
| fatA | Brassica juncea | thioesterase | CAC39106 | 3.1.2.14 | C18:1 Chain Length |
| fatA | Cuphea hookeriana | thioesterase | AAC72883 | 3.1.2.14 | C18:1 Chain Length |
| tes | Photbacterium profundum | thioesterase | YP_130990 | 3.1.2.2., 3.1.2.14 | Chain Length |
| tesB | E. coli | thioesterase | NP_414986 | 3.1.2.2. | Chain Length |
| fadM | E. coli | thioesterase | NP_414977 | 3.1.2.2. | Chain Length |
| yciA | E. coli | thioesterase | NP_415769 | 3.1.2.2. | Chain Length |
| ybgC | E. coli | thioesterase | NP_415264 | 3.1.2.2. | Chain Length |
| phaG | Pseudomonas putida | Thioesterase, 3-hydroxyacyl-CoA-acyl carrier protein transferase | AAN67031 | 3.1.2.14, | C6 to C12 chain length |
| Saturation Level Control | | | | | |
| Sfa | E. coli | Suppressor of fabA | AAN79592, AAC44390 | none | increase monounsaturated fatty acids |
| fabA | E. coli K12 | β-hydroxydecanoyl thioester dehydratase/isomerase | NP_415474 | 4.2.1.60 | produce unsaturated fatty acids |
| GnsA | E. coli | suppressors of the secG null mutation | ABD18647.1 | none | increase unsaturated fatty acid esters |
| GnsB | E. coli | suppressors of the secG null mutation | AAC74076.1 | none | increase unsaturated fatty acid esters |
| fabB | E. coli | 3-oxoacyl-[acyl-carrier-protein] synthase I | BAA16180 | 2.3.1.41 | modulate unsaturated fatty acid production |
| des | Bacillus subtilis | D5 fatty acyl desaturase | O34653 | 1.14.19 | modulate unsaturated fatty acid production |
| Ester Production | | | | | |
| AT3G51970 | Arabidopsis thaliana | long-chain-alcohol O-fatty-acyltransferase | NP_190765 | 2.3.1.26 | ester production |
| ELO1 | Pichia angusta | Fatty acid elongase | BAD98251 | 2.3.1.— | produce very long chain length fatty acids |
| plsC | Saccharomyces cerevisiae | acyltransferase | AAA16514 | 2.3.1.51 | ester production |
| DAGAT/DGAT | Arabidopsis thaliana | diacylglycerol acyltransferase | AAF19262 | 2.3.1.20 | ester production |
| hWS | Homo sapiens | acyl-CoA wax alcohol acyltransferase | AAX48018 | 2.3.1.20 | ester production |
| aft1 | Acinetobacter sp. ADP1 | bifunctional wax ester synthase/acyl-CoA:diacylglycerol acyltransferase | AAO17391 | 2.3.1.20 | ester production |
| ES9 | Marinobacter hydrocarbonoclasticus | wax ester synthase | ABO21021 | 2.3.1.20 | ester production |
| mWS | Simmondsia chinensis | wax ester synthase | AAD38041 | 2.3.1.— | ester production |
| Fatty Alcohol Output | | | | | |
| | | thioesterases (see above) | | | increase fatty acid/fatty alcohol production |
| BmFAR | Bombyxmori | FAR (fatty alcohol forming acyl-CoA reductase) | BAC79425 | 1.2.1.50, 1.2.1.84 | convert acyl-CoA to fatty alcohol |
| acr1 | Acinetobacter sp. ADP1 | acyl-CoA reductase | YP_047869 | 1.2.1.42, 1.2.1.50 | reduce fatty acyl-CoA to fatty aldehydes |
| yqhD | E. coli W3110 | alcohol dehydrogenase | AP_003562 | 1.1.1.— | reduce fatty aldehydes to fatty alcohols; increase fatty alcohol production |
| alrA | Acinetobacter sp. ADP1 | alcohol dehydrogenase | CAG70252 | 1.1.1.— | reduce fatty aldehydes to fatty alcohols |
| GTNG_1865 | Geobacillus thermodenitrificans NG80-2 | Long-chain aldehyde dehydrogenase | YP_001125970 | 1.2.1.3 | reduce fatty aldehydes to fatty alcohols |
| AAR | Synechococcus elongatus | Acyl-ACP reductase | YP_400611 | 1.2.1.42 | reduce fatty acyl-ACP/CoA to fatty aldehydes |

TABLE 1-continued

Enzymatic Activities

| Gene Designation | Source Organism | Enzyme Name | Accession # | EC Number | Exemplary Use |
|---|---|---|---|---|---|
| carB | *Mycobacterium smegmatis* | carboxylic acid reductase protein | YP_889972 | 6.2.1.3, 1.2.1.42 | reduce fatty acids to fatty aldehyde |
| FadD | *E. coli* K12 | acyl-CoA synthetase | NP_416319 | 6.2.1.3 | activates fatty acids to fatty acyl-CoAs |
| atoB | *Erwinia carotovora* | acetyl-CoA acetyltransferase | YP_049388 | 2.3.1.9 | production of butanol |
| hbd | *Butyrivibrio fibrisolvens* | Beta-hydroxybutyryl-CoA dehydrogenase | BAD51424 | 1.1.1.157 | production of butanol |
| CPE0095 | *Clostridium perfringens* | crotonasebutyryl-CoA dehydryogenase | BAB79801 | 4.2.1.55 | production of butanol |
| bcd | *Clostridium beijerinckii* | butyryl-CoA dehydryogenase | AAM14583 | 1.3.99.2 | production of butanol |
| ALDH | *Clostridium beijerinckii* | coenzyme A-acylating aldehyde dehydrogenase | AAT66436 | 1.2.1.3 | production of butanol |
| AdhE | *E. coli* CFT073 | aldehyde-alcohol dehydrogenase | AAN80172 | 1.1.1.1, 1.2.1.10 | production of butanol |

Fatty Alcohol Acetyl Ester Output

| | | thioesterases (see above) | | | modify output |
|---|---|---|---|---|---|
| acr1 | *Acinetobacter* sp. ADP1 | acyl-CoA reductase | YP_047869 | 1.2.1.42, 1.2.1.50 | modify output |
| yqhD | *E. Coli* K12 | alcohol dehydrogenase | AP_003562 | 1.1.—.— | modify output |
| AAT | *Fragaria* x *ananassa* | alcohol O-acetyltransferase | AAG13130 | 2.3.1.84 | modify output |

Terminal Olefin Output

| OleT | *Jeotgalicoccus* sp. | Fatty acid decarboxylase | HQ709266 | 1.11.2.4 | decarboxylate fatty acids |
|---|---|---|---|---|---|

Product Export

| AtMRP5 | *Arabidopsis thaliana* | Arabidopsis thaliana multidrug resistance-associated | NP_171908 | none | modify product export amount |
|---|---|---|---|---|---|
| AmiS2 | *Rhodococcus* sp. | ABC transporter AmiS2 | JC5491 | none | modify product export amount |
| AtPGP1 | *Arabidopsis thaliana* | Arabidopsis thaliana p glycoprotein 1 | NP_181228 | none | modify product export amount |
| AcrA | *Candidatus Protochlamydia amoebophila* UWE25 | putative multidrug-efflux transport protein acrA | CAF23274 | none | modify product export amount |
| AcrB | *Candidatus Protochlamydia amoebophila* UWE25 | probable multidrug-efflux transport protein, acrB | CAF23275 | none | modify product export amount |
| TolC | *Francisella tularensis* subsp. *novicida* | Outer membrane protein [Cell envelope biogenesis, | ABD59001 | none | modify product export amount |
| AcrE | *Shigella sonnei* Ss046 | transmembrane protein affects septum formation and cell membrane permeability | YP_312213 | none | modify product export amount |
| AcrF | *E. coli* | Acriflavine resistance protein F | P24181 | none | modify product export amount |
| tll1619 | *Thermosynechococcus elongatus* [BP-1] | multidrug efflux transporter | NP_682409.1 | none | modify product export amount |
| tll0139 | *Thermosynechococcus elongatus* [BP-1] | multidrug efflux transporter | NP_680930.1 | none | modify product export amount |
| AlkL | *Pseudomonas putida* | Outer membrane protein | YP_009076010 | none | modify product export amount |

Fermentation

| replication checkpoint genes | | | | | increase output efficiency |
|---|---|---|---|---|---|
| umuD | *Shigella sonnei* Ss046 | DNA polymerase V, subunit | YP_310132 | 3.4.21.— | increase output efficiency |
| umuC | *E. coli* | DNA polymerase V, subunit | ABC42261 | 2.7.7.7 | increase output efficiency |
| pntA, pntB | *Shigella flexneri* | NADH:NADPH transhydrogenase (alpha and beta subunits) | P07001, P0AB70 | 1.6.1.2 | increase output efficiency |

Other

| fabK | *Streptococcus pneumoniae* | trans-2-enoyl-ACP reductase II | AAF98273 | 1.3.1.9 | Contributes to fatty acid biosynthesis |
|---|---|---|---|---|---|
| fabL | *Bacillus licheniformis* DSM 13 | enoyl-(acyl carrier protein) reductase | AAU39821 | 1.3.1.9 | Contributes to fatty acid biosynthesis |

TABLE 1-continued

Enzymatic Activities

| Gene Designation | Source Organism | Enzyme Name | Accession # | EC Number | Exemplary Use |
|---|---|---|---|---|---|
| fabM | Streptococcus mutans | trans-2, cis-3-decenoyl-ACP isomerase | DAA05501 | 4.2.1.17 | Contributes to fatty acid biosynthesis |

TABLE 2

Thioesterase Activity

| Designation/Name | Organism | EC Number |
|---|---|---|
| tesA (with or without leader sequence) | Escherichia coli | 3.1.2.2- or 3.1.2.14 or 3.1.1.5 |
| tesA (without leader sequence) | Escherichia coli | 3.1.2.2- or 3.1.2.14 or 3.1.1.5 |
| tes | Photbacterium profundum | 3.1.2.2 or 3.1.2.14 |
| tesB | Escherichia coli | 3.1.2.2 |
| TE_CAD63310 | Lactobacillus plantarum | 3.1.2.2 or 3.1.2.14 |
| TE_EEI82564 | Anaerococcus tetradius | 3.1.2.2 or 3.1.2.14 |
| fatB1 | Umbellularia californica | 3.1.2.14 |
| fatB2 | Cuphea hookeriana | 3.1.2.14 |
| fatB3 | Cuphea hookeriana | 3.1.2.14 |
| fatB | Cinnamomum camphora | 3.1.2.14 |
| fatB | Arabidopsis thaliana | 3.1.2.14 |
| fatA1 | Helianthus annuus | 3.1.2.14 |
| fatA | Brassica juncea | 3.1.2.14 |
| fatA | Cuphea hookeriana | 3.1.2.14 |
| fadM | Escherichia coli | 3.1.2.2 |
| yciA | Escherichia coli | 3.1.2.2 |
| ybgC | Escherichia coli | 3.1.2.2 |
| phaG | Pseudomonas putida | 3.1.2.2 or 3.1.2.14 |

TABLE 3

Carboxylic Acid Reductase (CAR) Activity

| Designation/Name | Organism | Genpept Accession | EC Number |
|---|---|---|---|
| carB | Mycobacterium smegmatis | YP_889972 | 1.2.99.6 |
| carA | Mycobacterium smegmatis | ABK75684 | 1.2.99.6 |
| FadD9 | Mycobacterium smegmatis | WP_003897160 | 1.2.99.6 |
| car | Mycobacterium genavense | WP_025734970 | 1.2.99.6 |
| car | Nocardia iowensis | Q6RKB1 | 1.2.99.6 |
| car | Nocardia brasiliensis | WP_029899937 | 1.2.99.6 |

TABLE 4

Alcohol Dehydrogenase (ADH) or Aldehyde Reductase (AR) Activity

| Designation/Name | Organism | EC Number |
|---|---|---|
| yqhD | Escherichia coli | 1.1.1.1 or 1.1.1.2 |
| alrA | Acinetobacter sp. ADP1 | 1.1.1.1 or 1.1.1.2 |
| yjgB | Escherichia coli | 1.1.1.1 or 1.1.1.2 |
| yahK | Escherichia coli | 1.1.1.1 or 1.1.1.2 |
| adhP | Escherichia coli | 1.1.1.1 or 1.1.1.2 |
| ydjL | Escherichia coli | 1.1.1.1 or 1.1.1.2 |
| yhdH | Escherichia coli | 1.1.1.1 or 1.1.1.2 |
| yafB (dkgB) | Escherichia coli | 1.1.1.1 or 1.1.1.2 |
| yqhE (dkgA) | Escherichia coli | 1.1.1.1 or 1.1.1.2 |
| ybbo | Escherichia coli | 1.1.1.1 or 1.1.1.2 |
| gldA | Escherichia coli | 1.1.1.1 or 1.1.1.2 |

The disclosure identifies polynucleotides that code for polypeptides with enzymatic activity that are useful in the recombinant host cells and methods of production. The polypeptides with enzymatic activity contribute to the production of compositions including the fatty diol compounds. It will be generally recognized that absolute sequence identity to such polynucleotides is not necessary. For example, changes in a particular polynucleotide sequence (e.g., a polynucleotide encoding a polypeptide with enzymatic function) can be made and the encoded polypeptide screened for activity. Such changes typically comprise conservative mutations and silent mutations (e.g., codon optimization). Genetically engineered or modified polynucleotides and encoded variant polypeptides can be screened for a desired function, including but not limited to, increased catalytic activity, increased stability, or decreased inhibition (e.g., decreased feedback inhibition), using methods known in the art.

In addition, the disclosure identifies enzymatic activities involved in various steps (i.e., reactions) of engineered pathways involved in fatty diol production as described herein (supra) according to Enzyme Classification (EC) number, and provides exemplary polypeptides (e.g., enzymes) categorized by such EC numbers, and exemplary polynucleotides encoding such polypeptides. Such exemplary polypeptides and polynucleotides, which are identified herein by Accession Numbers and/or Sequence Identifier Numbers (SEQ ID NOs), are useful for engineering fatty acid pathways that lead to production of fatty diols including 1,3-fatty diols in parental host cells to obtain the recombinant or genetically modified host cells described herein. The polypeptides and polynucleotides described herein are exemplary and non-limiting. The sequences of homologues of exemplary polypeptides described herein are available to those of skill in the art through various databases (e.g., the Entrez databases provided by the National Center for Biotechnology Information (NCBI), the ExPasy databases provided by the Swiss Institute of Bioinformatics, the BRENDA database provided by the Technical University of Braunschweig, and the KEGG database provided by the Bioinformatics Center of Kyoto University and University of Tokyo, all which are available on the world wide web).

Fermentation and Production of Fatty Diols

As used herein, fermentation broadly refers to the conversion of organic materials into target substances by recombinant host cells. For example, this includes the conversion of a carbon source by recombinant host cells into fatty acid derivatives such as fatty diols by propagating a culture of the recombinant host cells in a media comprising the carbon source. The conditions permissive for the production of the target substances such as fatty diols and/or fatty alcohols are any conditions that allow a host cell to produce a desired product, such as a fatty diol composition. Similarly, this includes any conditions in which the polynucleotide sequence of a vector that is expressed in the host cells allows the host cells to synthesize the target polypeptide. Suitable conditions include, for example, typical fermentation conditions. Fermentation conditions can include many parameters, including but not limited to temperature ranges, pH levels, levels of aeration, feed rates and media composition. Each of these conditions, individually and in combination, allows the host cell to grow. Fermentation can be aerobic, anaerobic, or variations thereof (such as micro-aerobic). Exemplary culture media include broths (liquid) or gels (solid). Generally, the medium includes a carbon source (e.g., a simple carbon source derived from a renewable feedstock) that can be metabolized by a host cell directly. In addition, enzymes can be used in the medium to facilitate the mobilization (e.g., the depolymerization of starch or cellulose to fermentable sugars) and subsequent metabolism of the carbon source.

For small scale production, the engineered host cells can be grown in batches of, for example, about 100 µL, 200 µL, 300 µL, 400 µL, 500 µL, 1 mL, 5 mL, 10 mL, 15 mL, 25 mL, 50 mL, 75 mL, 100 mL, 500 mL, 1 L, 2 L, 5 L, or 10 L; fermented; and induced to express desired polynucleotide sequences, such as a polynucleotides encoding polypeptides having specific enzymatic activity (e.g., TE, CAR, ADH, FAR, ACR, ACC and/or AAR enzymatic activity). For large scale production, the engineered host cells can be grown in cultures having a volume batches of about 10 L, 100 L, 1000 L, 10,000 L, 100,000 L, 1,000,000 L or larger; fermented; and induced to express any desired polynucleotide sequence. The fatty diol compositions described herein can be found in the extracellular environment of the recombinant host cell culture and can be readily isolated from the culture medium. A fatty acid derivative such as a fatty diol and/or a fatty alcohol may be secreted by the recombinant host cell, transported into the extracellular environment or passively transferred into the extracellular environment of the recombinant host cell culture. The fatty diol composition may be isolated from a recombinant host cell culture using routine methods known in the art.

In order to produce fatty diols, a number of modifications were made to production host cells (supra). Thus, the disclosure provides recombinant host cells which have been engineered to provide biosynthesis pathway relative to non-engineered or native host cells (e.g., wild type host cells that function as control cells), which is accomplished, for example, through specific strain improvements. Microorganisms such as bacteria, cyanobacteria, yeast, algae, or filamentous fungi can be used as production hosts. Non-limiting examples of microorganisms that may be used as production hosts include *E. coli, S. cerevisiae*, and others. Microbial strains efficiently convert glucose or other renewable feedstocks into fatty acids derivatives, including fatty alcohols and fatty diols. In order to achieve that, the strains have been carefully engineered to express key enzymes with specific functionalities. Protocols and procedures for high density fermentations for the production of various compounds have been established (see, e.g., U.S. Pat. Nos. 8,372,610; 8,323,924; 8,313,934; 8,283,143; 8,268,599; 8,183,028; 8,110,670; 8,110,093; and 8,097,439) incorporated herein by reference.

Notably, methods to directly and efficiently produce fatty diols, including 1,3-diols from glucose or other renewable feedstocks did not exist until now. Yet, these fatty diols find use a components for detergents, surfactants, emulsifiers, emollients, solvents, plastics, and food additives. The fermentation based method for the production of fatty diols and compositions thereof as presented herein provides an environmentally friendly alternative to chemical methods employed in the art. In some embodiments, the host cell is cultured in a culture medium (e.g., fermentation medium) comprising an initial concentration of a carbon source (e.g., a simple carbon source) of about 20 g/L to about 900 g/L. In other embodiments, the culture medium comprises an initial concentration of a carbon source of about 2 g/L to about 10 g/L; of about 10 g/L to about 20 g/L; of about 20 g/L to about 30 g/L; of about 30 g/L to about 40 g/L; or of about 40 g/L to about 50 g/L. In some embodiments, the level of available carbon source in the culture medium can be monitored during the fermentation proceeding. In some embodiments, the method further includes adding a supplemental carbon source to the culture medium when the level of the initial carbon source in the medium is less than about 0.5 g/L. In some embodiments, a supplemental carbon source is added to the culture medium when the level of the carbon source in the medium is less than about 0.4 g/L, less than about 0.3 g/L, less than about 0.2 g/L, or less than about 0.1 g/L. In some embodiments, the supplemental carbon source is added to maintain a carbon source level of about 1 g/L to about 25 g/L. In some embodiments, the supplemental carbon source is added to maintain a carbon source level of about 2 g/L or more (e.g., about 2 g/L or more, about 3 g/L or more, about 4 g/L or more). In certain embodiments, the supplemental carbon source is added to maintain a carbon source level of about 5 g/L or less (e.g., about 5 g/L or less, about 4 g/L or less, about 3 g/L or less). In some embodiments, the supplemental carbon source is added to maintain a carbon source level of about 2 g/L to about 5 g/L, of about 5 g/L to about 10 g/L, or of about 10 g/L to about 25 g/L.

In one embodiment the carbon source for the fermentation is derived from a renewable feedstock. In some embodiments, the carbon source is glucose. In other embodiments, the carbon source is glycerol. Other possible carbon sources include, but are not limited to, fructose, mannose, galactose, xylose, arabinose, starch, cellulose, pectin, xylan, sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. In one embodiment, the carbon source is derived from corn, sugar cane, sorghum, beet, switch grass, ensilage, straw, lumber, pulp, sewage, garbage, cellulosic urban waste, flu-gas, syn-gas, or carbon dioxide. The simple carbon source can also be a product of photosynthesis, such as glucose or sucrose. In one embodiment, the carbon source is derived from a waste product such as glycerol, flu-gas, or syn-gas; or from the reformation of organic materials such as biomass; or from natural gas or from methane, or from the reformation of these materials to syn-gas; or from carbon dioxide that is fixed photosynthetically, for example 1,3 diols may be produced by recombinant cyanobacteria growing photosynthetically and using CO2 as carbon source. In certain embodiments, the carbon source is derived from biomass. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, municipal solid waste, and food leftovers.

In some embodiments, the fatty diol (e.g., 1,3-diol) is produced at a concentration of about 0.5 g/L to about 40 g/L. In some embodiments, the fatty diol is produced at a concentration of about 1 g/L or more (e.g., about 1 g/L or more, about 10 g/L or more, about 20 g/L or more, about 50 g/L or more, about 100 g/L or more). In some embodiments, the fatty diol is produced at a concentration of about 1 g/L to about 170 g/L, of about 1 g/L to about 10 g/L, of about 40 g/L to about 170 g/L, of about 100 g/L to about 170 g/L, of about 10 g/L to about 100 g/L, of about 1 g/L to about 40 g/L, of about 40 g/L to about 100 g/L, or of about 1 g/L to about 100 g/L.

In some embodiments, the fatty diol is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty diol (e.g., 1,3-diol) is produced at a titer of more than 100 g/L, more than 200 g/L, more than 300 g/L, or higher, such as 500 g/L, 700 g/L, 1000 g/L, 1200 g/L, 1500 g/L, or 2000 g/L. A preferred titer of a fatty diol such as a 1,3-diol produced by a recombinant host cell according to the methods of the disclosure is from 5 g/L to 200 g/L, 10 g/L to 150 g/L, 20 g/L to 120 g/L and 30 g/L to 100 g/L, 100 g/L to 150 g/L, and 120 g/L to 180 g/L. In one embodiment, the titer of a fatty diol such as a 1,3-diol produced by a recombinant host cell according to the methods of the disclosure is about 1 g/L to about 250 g/L and more particularly, 90 g/L to about 120 g/L. The titer may refer to a particular 1,3-diol or a combination of 1,3-diols of different chain length or different functionalities produced by a given recombinant host cell culture.

In other embodiments, the host cells engineered to produce a fatty diol such as a 1,3-diol according to the methods of the disclosure have a yield of at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, or at least 40% or a range bounded by any two of the foregoing values. In other embodiments, a fatty diol such as a 1,3-diol is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of a fatty diol such as a 1,3-diol produced by the recombinant host cell according to the methods of the disclosure can be 5% to 15%, 10% to 25%, 10% to 22%, 15% to 27%, 18% to 22%, 20% to 28%, or 20% to 30%. In a particular embodiment, the yield of a fatty diol such as a 1,3-diol produced by the recombinant host cell is about 10% to about 40%. In another particular embodiment, the yield of a fatty diol such as a 1,3-diol produced by the recombinant host cell is about 25% to about 30%. The yield may refer to a particular fatty diol such as a 1,3-diol or a combination of 1,3-diols produced by a given recombinant host cell culture. In addition, the yield will also be dependent on the feedstock used.

In some embodiments, the productivity of a fatty diol such as a 1,3-diol produced by a recombinant host cell is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, or at least 2500 mg/L/hour. For example, the productivity of a fatty diol such as a 1,3-diol produced by a recombinant host cell according to the methods of the disclosure may be from 500 mg/L/hour to 2500 mg/L/hour, or from 700 mg/L/hour to 2000 mg/L/hour. In one particular embodiment, the productivity is about 0.7 mg/L/h to about 3 g/L/h. The productivity may refer to a particular fatty diol such as a 1,3-diol produced by a given recombinant host cell culture.

In some embodiments, the host cell used in the fermentation procedures discussed herein (supra) is a mammalian cell, plant cell, insect cell, yeast cell, fungus cell, filamentous fungi cell, an algal cell, a cyanobacterial cell, and bacterial cell. In particular embodiments, the host cell is selected from the genus *Escherichia*, *Bacillus*, *Pseudomonas*, *Lactobacillus*, *Rhodococcus*, *Synechococcus*, *Synechoystis*, *Pseudomonas*, *Aspergillus*, *Trichoderma*, *Neurospora*, *Fusarium*, *Humicola*, *Rhizomucor*, *Kluyveromyces*, *Pichia*, *Mucor*, *Myceliophtora*, *Penicillium*, *Phanerochaete*, *Pleurotus*, *Trametes*, *Chrysosporium*, *Saccharomyces*, *Stenotrophamonas*, *Schizosaccharomyces*, *Yarrowia*, or *Streptomyces*. In other embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In other embodiments, the host cell is a *Pseudomonas putida* cell. In certain embodiments, the host cell is a *Synechococcus* sp. PCC7002, *Synechococcus elongatus* PCC 7942, *Synechoystis* sp. PCC 6803, *Synechococcus elongatus* PCC6301, *Prochlorococcus marinus* CCMP1986 (MED4), *Anabaena variabilis* ATCC29413, *Nostoc punctiforme* ATCC29133 (PCC73102), *Gloeobacter violaceus* ATCC29082 (PCC7421), *Nostoc* sp. ATCC27893 (PCC7120), *Cyanothece* sp. PCC7425 (29141), *Cyanothece* sp. ATCC51442, or *Synechococcus* sp. ATCC27264 (PCC7002). In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a

*Mucor michei* cell. In other embodiments, the host cell is an *Actinomycetes* cell. In yet other embodiments, the host cell is a *Streptomyces lividans* cell or a *Streptomyces murinus* cell. In other embodiments, the host cell is a *Saccharomyces cerevisiae* cell.

In yet other embodiments, the host cell is a cell from an eukaryotic plant, algae, cyanobacterium, green-sulfur bacterium, green non-sulfur bacterium, purple sulfur bacterium, purple non-sulfur bacterium, extremophile, yeast, fungus, engineered organisms thereof, or a synthetic organism. In certain embodiments, the host cell is a cell from *Arabidopsis thaliana, Panicum virgatums, Miscanthus giganteus, Zea mays, botryococcuse braunii, Chalamydomonas reinhardtii, Dunaliela salina, Thermosynechococcus elongatus, Synechococcus elongatus, Synechococcus sp., Synechocystis sp., Chlorobium tepidum, Chloroflexus auranticus, Chromatiumm vinosum, Rhodospirillum rubrum, Rhodobacter capsulatus, Rhodopseudomonas palusris, Clostridium ljungdahlii, Clostridiuthermocellum,* or *Pencillium chrysogenum*. In certain other embodiments, the host cell is from *Pichia pastories, Saccharomyces cerevisiae, Yarrowia lipolytica, Schizosaccharomyces pombe, Pseudomonas fluorescens, Pseudomonas putida* or *Zymomonas mobilis*. In yet further embodiments, the host cell is a cell from *Synechococcus* sp. PCC 7002, *Synechococcus* sp. PCC 7942, or *Synechocystis* sp. PCC6803. In some embodiments, the host cell is a CHO cell, a COS cell, a VERO cell, a BHK cell, a HeLa cell, a Cv1 cell, an MDCK cell, a 293 cell, a 3T3 cell, or a PC12 cell. In particular embodiments, the host cell is an *E. coli* cell. In some embodiments, the *E. coli* cell is a strain B, a strain C, a strain K, or a strain W *E. coli* cell.

Compositions and Formulations of Fatty Diols

Bioproducts (e.g., the fatty diol compositions produced in accordance with the present disclosure) including biologically produced organic compounds, and in particular, the fatty diol compositions produced using the fatty acid biosynthetic pathway disclosed herein, are produced from renewable sources (e.g., from a simple carbon source derived from renewable feedstocks) and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588). The ability to distinguish the bioproducts such as the presently disclosed fatty diols from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the bioproducts produced herein can be followed or tracked in commerce on the basis of their unique carbon isotope profile. Bioproducts can be distinguished from petroleum based organic compounds by comparing the stable carbon isotope ratio ($^{13}C/^{12}C$) in each sample. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in $^{13}C/^{12}C$ and the corresponding $\delta^{13}C$ values. Both C4 and C3 plants exhibit a range of $^{13}C/^{12}C$ isotopic ratios, but typical values are about −7 to about −13 per mil for C4 plants and about −19 to about −27 per mil for C3 plants (see, e.g., Stuiver et al., Radiocarbon 19:355 (1977)). Non-renewables such as coal and petroleum fall generally in this latter range.

$$\delta^{13}C(‰)=[(^{13}C/^{12}C)\text{sample}-(^{13}C/^{12}C)\text{standard}]/(^{13}C/^{12}C)\text{standard}\times 1000$$

A series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46. The compositions described herein include fatty diol compositions and products produced by any of the methods described herein. Specifically, fatty diol composition or product can have a $\delta^{13}C$ of about −28 or greater, about −27 or greater, −20 or greater, −18 or greater, −15 or greater, −13 or greater, −10 or greater, or −8 or greater. For example, the fatty diol composition or product can have a $\delta^{13}C$ of about −30 to about −15, about −27 to about −19, about −25 to about −21, about −15 to about −5, about −13 to about −7, or about −13 to about −10. In other instances, the fatty diol composition or product t can have a $\delta^{13}C$ of about −10, −11, −12, or −12.3. Fatty diol compositions and products produced in accordance with the disclosure herein can also be distinguished from petroleum based organic compounds by comparing the amount of $^{14}C$ in each compound. Because $^{14}C$ has a nuclear half-life of 5730 years, petroleum based fuels containing "older" carbon can be distinguished from fatty diol compositions and bioproducts which contain "newer" carbon (see, e.g., Currie, "Source Apportionment of Atmospheric Particles", Characterization of Environmental Particles, J. Buffle and H. P. van Leeuwen, Eds., 1 of Vol. I of the *IUPAC Environmental Analytical Chemistry Series* (Lewis Publishers, Inc.) 3-74, (1992)).

The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about 1.2×10-12, with an approximate relaxation "half-life" of 7-10 years. This latter half-life must not be taken literally; rather, one must use the detailed atmospheric nuclear input/decay function to trace the variation of atmospheric and biospheric $^{14}C$ since the onset of the nuclear age. It is this latter biospheric $^{14}C$ time characteristic that holds out the promise of annual dating of recent biospheric carbon. $^{14}C$ can be measured by accelerator mass spectrometry (AMS), with results given in units of fraction of modern carbon (fM). In that respect, the fM has the same meaning as defined by National Institute of Standards and Technology (NIST) Standard Reference Materials (SRMs 4990B and 4990C), known as oxalic acids standards HOxI and HOxII. The fundamental definition relates to 0.95 times the 14C/12C isotope ratio HOxI (referenced to AD 1950). This is roughly equivalent to decay-corrected pre-Industrial Revolution wood. For the current living biosphere (plant material), the fM is approximately 1.1. The fatty diol compositions and products described herein include bioproducts that can have an fM $^{14}C$ of at least about 1. For example, the bioproduct of the disclosure can have an fM $^{14}C$ of at least about 1.01, an fM $^{14}$C of about 1 to about 1.5, an fM $^{14}$C of about 1.04 to about 1.18, or an fM $^{14}$C of about 1.111 to about 1.124.

Another measurement of $^{14}$C is known as the percent of modern carbon (pMC). For an archaeologist or geologist using $^{14}$C dates, AD 1950 equals zero years old. This also represents 100 pMC. Bomb carbon in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}$C signature near 107.5 pMC. Petroleum based compounds will have a pMC value of zero. Combining fossil carbon with present day carbon will result in a dilution of the present day pMC content. By presuming 107.5 pMC represents the $^{14}$C content of present day biomass materials and 0 pMC represents the $^{14}$C content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning 100% equal to 107.5 pMC and 0% equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty diols as described herein can have a pMC of at least about 50, 60, 70, 75, 80, 85, 90, 95, 96, 97, 98, 99, or 100. In other instances, a fatty diol composition described herein can have a pMC of between about 50 and about 100; about 60 and about 100; about 70 and about 100; about 80 and about 100; about 85 and about 100; about 87 and about 98; or about 90 and about 95. In yet other instances, a fatty diol composition described herein can have a pMC of about 90, 91, 92, 93, 94, or 94.2.

Fatty diols such as a 1,3-diols are molecules that are valuable and desirable in many industrial applications. The present disclosure produces such compounds through recombinant microorganisms, including in vivo and thereby generates a range of useful products. Such products include 1,3-diols and compositions thereof. Examples of the 1,3-diols include, but are not limited to, $C_5$ 1,3 diols (1,3-pentanediol); $C_6$ 1,3 diols (1,3-hexanediol); $C_7$ 1,3 diols (1,3-heptanediol); $C_8$ 1,3 diols (1,3-octanediol); $C_9$ 1,3 diols (1,3-nonanediol); $C_{10}$ 1,3 diols (1,3-decanediol); $C_{11}$ 1,3 diols (1,3-undecanediol); $C_{12}$ 1,3 diols (1,3-dodecanediol); $C_{13}$ 1,3 diols (1,3-tridecanediol); $C_{14}$ 1,3 diols (1,3-tetradecanediol); $C_{15}$ 1,3 diols (1,3-pentadecanediol); $C_{16}$ 1,3 diols (1,3-hexadecanediol); $C_{17}$ 1,3 diols (1,3-heptadecanediol); $C_{18}$ 1,3 diols (1,3-octadecanediol); $C_{19}$ 1,3 diols (1,3-nonadecanediol); and the like. While mostly even chain 1,3-diols are described herein, odd chain 1,3-diols are also included, such as those having 7-21 carbons, and more preferably 5-19 carbons.

The 1,3-diols of the present disclosure have various chain lengths and/or saturation and/or branching characteristics. In some embodiments, the 1,3-diol composition includes mostly one type of 1,3-diol such as, for example, a $C_5$ 1,3 diol (1,3-pentanediol); a $C_6$ 1,3 diol (1,3-hexanediol); a $C_7$ 1,3 diol (1,3-heptanediol); a $C_8$ 1,3 diol (1,3-octanediol); a $C_9$ 1,3 diol (1,3-nonanediol); a $C_{10}$ 1,3 diol (1,3-decanediol); a $C_{11}$ 1,3 diol (1,3-undecanediol); a $C_{12}$ 1,3 diol (1,3-dodecanediol); a $C_{13}$ 1,3 diol (1,3-tridecanediol); a $C_{14}$ 1,3 diol (1,3-tetradecanediol); a $C_{15}$ 1,3 diol (1,3-pentadecanediol); a $C_{16}$ 1,3 diol (1,3-hexadecanediol); a $C_{17}$ 1,3 diol (1,3-heptadecanediol); a $C_{18}$ 1,3 diol (1,3-octadecanediol); a $C_{19}$ 1,3 diols (1,3-nonadecanediol); or the like. In another embodiment, the 1,3-diol composition includes mostly mixtures of specific 1,3-diols of a specific chain length in particular ratios. In yet another embodiment, the 1,3-diol composition includes combinations of one or more 1,3-diols of a specific chain length in combination with other ingredients or components in order to produce detergents, surfactants, emulsifiers, emollients, solvents, plastics, and food additives.

In one embodiment, the fatty diol composition includes $C_{12}$ 1,3-diols in a mixture of straight chain fatty alcohols. In another embodiment, the fatty diol composition includes $C_{12}$ 1,3-diols in a mixture of branched chain fatty alcohols. In another embodiment, the fatty diol composition includes $C_{12}$ 1,3-diols in a mixture of straight- and branched chain fatty alcohols. In another embodiment, the fatty diol composition includes $C_{12}$ 1,3-diols in combination with additional ingredients such as, for example, detergent or surfactant ingredients. In yet another embodiment, the fatty diol composition includes $C_{12}$ 1,3-diols in combination with additional ingredients such as, for example, emulsifier or solvent ingredients. In still another embodiment, the fatty diol composition includes $C_{12}$ 1,3-diols in combination with polymers. Herein, the fatty diol composition can be used as a component for plastics. In another embodiment, the fatty diol composition includes $C_{12}$ 1,3-diols in a mixture of food ingredients. In another embodiment, the fatty diol composition includes a 1,3-diol as an intermediate in the synthesis of a surfactant or detergent, such as a glucoside or ethoxide, or in combination with a fragrance, or a chemical building block from which other chemicals can be synthesized.

In another embodiment, the fatty diol composition includes $C_8$-, $C_{10}$-, and $C_{12}$ 1,3-diols in certain ratios in a mixture of straight chain fatty alcohols. In another embodiment, the fatty diol composition includes $C_8$-, $C_{10}$-, and $C_{12}$ 1,3-diols in certain ratios in a mixture of branched chain fatty alcohols. In another embodiment, the fatty diol composition includes $C_8$-, $C_{10}$-, and $C_{12}$ 1,3-diols in certain ratios in a mixture of straight- and branched chain fatty alcohols. In another embodiment, the fatty diol composition includes $C_8$-, $C_{10}$-, and $C_{12}$ 1,3-diols in certain ratios in combination with additional ingredients such as, for example, detergent or surfactant ingredients. In yet another embodiment, the fatty diol composition includes $C_8$-, $C_{10}$-, and $C_{12}$ 1,3-diols in certain ratios in combination with additional ingredients such as, for example, emulsifier or solvent ingredients. In still another embodiment, the fatty diol composition includes $C_8$-, $C_{10}$-, and $C_{12}$ 1,3-diols in certain ratios in combination with polymers. Herein, the fatty diol composition can be used as a component for plastics. In another embodiment, the fatty diol composition includes $C_8$-, $C_{10}$-, and $C_{12}$ 1,3-diols in certain ratios in a mixture of food ingredients.

The disclosure further encompasses a fatty diol composition that includes $C_5$-, $C_6$-, $C_7$-, $C_8$-, $C_9$-, $C_{10}$-, and/or $C_{11}$ 1,3-diols alone or in certain ratios in a mixture of food-related ingredients. Such fatty diols would be useful as food stabilizers, food enhancers, food additives, or food replacements. The compounds and compositions of the fatty diols of the present disclosure can be formulated such that desirable products can be made including detergents, surfactants, emulsifiers, emollients, solvents, plastics, food additives, and more. In one embodiment, $C_{10}$-$C_{18}$ 1,3-diols are contemplated for use as surfactants. In another embodiment, 1,3 diols are used directly or as intermediates in the synthesis of nutraceuticals, pharmaceuticals, agricultural chemicals, and other bioactive molecules.

Discussion around chiral 1,3 diols.

EXAMPLES

The following examples further illustrate the disclosure but should not be construed as in any way limiting its scope.

Example 1: Cultivating Recombinant E. coli Strains for the Production of 1,3-Diols All experiments started from single colonies or freezer stocks of a particular microbial strain. High-throughput (HTP) protocols in 96-well plates were carried out as follows in quadruplicate for each strain: 40 μL Luria-Bertani (LB) culture (from an LB culture growing in a 96 well plate) was used to inoculate 3600 μL LB media, which was then incubated for 3-4 hours at 32° C. shaking. 400 μL of the LB seed was used to inoculate 360 μL Nlim media (see below). After growing at 32° C. for 2 hours at 30-35° C., the cultures were induced with IPTG (final concentration 1 mM). The cultures were then incubated at 30-35° C. with shaking for 20 hours if not noted otherwise, after which they were extracted following the standard extraction protocol detailed below. Shake flask protocols were carried out similarly except that the culture volumes were scaled up such that the final production media volume was 15 ml instead of 400 μl. The shake flask media also contained 0.25% (v/v) Triton X100. Depending on the microbial strains, the appropriate antibiotics were added to the media at all stages.

| Nlim Media Formulation | | |
|---|---|---|
| 1 | x | 5x Salt Soln. with NH4Cl |
| 1 | x | 1000x Trace Vitamins |
| 1 | mg/L | 10 mg/mL Thiamine |
| 1 | mM | 1M MgSO4 |
| 0.1 | mM | 1M CaCl2 |
| 40 | g/L | 500 g/L glucose |
| 1 | x | 1000x Trace minerals |
| 10 | mg/L | 10 g/L Fe Citrate |
| 100 | μg/mL | 100 mg/ml spectinomycin |
| 100 | mM | 2M BisTris (pH 7.0) |

The baseline process in bioreactors was as follows: A cell bank vial of the strain was cultivated in a LB shake flask containing antibiotic(s) at 32° C. until the OD reading of the culture >1. A 5% v/v transfer of this culture was made into minimal seed media (containing ammonium chloride, sodium chloride, potassium phosphate monobasic, magnesium sulfate, calcium chloride, glucose, a trace elements solution, ferric citrate tribasic monohydrate, buffer, and antibiotic(s)), and cultivated overnight at 32° C. This seed culture was then used to inoculate a prepared bioreactor for production.

The initial bioreactor media for this process contained various concentrations of the same components as the seed media, as well as a trace vitamins solution, and optionally small amounts of a complex media component, such as casamino acids, corn steep powder, or yeast extract. Post-sterile additions to the bioreactor optionally included heat labile vitamins or amino acids, glucose, and antibiotic(s).

Prior to inoculation, the bioreactor parameters were stabilized and controllers turned on—dissolved oxygen setpoint: 10-50%; temperature setpoint: 27-37° C.; aeration setpoint: 0.25-1 vvm; pH setpoint: 6.5-7.5. The bioreactor was inoculated with 5% v/v of a seed culture and induced with 1 mM IPTG when the density of the culture reached a desired setpoint.

A feed solution composed of glucose, sucrose, fructose, xylose, or glycerol with other possible media components incorporated in the bioreactor basal media was fed to the culture at a maximal rate of 1-50 g/L/hr glucose (based on the nominal culture volume), using a DO or pH trigger to indicate to the controller when the media was exhausted of its carbon source and the next shot of feed solution should be added. The bioreactor was harvested between 48 and 96 hours of cultivation.

Example 2: Analysis of 1,3-Diols

Fermentation Broth Samples Produced by Recombinant E. coli Strains were Extracted with the Procedure Below:
1. Vortex the broth at 3000 rpm for 30 second before weight
2. Sample 500 μL of broth immediately following vortexing on Vortex Genie
3. Add 5 mL of butyl acetate with 500 mg/L (1-undecanol) as the internal standard
4. Extract broth in a vortexer (DVX-2500 multi-tube vortexer, VWR) at 2500 rpm for 20 minutes
5. Centrifuge the extract (at 4750 rpm) for 10 min at room temperature
6. Pipette 100 μL of the top layer supernatant into GC vials with inserts
7. Derivatize by adding 100 μL of (BSTFA+1% TMCS) to GC vial at room temperature
8. Mix extract and BSTFA reagent for 30 second before injecting on GC/MS as described below:

Instrument Condition for Identification
Initial temperature: 60° C.
Initial time: 5 minutes
Equilibration time: 1 minute
Program rate: 25° C./minute
Final temperature: 300° C.
Final time: 1.6 minute
Detector: MSD
Inlet temperature: 300° C.
Transfer line temperature: 300° C.
MS source: 230° C.
MS Quad: 150° C.
Split ratio: 20:1
Column flow: 1 mL/minute
Sample size: 1 μL

Example 3: Production of 1,3-Diols Using a Pathway with TE from Anaerococcus Tetradius or Lactobacillus plantarum and carB This example shows the unexpected production of 1,3-diols in recombinant E. coli using a metabolic pathway including a microbial thioesterase from Anaerococcus tetradius (TE_EEI82564, genbank accession number WP_004837416) or Lactobacillus plantarum (TE_CAD63310, genbank accession number WP_003640969) and variants of carboxylic acid reductase, CarB, from Mycobacterium smegmatis (genbank accession number YP_889972).

The genes coding for carB2 (SEQ ID NO: 6) and TE_EEI82564 were cloned into a pCL1920-derivative vector (SC101 replicon, spectinomycin resistance marker), such that their transcription was controlled by the IPTG-inducible Ptrc promoter and they formed an operon with genes coding for an alcohol dehydrogenase, alrA, which is not required for fatty alcohol or fatty diol production, but does improve the rate of their production, and variants of 3-keto-acyl-ACP synthase (fabB) and a transcriptional regulator (fadR). The plasmid was named pVA369 (see Table 5). The gene for TE_CAD63310 from *L. plantarum* was cloned in an identical way together with the gene for carB12 (SEQ ID NO: 4), the resulting plasmid was named pJP2 (see Table 5, infra).

Base strains used for plasmid transformation were V668 and DJ81. Briefly, the genome of the base strains were manipulated as follows: In V668, the fadE (acyl-CoA dehydrogenase) gene was deleted, and a synthetic fatty acid biosynthesis operon and a phosphopantetheinyl transferase (entD) were overexpressed. Briefly, the genome of base strain DJ81 was manipulated as follows: the acyl-CoA dehydrogenase (fadE) gene was deleted, and a synthetic fatty acid biosynthesis operon, a phosphopantetheinyl transferase (entD) and a variant thioesterase (tesA) were overexpressed.

Plasmid pVA369 and pJP2 were transformed into base strains D848 and V668, respectively, resulting in strains VA370 and JP-11 (see Table 6, infra). The strains were then cultivated and analyzed for their ability to produce fatty alcohols as described in Examples 1 and 2. Surprisingly, both strains produced several unknown peaks.

Figure 4:
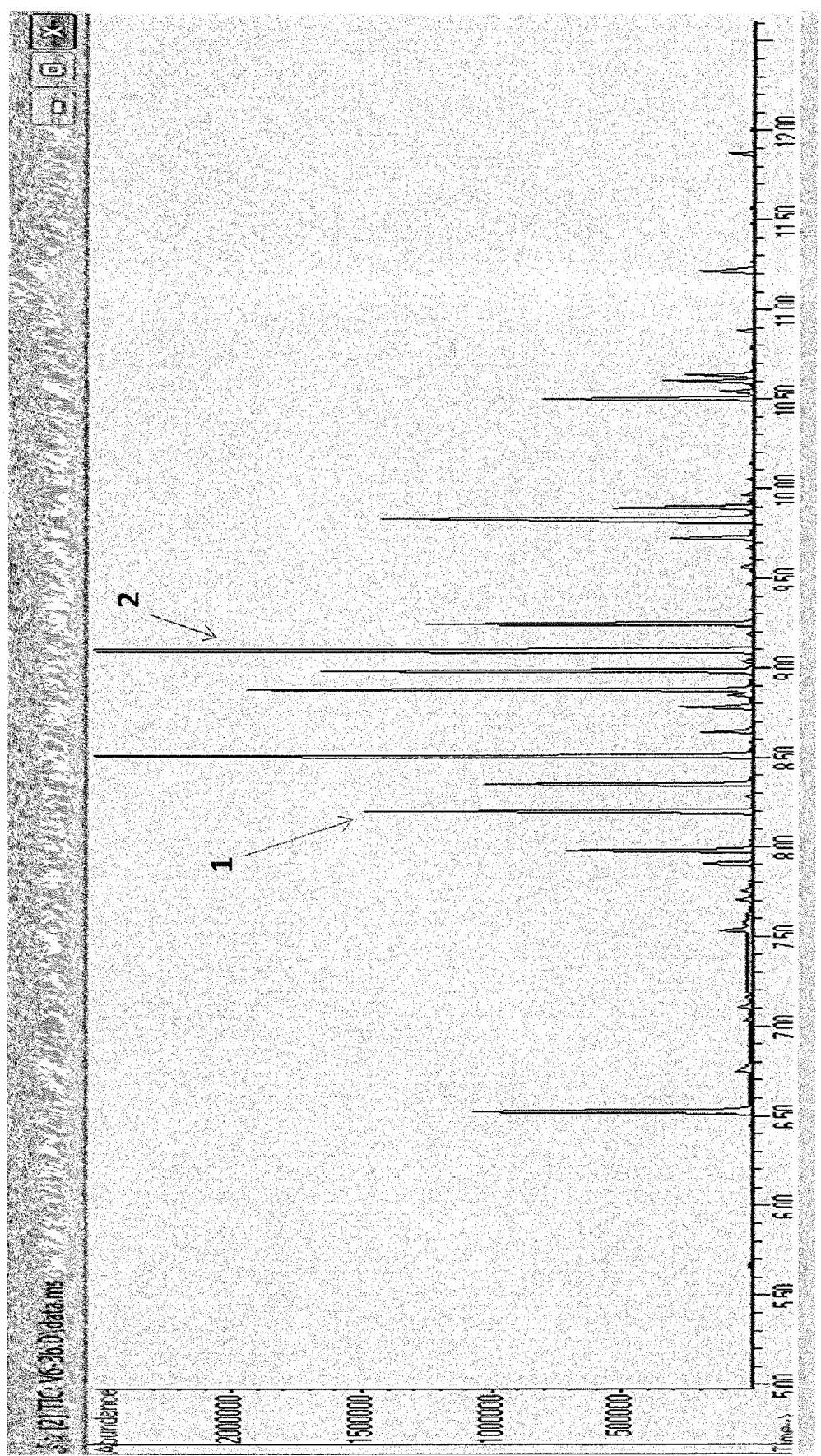
FIG. 4 shows a GC/MS chromatogram of an extract from a recombinant *E. coli* strain expressing TE_EEI82564 and CarB. All samples were derivatized with BSTFA+1% TMCS. Peak (1) is derivatized 1,3-octanol and peak (2) is derivatized 1,3-decanol.
Figure 5:
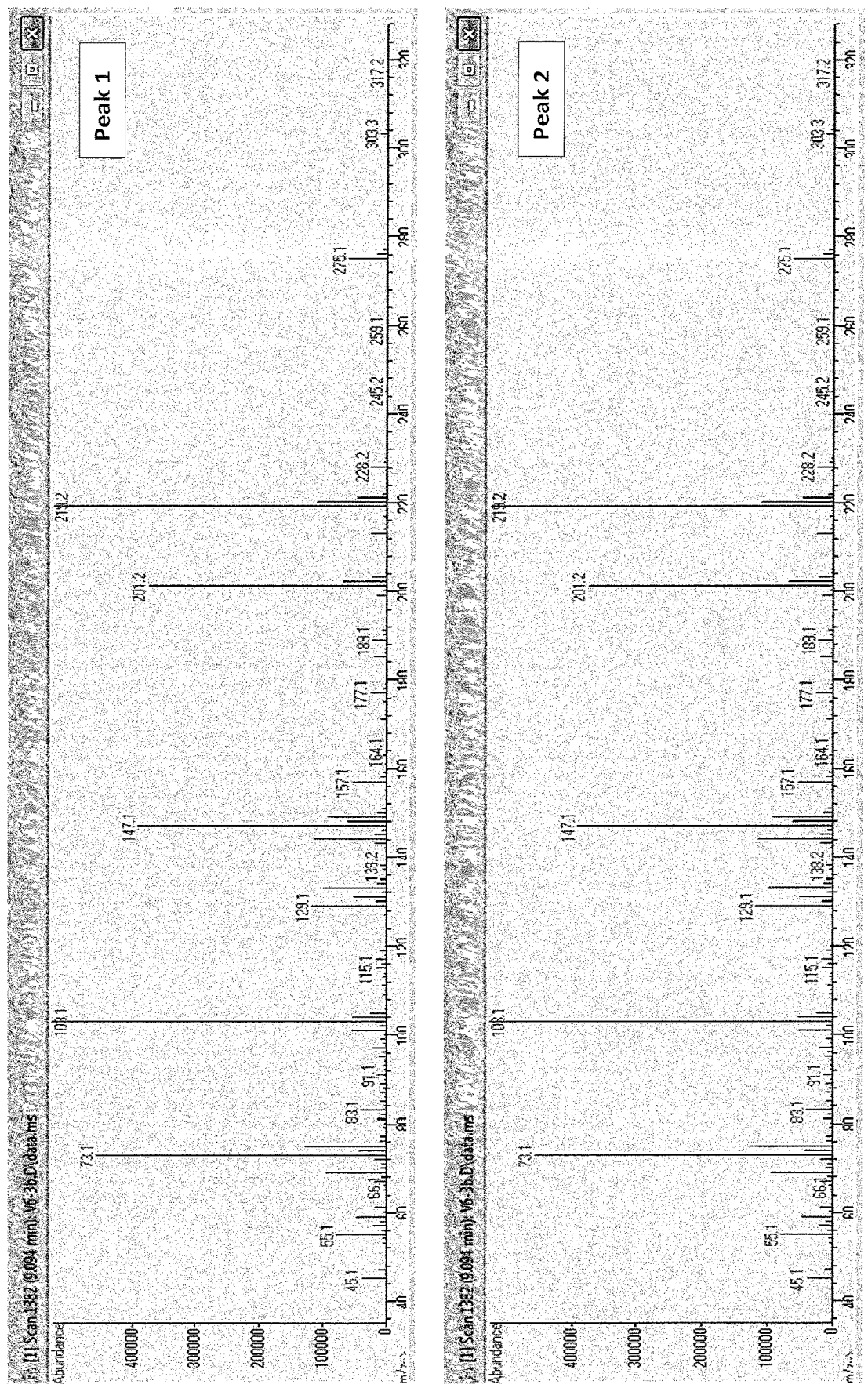
FIG. 5 shows the mass spectra of derivatized peak 1 and peak 2 from FIG. 4, which are derived from a recombinant *E. coli* strains expressing TE_EEI82564 and CarB. Derivatizing agent was BSTFA+1% TMCS.
Figure 6:
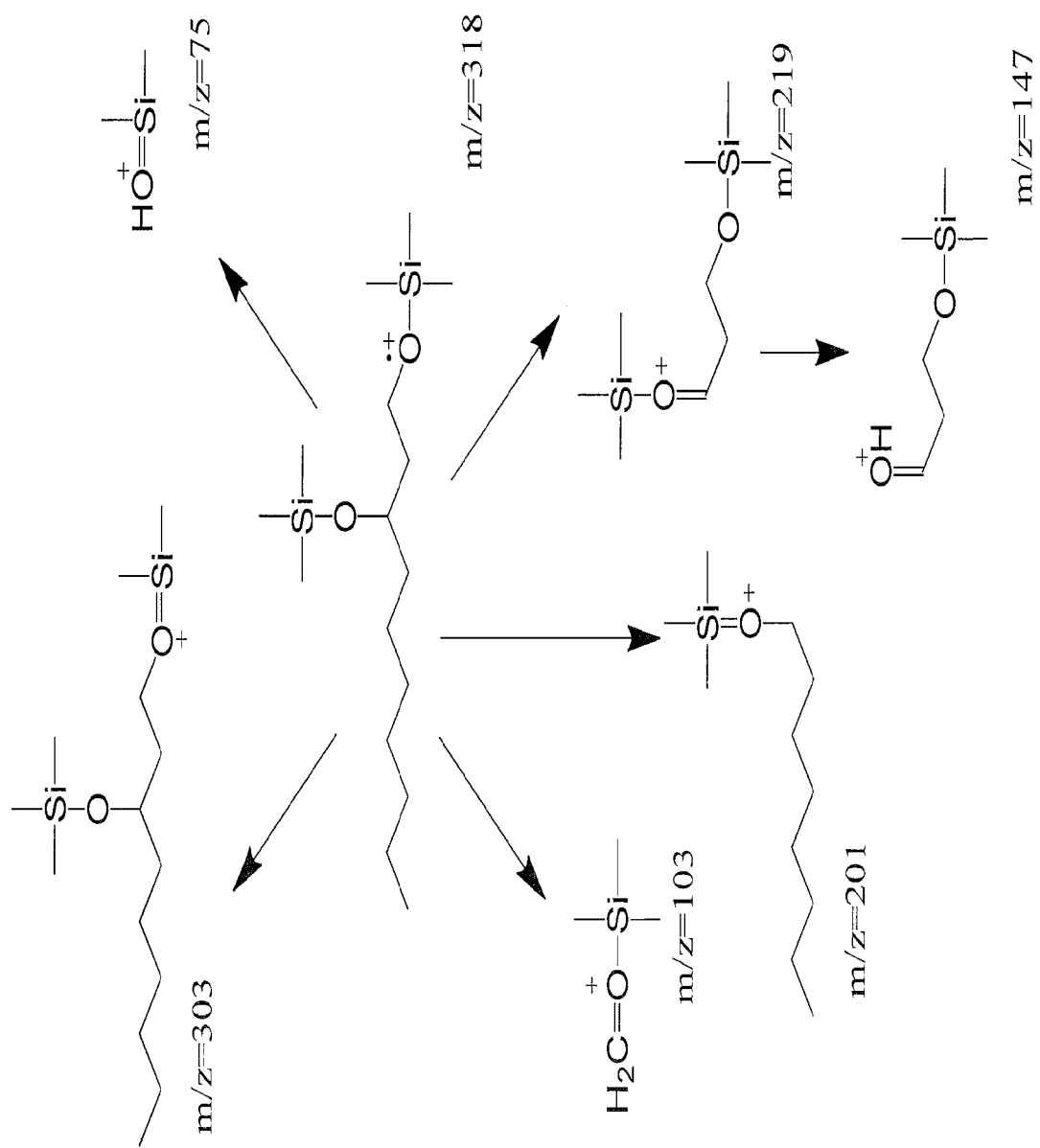
FIG. 6 illustrates the ion fragmentation pattern of 1,3-decanediol derivatized with BSTFA+1% TMCS.

FIG. 4 shows a GC-MS Chromatograph of an extract of strain VA370 expressing TE_EEI82564. Two peaks at RT=8.199 min and RT=9.094 min in the GC-MS chromatograph did not match the retention time of expected fatty alcohols and fatty acids, such as dodecanol and tetradeanol, or dodecanoic acid and tetradecanoic acid. Peak 1 eluted before dodecanol and peak 2 eluted after tetradecanol and before tetradecanoic acid. The ion fragmentation patterns of peaks 1 and 2 (see FIG. 5) suggested that these two peaks were 1,3-trimethylsiloxy octane and 1,3 trimethylsiloxy decane, which are the derivatization products of BSTFA (see Example 2) with 1,3-octanediol and 1,3-decanediol, respectively. For illustration, FIG. 6 shows a schematic of the ion fragments of 1,3 trimethylsiloxy decane as observed in peak 1 in FIG. 5. Trace amount of derivatized 1,3-dodecanediol and 1,3-tetradecanediol were also observed.

Figure 7:
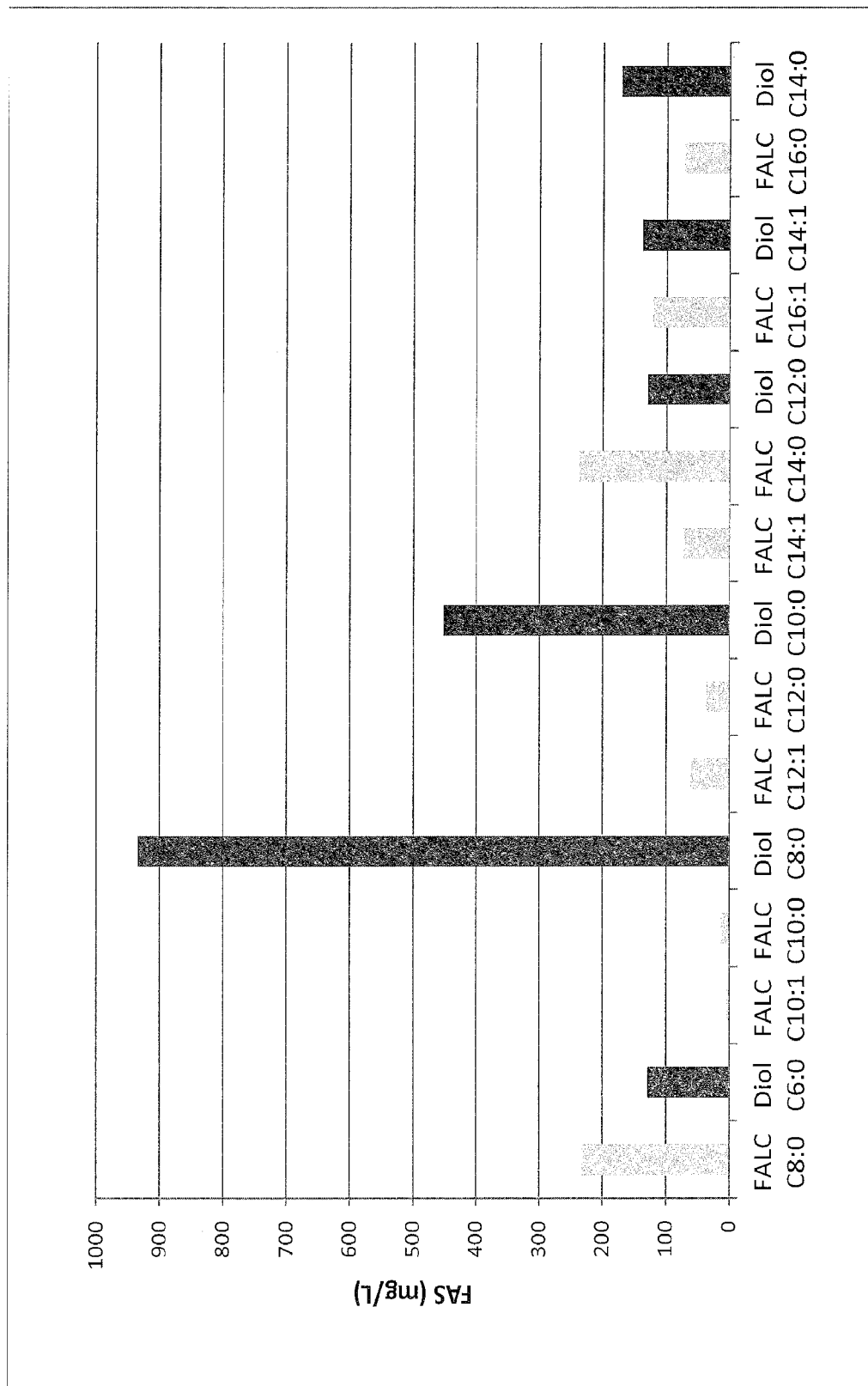
FIG. 7 shows the composition of 1,3-diols (Diol) and fatty alcohols (FALC) produced by a recombinant *E. coli* strain expressing TE_CAD63310 and CarB.
Figure 8:
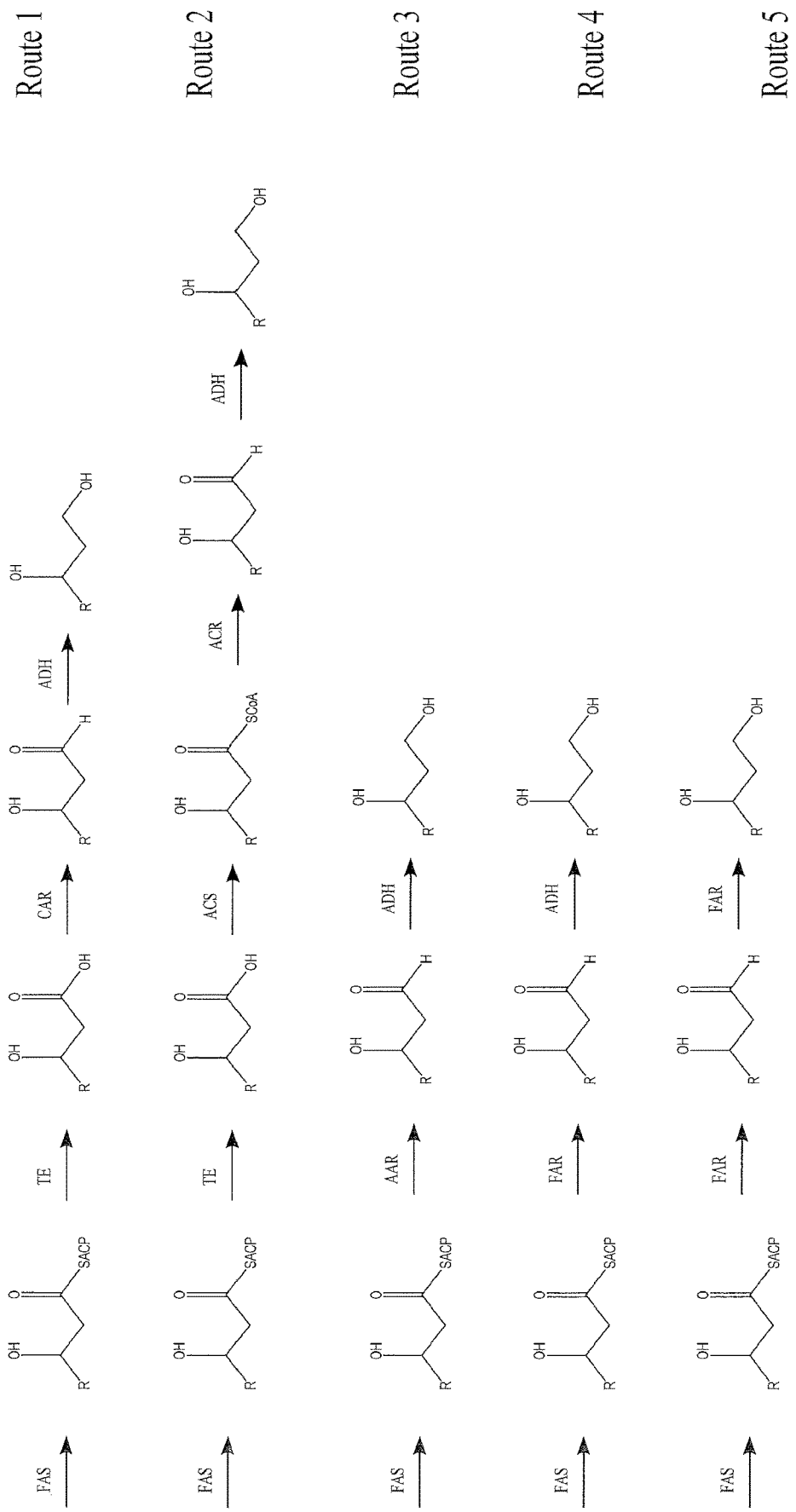
FIG. 8 depicts biochemical pathways that lead to 1,3 fatty diols from acyl-ACP. Route 1 uses enzymatic functionalities such as TE, CAR and ADH to produce 1,3-diols. Route 2 uses TE, ACS, ACR and ADH to produce 1,3-diols. Route 3 uses AAR and ADH to to produce 1,3-diols. Route 4 uses FAR and ADH to produce 1,3-diols. Route 5 uses FAR to produce 1,3-diols.
Figure 9:
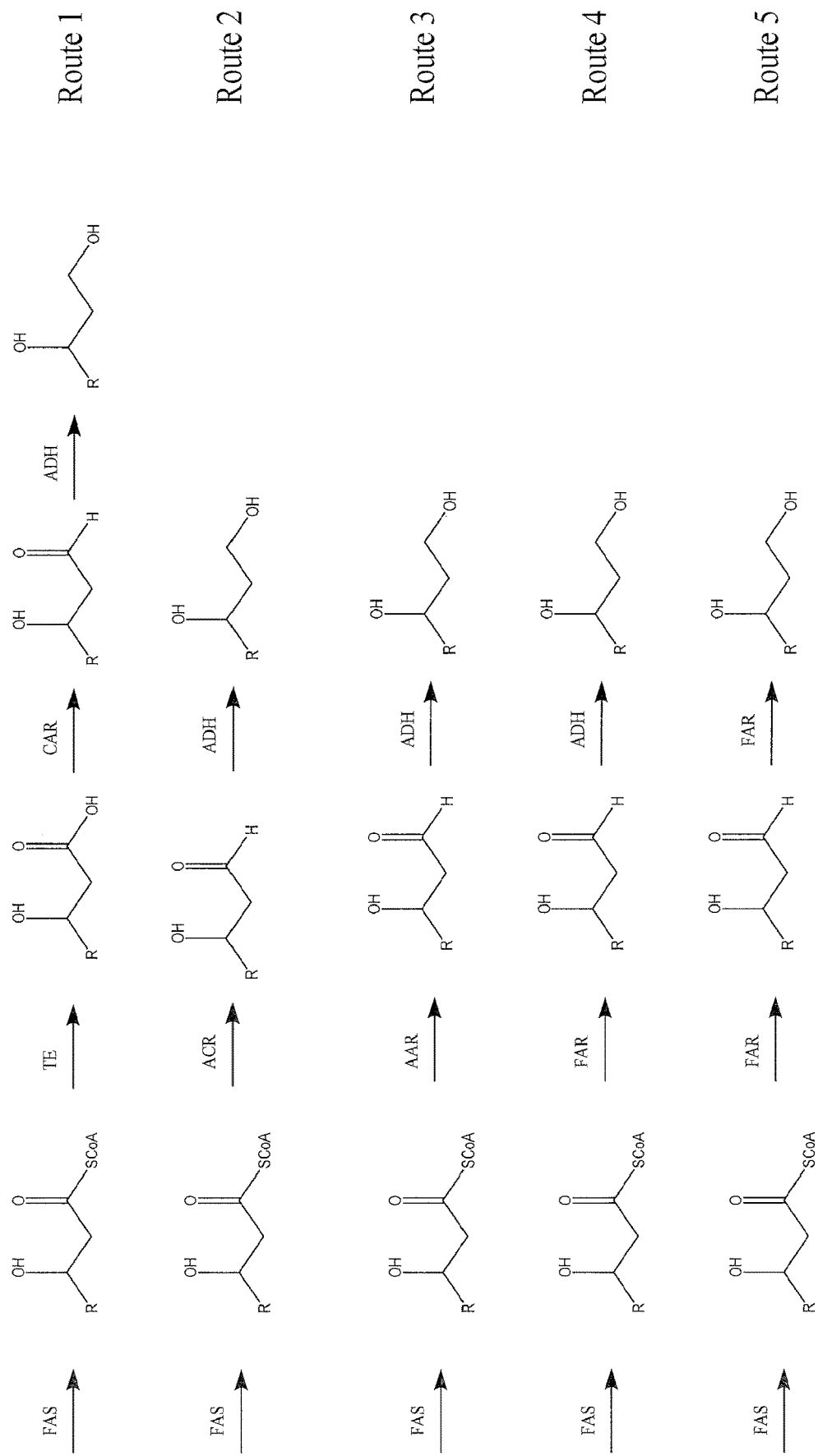
FIG. 9 depicts biochemical pathways that lead to 1,3 fatty diols from acyl-CoA. Route 1 uses enzymatic functionalities such as TE, CAR and ADH to produce 1,3-diols. Route 2 uses ACR and ADH to produce 1,3-diols. Route 3 uses AAR and ADH to to produce 1,3-diols. Route 4 uses FAR and ADH to produce 1,3-diols. Route 5 uses FAR to produce 1,3-diols.

Similarly, extracts of strain JP-11 expressing TE_CAD63310 contained new peaks that were identified as 1,3-octanediol, 1,3-decanediol, 1,3-tetradecanol and 1,3-tetradecenol based on their ion fragmentation pattern and retention time as described above. JP-11 produced a total of 1.9±0.05 g/L 1,3-diols in a HTP fermentation protocol as well as fatty alcohols such as octanol, decanol, dodecanol, dodecenol, tetradecanol and tetradecenol. The product distribution of strain JP-11 is shown in FIG. 7.

The production of 1,3-diols was surprising for two reasons: (i) it requires 3-OH fatty acids as intermediates, which in turn are most likely derived from 3-OH acyl-ACPs by the action of a thioesterase (see FIG. 2). Both thioesterases used in this example have been previously expressed in *E. coli* and were reported only to give rise to fatty acids (Jing et al. BMC Biochemistry 2011, 12:44) suggesting that they are unsuitable for the production of 3-OH fatty acids and therefore 1,3-diols, (ii) it requires 3-OH fatty acid intermediates to be reduced to 3-OH fatty aldehydes by carboxy acid reductase CarB, which are then further reduced to 1,3-diols by alcohol dehydrogenase (ADH). Whereas ADHs are known to be rather promiscuous, CarB had previously not been shown to convert 3-OH fatty acids to 3-OH fatty aldehydes. Thus, the applicants have discovered that certain microbial thioesterases, e.g., TE_EEI82564 and TE_CAD63310, when coexpressed with CarB in *E. coli* host cells, overproduce 1,3-diols. Analysis of the 1,3, diols may show they are highly enriched in (R) enantiomer demonstrating the enantioselectivity of the 3-ketoacyl ACP reductase (FabG) of the native *E. coli* fatty acid biosynthetic machinery.

TABLE 5

Plasmids used for 1,3-diol production

| Plasmid Name | Pathway Genes |
|---|---|
| pVA369 | pCL-carB2-TE_EEI82564alrA-fabB-fadR |
| pJP2 | pCL-carB12-TE_CAD63310-alrA-fabB-fadR |
| pNH328 | pCL-trc-carB8-phaG-alrA |
| pHN330 | pCL-trc-carB8-fatB1-alrA |
| pNT16 | pCL-trc-AAR-alrA |

TABLE 6

Strains used for 1,3-diol production

| Strain Name | Description |
|---|---|
| VA370 | V668 with plasmid pVA369 |
| JP-11 | DJ81 with plasmid pJP2 |
| stNH1371 | D178 with plasmid pNH330 |
| stNH1369 | D178 with plasmid pNH328 |
| Becos247 | DV2 with plasmid pNT16 |

Example 4A: Production of 1,3-Diols Using a Pathway with fatB1 from *Umbellularia californica* and carB This example shows the production of 1,3-diols in recombinant *E. coli* using a metabolic pathway including a plant thioesterase, fatB1, from *Umbellularia california*, (genbank accession number Q41635) and a variant carboxylic acid reductase, CarB, from *Mycobacterium smegmatis*.

The genes coding for carB8 (SEQ ID NO: 8) and fatB1 were cloned into a pCL1920-derivative vector (SC101 replicon, spectinomycin resistance marker), such that their transcription was controlled by the IPTG-inducible Ptrc promoter and they formed an operon with a gene coding for an alcohol dehydrogenase, alrA. The plasmid was named pNH330 (see Table 5).

Base strain used for plasmid transformation was strain D178. Briefly, the genome of strain D178 was modified as follow: the fadE (acyl-CoA dehydrogenase) gene was deleted and a phosphopantetheinyl transferase (entD) was overexpressed. Plasmid pNH330 was transformed into D178 resulting in strain stNH1371 (see Table 6). The strain was then cultivated and analyzed for its ability to produce fatty alcohols and 1,3-diols as described in Examples 1 and 2. The 1,3-diol peaks were identified as described in Example 2.

Strain stNH1371 produced 39.5±3.2 mg/L 1,3-diols in a HTP fermentation protocol. 1,3-dodecanediol was one of the 1,3-diols produced. Besides 1,3-diols fatty alcohols such as dodecanol were also detected. Analysis of the 1,3, diols may show they are highly enriched in (R) enantiomer demonstrating the enantioselectivity of the 3-ketoacyl ACP reductase (FabG) of the native *E. coli* fatty acid biosynthetic machinery.

Example 4B: Production of 1,3-Diols Using a Pathway with phaG from *Pseudomonas putida* and carB This example shows the production of 1,3-diols in recombinant *E. coli* using a metabolic pathway including a thioesterase/transacylase, phaG, from *Pseudomoans putida* (genbank accession number AAN67031), and a variant carboxylic acid reductase, CarB, from *Mycobacterium smegmatis*.

The gene coding for carB8 (see sequence listing enclosed herewith, infra) and phaG were cloned into a pCL1920-derivative vector (SC101 replicon, spectinomycin resistance marker), such that their transcription was controlled by the IPTG-inducible Ptrc promoter and they formed an operon with a gene coding for an alcohol dehydrogenase, alrA. The plasmid was named pNH328 (see Table 5).

Base strain used for plasmid transformation was strain D178. Briefly, the genome of strain D178 was modified as follow: the fadE (acyl-CoA dehydrogenase) gene was deleted and a phosphopantetheinyl transferase (entD) was overexpressed. Plasmid pNH328 was transformed into D178 resulting in strain stNH1369 (see Table 6, supra). The strain was then cultivated and analyzed for its ability to produce fatty alcohols and 1,3-diols as described in Examples 1 and 2. The 1,3-diol peaks were identified as described in Example 2.

Strain stNH1369 produced 600±27 mg/L 1,3-diols in a HTP fermentation protocol. 1,3-diols produced were 1,3-octanediol, 1,3-decanediol, 1,3-dodecanediol and 1,3 tetradecanediol. Besides 1,3-diols, only minor amounts of fatty acids were detected. Analysis of the 1,3, diols may show they are highly enriched in (R) enantiomer demonstrating the enantioselectivity of the 3-ketoacyl ACP reductase (FabG) of the native *E. coli* fatty acid biosynthetic machinery.

Example 5: Production of 1,3-Diols Using a Pathway with AAR from *Synechococcus elongatus*

This example shows the production of 1,3-diols in recombinant *E. coli* using a metabolic pathway including a variant acyl-ACP reductase, AAR, from *Synechococcus elongatus* (genbank accession number YP_400611; wildtype). For the variant AAR sequence see sequence listing enclosed herewith (infra).

The gene coding for an AAR variant (SEQ ID NO: 2) was cloned into a pCL1920-derivative vector (SC101 replicon, spectinomycin resistance marker), such that its transcription was controlled by the IPTG-inducible Ptrc promoter and it formed an operon with a gene coding for an alcohol dehydrogenase, alrA. The plasmid was named pNT16 (see Table 5).

Base strain used for plasmid transformation was DV2. Briefly, the genome of strain DV2 was manipulated by deleting the fadE (acyl-CoA dehydrogenase) gene. Plasmid pNT16 was transformed into base strains DV2 resulting in strain Becos247 (see Table 6). Becos247 was then cultivated and analyzed for its ability to produce fatty alcohols as described in Examples 1 and 2. Surprisingly, the strain produced 1,3-diols. The 1,3-diol peaks were identified as described in Example 2.

Strain Becos247 produced 0.57 g/L 1,3-diols in a 5 L fermentation, which constituted 9.1% of the total fatty acid species produced. 1,3-diols produced were 1,3-dodecanediol, 1,3 tetradecanediol and 1,3 tetradecanediol, in addition the fatty alcohols decanol, dodecenol, dodecanol, tetradecenol, tetradecanol, hexadecenol, hexadecanol and octadecenol as well as minor quantities of fatty acids were produced.

The production of 1,3-diols in this experiment via 3-OH fatty aldehydes as intermediates is surprising (see FIG. 3), because the acyl-ACP reductase used in this example, wild type AAR from *Synechococcus elongatus*, has been previously expressed in *E. coli* and was reported only to give rise to fatty alcohols from acyl-ACPs but not 1,3-diols from 3-OH acyl-ACPs (Schirmer et al. (2010) *Science* 329, 559). Analysis of the 1,3, diols may show they are highly enriched in (R) enantiomer demonstrating the enantioselectivity of the 3-ketoacyl ACP reductase (FabG) of the native *E. coli* fatty acid biosynthetic machinery.

Example 6A: Production of 1,3-Diols Using a Pathway with fatB1 from *Umbellularia californica* and carB This example describes how to demonstrate production of 1,3-diols in recombinant *E. coli* using a metabolic pathway including a plant thioesterase, fatB1, from *Umbellularia california*, and carboxylic acid reductase, carB, from *Mycobacterium smegmatis*.

The genes coding for wildtype carB and fatB1 are cloned into a pCL1920-derivative vector (SC101 replicon, spectinomycin resistance marker), such that their transcription is controlled by the IPTG-inducible Ptrc promoter and they form an operon with a gene coding for an alcohol dehydrogenase, alrA. The plasmid is transformed into a base strain such as strain DV2 (see Example 5).

The resulting strain is then cultivated and analyzed for its ability to produce fatty alcohols and diols as described in Examples 1 and 2. The strain is expected to produce 1,3-diols. Analysis of the 1,3, diols will show they are highly enriched in (R) enantiomer demonstrating the enantioselectivity of the 3-ketoacyl ACP reductase (FabG) of the native *E. coli* fatty acid biosynthetic machinery.

Example 6B: Production of 1,3-Diols Using a Simplified Pathway with fatB1 from *Umbellularia californica* and carB This example describes how to demonstrate production of 1,3-diols in recombinant *E. coli* using a simplified metabolic pathway including a plant thioesterase, fatB1, from *Umbellularia california*, and carboxylic acid reductase, carB, from *Mycobacterium smegmatis*.

The genes coding for wildtype carB and fatB1 are cloned into a pCL1920-derivative vector (SC101 replicon, spectinomycin resistance marker), such that their transcription is controlled by the IPTG-inducible Ptrc promoter. The plasmid is transformed into a base strain such as strain DV2 (see Example 5).

The resulting strain is then cultivated and analyzed for its ability to produce fatty alcohols and diols as described in Examples 1 and 2. The strain is expected to produce 1,3-diols, which demonstrates that a thioesterase and carboxylic acid reductase are sufficient to enable the microbial cell to produce 1,3 diolsAnalysis of the 1,3, diols will show they are highly enriched in (R) enantiomer demonstrating the enantioselectivity of the 3-ketoacyl ACP reductase (FabG) of the native *E. coli* fatty acid biosynthetic machinery.

Example 7: Production of 1,3-Diols Using a Pathway with tesA from *E. coli* and carB This example describes how to demonstrate production of 1,3-diols in recombinant *E. coli* using a metabolic pathway including thioesterase, tesA, and carboxy acid reductase, CarB, from *Mycobacterium smegmatis*.

The genes coding for wildtype carB and wildtype tesA are cloned into a pCL1920-derivative vector (SC101 replicon, spectinomycin resistance marker), such that their transcription is controlled by the IPTG-inducible Ptrc promoter and they form an operon with a gene coding for an alcohol dehydrogenase, alrA. The plasmid is transformed into a base strain such as strain DV2 (see Example 5).

The resulting strain is then cultivated and analyzed for its ability to produce fatty alcohols and diols as described in examples 1 and 2. The strain is expected to produce 1,3-diols, which demonstrates that a thioesterase and carboxylic acid reductase are sufficient to enable the microbial cell to produce 1,3 diolsAnalysis of the 1,3, diols will show they are highly enriched in (R) enantiomer demonstrating the enantioselectivity of the 3-ketoacyl ACP reductase (FabG) of the native *E. coli* fatty acid biosynthetic machinery.

Example 8: Production of 1,3-Diols Using a Simplified Pathway with Wildtype AAR from *Synechococcus elongatus*

This example describes how to demonstrate production of 1,3-diols in recombinant *E. coli* using a metabolic pathway including acyl-ACP reductase, AAR, from *Synechococcus elongatus*.

The gene coding for wildtype AAR is cloned into a pCL1920-derivative vector (SC101 replicon, spectinomycin resistance marker), such that its transcription is controlled by the IPTG-inducible Ptrc promoter. The plasmid is transformed into a base strain such as strain DV2 (see Example 5).

The resulting strain is then cultivated and analyzed for its ability to produce fatty alcohols and diols as described in examples 1 and 2. The strain is expected to produce 1,3-diols which demonstrates that heterologous production of AAR is sufficient to enable the microbial cell to produce 1,3 diols Analysis of the 1,3, diols will show they are highly enriched in (R) enantiomer demonstrating the enantioselectivity of the 3-ketoacyl ACP reductase (FabG) of the native *E. coli* fatty acid biosynthetic machinery.

Example 9: Production of 1,3-Diols Using a Pathway with fatB from *Cinnamomum camphora* and carB This example describes how to demonstrate production of 1,3-diols in recombinant *E. coli* using a metabolic pathway including a plant thioesterase, fatB, from *Cinnamomum camphora* and carboxylic acid reductase, carB, from *Mycobacterium smegmatis*.

The genes coding for wildtype carB and fatB from *Cinnamomum camphora* are cloned into a pCL1920-derivative vector (SC101 replicon, spectinomycin resistance marker), such that their transcription is controlled by the IPTG-inducible Ptrc promoter and they form an operon with a gene coding for an alcohol dehydrogenase, alrA. The plasmid is transformed into a base strain such as strain DV2 (see Example 5).

The resulting strain is then cultivated and analyzed for its ability to produce fatty alcohols and diols as described in Examples 1 and 2. The strain is expected to produce 1,3-diols, which demonstrates that a thioesterase and carboxylic acid reductase are sufficient to enable the microbial cell to produce 1,3 diols Analysis of the 1,3, diols will show they are highly enriched in (R) enantiomer demonstrating the enantioselectivity of the 3-ketoacyl ACP reductase (FabG) of the native *E. coli* fatty acid biosynthetic machinery.

Example 10: Production of 1,3-Diols Using a Pathway with acr1 from *Acinetobacter Baylyi*

This example describes how to demonstrate production of 1,3-diols in recombinant *E. coli* using a metabolic pathway including fatty acyl-CoA reductase, acr1, from *Acinetobacter baylyi* (genbank accession number AAC45217).

The gene coding for acr1 is cloned into a pCL1920-derivative vector (SC101 replicon, spectinomycin resistance marker), such that its transcription is controlled by the IPTG-inducible Ptrc promoter and it forms an operon with genes coding for an acyl-CoA synthetase (fadD) and a thioesterase. The plasmid is transformed into a base strain such as strain DV2 (see Example 5).

The resulting strain is then cultivated and analyzed for its ability to produce fatty alcohols and diols as described in Examples 1 and 2. The strain is expected to produce 1,3-diols.

Example 11: Production of 1,3-Diols Using a Pathway with FAR from *Marinobacter aquaeolei*

This example describes how to demonstrate production of 1,3-diols in recombinant *E. coli* using a metabolic pathway including fatty acyl-ACP reductase, FAR, from *Marinobacter aquaeolei* (genbank accession number YP_959486).

The genes coding for wildtype FAR is cloned into a pCL1920-derivative vector (SC101 replicon, spectinomycin resistance marker), such that its transcription is controlled by the IPTG-inducible Ptrc promoter. The plasmid is transformed into a base strain such as strain DV2 (see Example 5).

The resulting strain is then cultivated and analyzed for its ability to produce fatty alcohols and diols as described in examples 1 and 2. The strain is expected to produce 1,3-diols, which demonstrates that heterologously produced FAR is sufficient to enable the cell to produce 1,3 diols

Example 12: Production of 1,3-Diols Using a Pathway with a FAR Complex from *Photorhabdus luminescens*

This example describes how to demonstrate production of 1,3-diols in recombinant *E. coli* using a metabolic pathway including a fatty acyl-ACP reductase, FAR, complex that includes LuxC, LuxD and LuxE from *Photorhabdus luminescens* (genbank accession numbers AHH25015-17).

The genes coding for LuxC, LuxD and LuxE are cloned into a pCL1920-derivative vector (SC101 replicon, spectinomycin resistance marker), such that their transcription is controlled by the IPTG-inducible Ptrc promoter and they form an operon with a gene coding for an alcohol dehydrogenase, alrA. The plasmid is transformed into a base strain such as strain DV2 (see Example 5).

The resulting strain is then cultivated and analyzed for its ability to produce fatty alcohols and diols as described in Examples 1 and 2. The strain is expected to produce 1,3-diols.

Example 13: Production of 3-(S)-Fatty Diols Using fadB(His450Gln)

This example describes how to demonstrate production 3-(S)-fatty diols in recombinant E. coli using a metabolic pathway including a 3-hydroxy-acyl-ACP Acyl-CoA transacylase or thioesterase fadB(His450Gln) that retains enoyl-CoA hydratase activity but is deficient in dehydrogenase activity, and expresses a fatty acyl-CoA reductase, acr1, from Acinetobacter baylyi (genbank accession number AAC45217).

The genes coding for 'TesA, FadD, FadB(His450Gln) and Acr1 are cloned into a pCL1920-derivative vector (SC101 replicon, spectinomycin resistance marker), such that their transcription is controlled by the IPTG-inducible Ptrc promoter and they complete an operon sufficient for the synthesis of a fatty alcohol. The plasmid is transformed into a base strain such as strain MG1655 (see Example 5) in which an additional gene encoding FadE has been introduced into the genome under the control of the IPTG inducible Ptrc promoter.

The resulting strain is then cultivated and analyzed for its ability to produce fatty alcohols and diols as described in Examples 1 and 2. The strain is expected to produce 3-(S)-fatty diols.

Example 14. Production of 3-(S)-Fatty Diols Using fadB(Glu119Gln)

This example describes how to demonstrate production 3-(S)-fatty diols in recombinant E. coli using a metabolic pathway including a 3-hydroxy-acyl-ACP Acyl-CoA transacylase or thioesterase, fadB(Glu119Gln) which retain dehydrogenase activity but are deficient in dehydratase activity, and express a fatty acyl-CoA reductase, acr1, from Acinetobacter baylyi (genbank accession number AAC45217).

The genes coding for 'TesA, FadD, FadB(Glu119Gln) and Acr1 are cloned into a pCL1920-derivative vector (SC101 replicon, spectinomycin resistance marker), such that their transcription is controlled by the IPTG-inducible Ptrc promoter and they complete an operon sufficient for the synthesis of a fatty alcohol. The plasmid is transformed into a base strain such as strain MG1655 (see Example 5) in which an additional gene encoding FadA has been introduced into the genome under the control of the IPTG inducible Ptrc promoter.

The resulting strain is then cultivated and analyzed for its ability to produce fatty alcohols and diols as described in Examples 1 and 2. The strain is expected to produce 3-(S)-fatty diols.

As is apparent to one with skill in the art, various modifications and variations of the above aspects and embodiments can be made without departing from the spirit and scope of this disclosure. Such modifications and variations are within the scope of this disclosure.

We claim:

1. A recombinant *Escherichia coli* (*E. coli*) for producing a 1,3 fatty diol when grown in a fermentation broth with a simple carbon source, the *E. coli* engineered to express heterologous nucleic acid sequences encoding a thioesterase having the classification EC 3.1.2.2, EC 3.1.1.5, or EC 3.1.2.14; and a carboxylic acid reductase having the classification EC 1.2.99.6, wherein the thioesterase uses 3-hydroxy acyl-ACP as a substrate and is selected from the group consisting of TE_EEI82564, TE_CAD63310, and phaG and wherein the carboxylic acid reductase is selected from the group consisting of carB from *Mycobacterium smegmatis*, carA from *Mycobacterium smegmatis*, FadD9 from *Mycobacterium smegmatis*, car from *Mycobacterium genavense*, car from *Nocardia lowensis*, and car from *Nocardia brasiliensis*.

2. The recombinant *E. coli* of claim 1, wherein said 1,3 fatty diol is produced in vivo.

3. The recombinant *E. coli* of claim 1, wherein said 1,3 fatty diol is selected from the group consisting of a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol.

4. The recombinant *E. coli* of claim 1, further expressing a nucleic acid sequence encoding an alcohol dehydrogenase having the classification EC 1.1.1.-.

5. The recombinant *E. coli* of claim 1, wherein said simple carbon source is derived from a renewable feedstock.

6. The recombinant *E. coli* of claim 1, wherein said carboxylic acid reductase is carB.

7. The recombinant *E. coli* of claim 4, wherein said alcohol dehydrogenase is alrA.

8. A cell culture comprising the *E. coli* according to claim 1.

9. The cell culture of claim 8, wherein said cell culture produces 1,3 fatty diols.

10. The cell culture of claim 9, wherein said 1,3 fatty diol is selected from the group consisting of a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol.

11. A method of producing a 1,3 fatty diol comprising culturing the *E. coli* of claim 1.

12. A method of producing a 1,3 fatty diol comprising: (i) culturing a recombinant *E. coli* in a fermentation broth, wherein said *E. coli* expresses heterologous nucleic acid sequences encoding a thioesterase having the classification EC 3.1.2.2, EC 3.1.1.5, or EC 3.1.2.14; and a carboxylic acid reductase having the classification EC 1.2.99.6, and optionally an alcohol dehydrogenase having the classification EC 1.1.1.1 or 1.1.1.2; wherein the thioesterase uses 3-hydroxy acyl-ACP as a substrate and is selected from the group consisting of tesA (with leader sequence) from *E. coli*, tesA (without leader sequence) from *E. coli*, tes from *Photbacterium profundum*, tesB from *E. coli*, TE CAD63310 from *Lactobacillus plantarum*, TE EEI82564 from *Anaerococcus tetraclius*, fatB1 from *Umbellularia californica*, fatB2 from *Cuphea hookeriana*, fatB3 from *Cuphea hookeriana*, fatB from *Cinnamomurn camphora*, fatB from *Arabidopsis thaliana*, fatA1 from *Helianthus animus*, fatA from *Brassica juncea*, fatA from *Cuphea hookeriana*, fadM from *Escherichia coli*, yciA from *Escherichia coli*, ybgC from *Escherichia coli*, and phaG from *Pseudomonas putida*, and wherein the carboxylic acid reductase is selected from the group consisting of carB from *Mycobacterium smegmatis*, carA from *Mycobacterium smegmatis*, FadD9 from *Mycobacterium smegmatis*, car from *Mycobacterium genavense*, car from *Nocardia lowensis*, and car from *Nocardia brasiliensis*; and (ii) isolating a 1,3 fatty diol from said fermentation broth, wherein said fermentation broth comprises a simple carbon source.

13. The method of claim 12, wherein said 1,3 fatty diol is selected from the group consisting of a $C_5$ 1,3 fatty diol, a $C_6$ 1,3 fatty diol, a $C_7$ 1,3 fatty diol, a $C_8$ 1,3 fatty diol, a $C_9$ 1,3 fatty diol, a $C_{10}$ 1,3 fatty diol, a $C_{11}$ 1,3 fatty diol, a $C_{12}$ 1,3 fatty diol, a $C_{13}$ 1,3 fatty diol, a $C_{14}$ 1,3 fatty diol, a $C_{15}$ 1,3 fatty diol, a $C_{16}$ 1,3 fatty diol, a $C_{17}$ 1,3 fatty diol, a $C_{18}$ 1,3 fatty diol, and a $C_{19}$ 1,3 fatty diol.

* * * * *